US010564076B2

(12) United States Patent
Lucas et al.

(10) Patent No.: US 10,564,076 B2
(45) Date of Patent: Feb. 18, 2020

(54) COMPOSITIONS AND METHODS FOR ANALYTICAL SAMPLE PREPARATION

(71) Applicant: Agilent Technologies, Inc., Loveland, CA (US)

(72) Inventors: Derick Lucas, Wilmington, DE (US); Bruce Richter, Wilmington, DE (US); David Long, Glen Mills, PA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 637 days.

(21) Appl. No.: 14/740,829

(22) Filed: Jun. 16, 2015

(65) Prior Publication Data
US 2016/0370357 A1 Dec. 22, 2016

(51) Int. Cl.
*G01N 1/00* (2006.01)
*G01N 1/34* (2006.01)
*G01N 1/40* (2006.01)
G01N 30/00 (2006.01)
B82Y 30/00 (2011.01)
B82Y 40/00 (2011.01)

(52) U.S. Cl.
CPC ............. *G01N 1/34* (2013.01); *G01N 1/405* (2013.01); *B82Y 30/00* (2013.01); *B82Y 40/00* (2013.01); *G01N 2001/4016* (2013.01); *G01N 2001/4088* (2013.01); *G01N 2030/009* (2013.01)

(58) Field of Classification Search
CPC ...................................................... G01N 1/34
USPC ....................................................... 436/177
See application file for complete search history.

(56) References Cited

U.S. PATENT DOCUMENTS

| 3,472,835 | A | 10/1969 | Locke et al. |
| 4,426,292 | A | 1/1984 | Wernick et al. |
| 5,152,998 | A | 10/1992 | Casu et al. |
| 5,208,316 | A | 5/1993 | Yoshinaga |

(Continued)

FOREIGN PATENT DOCUMENTS

| CN | 101344648 A | 1/2009 |
| EP | 0301847 | 2/1989 |

(Continued)

OTHER PUBLICATIONS

Ma et al. Chem. Mater. 1999, 11, 872-874 (Year: 1999).*

(Continued)

*Primary Examiner* — Christine T Mui
*Assistant Examiner* — Emily R. Berkeley

(57) ABSTRACT

Aspects of the present disclosure include a system for analytical sample preparation. In some embodiments, the system includes a container having disposed therein an analytical sample treatment composition including α-cyclodextrin and/or an α-cyclodextrin co-polymer. Also provided is a method of reducing matrix effects in an analytical sample. In some embodiments, the method includes: contacting a sample including a matrix-interfering agent and an analyte with a cyclodextrin composition to produce a matrix-cyclodextrin complex, wherein the cyclodextrin composition comprises an α-cyclodextrin and/or an α-cyclodextrin co-polymer; separating the complex from the contacted sample to produce a matrix-reduced composition; and detecting the analyte in the matrix-reduced composition. Kits and compositions for use in the subject systems and methods are also provided.

20 Claims, 16 Drawing Sheets

(56) References Cited

U.S. PATENT DOCUMENTS

| | | | |
|---|---|---|---|
| 5,232,725 | A | 8/1993 | Roderbourg et al. |
| 5,412,127 | A | 5/1995 | Menlink et al. |
| 5,705,345 | A | 1/1998 | Lundin et al. |
| 5,723,236 | A | 3/1998 | Inoue et al. |
| 5,750,164 | A | 5/1998 | Saito et al. |
| 5,759,549 | A | 6/1998 | Hiltunen et al. |
| 5,885,921 | A | 3/1999 | Krupey |
| 6,770,246 | B1 | 8/2004 | Husek |
| 7,091,192 | B1 | 8/2006 | Davis et al. |
| 7,256,049 | B2 | 8/2007 | Bennett et al. |
| 7,745,558 | B2 | 6/2010 | Choi et al. |
| 7,999,084 | B2 | 8/2011 | Jones |
| 2001/0008222 | A1* | 7/2001 | Ma ............... C08G 18/6484 210/767 |
| 2008/0213906 | A1 | 9/2008 | Aurand et al. |
| 2010/0291688 | A1 | 11/2010 | Lu et al. |
| 2013/0053588 | A1 | 2/2013 | Iraneta et al. |

FOREIGN PATENT DOCUMENTS

| | | |
|---|---|---|
| WO | WO1998022197 | 5/1998 |
| WO | 2006039077 A2 | 4/2006 |

OTHER PUBLICATIONS

Yamaguchi et al. Polymer Bulletin 44, 247-253 (2000) (Year: 2000).*

Abbate et al. Polym. Chem., 2012, 3, 2018 (Year: 2012).*

Murakami et al. Polymer 56 (2015) 368-374 (Year: 2015).*

Arima, et al. "Potential Use of Polyamidoamine Dendrimer Conjugates with Cyclodextrins as Novel Carriers for siRNA", Pharmaceuticals 2012,5, 61-78.

Bhaskar, et al. "b-Cyclodextrin-polyurethane polymer as solid phase extraction material for the analysis of carcinogenic aromatic amines", Analytica Chimica Acta 509 (2004) 39-45.

Crini, et al. "Synthesis and applications of adsorbents containing cyclodextrins", J. Sep. Sci. 2002,25,789-813.

Little, et al. "Liquid chromatography—mass spectrometry/mass spectrometry method development for drug metabolism studies: Examining lipid matrix ionization effects in plasma", Journal of Chromatography B, 833 (2006) 219-230.

Mohamed, et al. "Design and characterization of novel b-cyclodextrin based copolymer materials", Carbohydrate Research 346 (2011) 219-229.

Rawyer, et al. Cyclodextrins: a new tool for the controlled lipid depletion of thylakoid membranes, Biochimica et Biophysica Acta 1278 (1996) 89-97.

Sharma, et al. "Flocculation of Serum Lipoproteins with Cyclodextrins: Application to Assay of Hyperlipidemic Serum", Clin. Chem. 36/3, 529-532, (1990).

Sharma, et al. "Lipoprotein-cyclodextrin interaction", Clinicu Chimica Acta, 199 (1991) 129-138.

Wilson, et al. "Surface area and pore structure properties of urethane-based copolymers containing b-cyclodextrin", Journal of Colloid and Interface Science 357 (2011) 215-222.

Extended European Search Report dated Apr. 23, 2018, Application No. 16812085.5, 9 pages.

Jeongjin, Son et al., MALDI Mass Spectrometric Analysis of Nonderivatized Steroids Using Cyclodextrin-supported 2,5-Dihydroxybenzoic Acid as Matrix, Bulletin of the Korean Chemical Society, vol. 35, No. 5, May 20, 2014, 1409-1412.

* cited by examiner

A

B

COMPOSITIONS AND METHODS FOR ANALYTICAL SAMPLE PREPARATION

INTRODUCTION

Analytical testing and quantitation methods suffer from interferences caused by contaminants in a sample matrix that can decrease or increase sensitivity to various analytes disproportionately to their abundance in the sample. For example, liquid chromatography-mass spectrometry/mass spectrometry (LC/MS-MS) is a commonly used method for drug metabolism studies; however matrix effects can lead to significant analytical errors from decreased precision, selectivity and sensitivity. For example, phospholipids such as phosphatidylcholines interfere with analyte ionization in electrospray MS detection by reducing analyte sensitivity, commonly referred to as ion suppression or matrix effects.

The presence of contaminants can result in incomplete solvent extraction and hence underreporting of analyte concentrations, or can build up on analytical instrumentation, destroying sensitivity or resulting in downtime while cleaning procedures are instituted. For example, contaminants such as phospholipids have a tendency to build up on a reverse phase HPLC column during repeated analyses of precipitated plasma samples. Accumulated phospholipids can bleed off in subsequent injections, causing a drift in analyte sensitivity over the course of multiple injections. Removing the phospholipids requires extensive solvent washing to regenerate a column to proper condition. Numerous methods for removing contaminants in analytical samples are available, including liquid/liquid extraction (LLE), protein precipitation (PPT) and solid phase extraction (SPE).

QuEChERS is a streamlined method used by analytical chemists to examine analytes such as pesticide residues in food. The name is a portmanteau word formed from "Quick, Easy, Cheap, Effective, Rugged, and Safe". The QuEChERS method can be modified to ensure efficient extraction of pH dependent compounds (e.g. phenoxyalcanoic acids), to minimize degradation of susceptible compounds (e.g. base and acid labile pesticides) or to expand the spectrum of matrices covered. The analyst homogenizes the sample (e.g., fruits, vegetables, tobacco, etc.) in a blender and puts it in a centrifuge tube with a reagent and agitates for one minute. The reagents used depend on the type of sample to be analyzed. Following homogenization the sample can be eluted through a cleanup column prior to analysis.

Many sample preparation methods suffer from the potential for analyte losses and significant matrix effects during MS analysis of analytes. There are multiple sample components that can be involved in ion suppression, whose effects result in the collection of invalid data. Procedures that can remove both lipids and other agents causing matrix effects from an analytical sample prior to performance of analytical procedures are of interest.

SUMMARY

Aspects of the present disclosure include a system for analytical sample preparation. In some embodiments, the system includes a container having disposed therein an analytical sample preparation composition including α-cyclodextrin (α-CD) and/or an α-cyclodextrin co-polymer. Also provided is a method of reducing matrix effects in an analytical sample. In some embodiments, the method includes: contacting a sample including a matrix-interfering agent and an analyte with an α-cyclodextrin composition to produce a matrix-cyclodextrin complex, wherein the α-cyclodextrin composition comprises an α-cyclodextrin and/or an α-cyclodextrin co-polymer; separating the complex from the contacted sample to produce a matrix-reduced composition; and detecting the analyte in the matrix-reduced composition. Kits and compositions for use in the subject systems and methods are also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
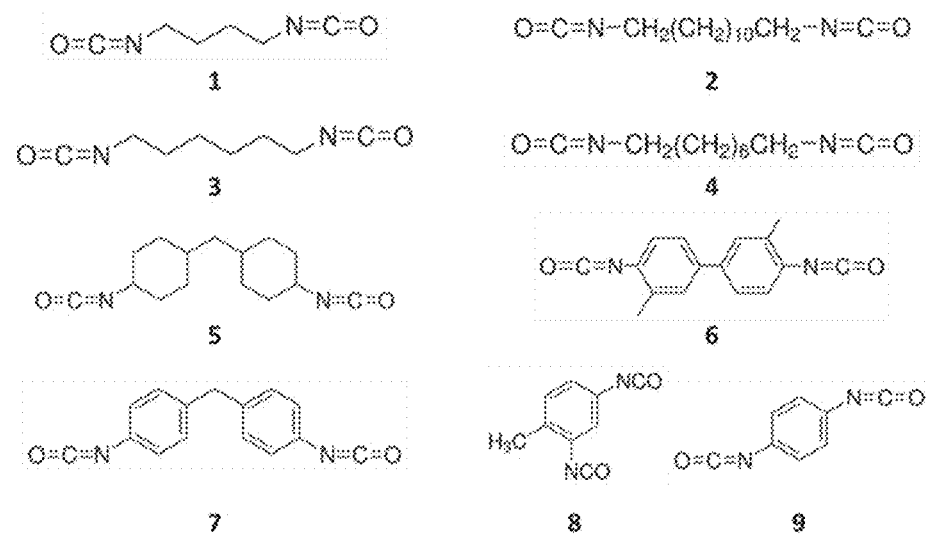
FIG. 1 illustrates diisocyanate monomers of interest (panel A) that find use in the synthesis of α-cyclodextrin co-polymers as depicted in an exemplary scheme (panel 8).
Figure 1:
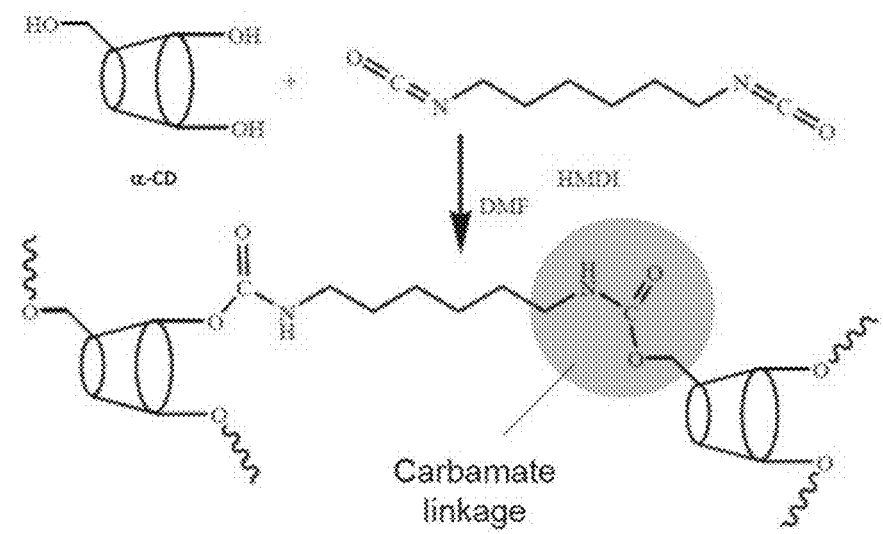

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "an α-cyclodextrin" refers to one or more α-cyclodextrins, i.e., a single α-cyclodextrin and multiple α-cyclodextrins. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "linker" or "linkage" refers to a linking moiety that connects two groups and has a backbone of 100 atoms or less in length. A linker or linkage can be a covalent bond that connects two groups or a chain of between 1 and 100 atoms in length, for example of 1, 2, 3, 4, 5, 6, 8, 10, 12, 14, 16, 18 or 20 carbon atoms in length, where the linker can be linear, branched, cyclic or a single atom. In certain cases, one, two, three, four or five or more carbon atoms of a linker backbone can be optionally substituted with a sulfur, nitrogen or oxygen heteroatom. The bonds between backbone atoms can be saturated or unsaturated, usually not more than one, two, or three unsaturated bonds will be present in a linker backbone. The linker can include one or more substituent groups, for example with an alkyl, aryl or alkenyl group. A linker can include, without limitations, poly(ethylene glycol); ethers, thioethers, tertiary amines, alkyls, which can be straight or branched, e.g., methyl, ethyl, n-propyl, 1-methylethyl (isopropyl), n-butyl, n-pentyl, 1,1-dimethylethyl (t-butyl), and the like. The linker backbone can include a cyclic group, for example, an aryl, a heterocycle or a cycloalkyl group, where 2 or more atoms, e.g., 2, 3 or 4 atoms, of the cyclic group are included in the backbone. A linker can be cleavable or non-cleavable.

As used herein, the term "specific binding member" refers to one member of a pair of molecules which have binding specificity for one another. One member of the pair of molecules can have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as, inter alia, $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

The methods described herein include multiple steps. Each step can be performed after a predetermined amount of time has elapsed between steps, as desired. As such, the time between performing each step can be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step can be performed after an incubation or waiting time after completion of the previous step, e.g., a few minutes to an overnight waiting time.

A "plurality" contains at least 2 members. In certain cases, a plurality can have at least 6, at least 10, at least 12, at least 24, at least 48, at least 96, at least 100, at least 384, at least 10,000, at least 100,000, at least $10^6$, at least $10^7$, at least $10^8$ or at least $10^9$ or more members.

Numeric ranges are inclusive of the numbers defining the range.

The term "separating", as used herein, refers to physical separation of two elements (e.g., by size or affinity, etc.) as well as degradation of one element, leaving the other intact.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ can be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—, n-propylene (—CH$_2$CH$_2$CH$_2$—), iso-propylene (—CH$_2$CH(CH$_3$)—), (—C(CH$_3$)$_2$CH$_2$CH$_2$—), (—C(H$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings can or can not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^+$M$^-$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{07}$CO$_2$$^-$M$^+$, —NR$^{70}$CO(NR$^{70}$), —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which can optionally include from 1 to 4 of the same or different additional heteroatoms selected from the group consisting of O, N and S, of which N can have —H or C$_1$-C$_3$ alkyl substitution; and each M$^+$ is a counter ion with a net single positive charge. Each M$^+$ can independently be, for example, an alkali ion, such as K$^+$, Na$^+$, Li$^+$; an ammonium ion, such as $^+$N(R$^{50}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the disclosure herein, in a certain embodiment, a group that is substituted has 1, 2, 3, or 4 substituents, 1, 2, or 3 substituents, 1 or 2 substituents, or 1 substituent. It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The terms "derivatized" and "derived from" refers to chemical modification of molecules. The skilled artisan would readily recognize the variety of ways molecules can be modified, such as oxidations, reductions, electrophilic/nucleophilic substitutions, alkylations, ester/amide formations and the like. For example, cyclodextrins of the present invention can be chemically modified by amination, tosylation, or iodination prior to polymerization or covalently attaching them to a polymer.

Other definitions of terms can appear throughout the specification.

DETAILED DESCRIPTION

As summarized above, aspects of the present disclosure include a system for analytical sample preparation. In some embodiments, the system includes a container having disposed therein an analytical sample treatment composition including α-cyclodextrin and/or an α-cyclodextrin co-polymer. Also provided is a method of reducing matrix effects in an analytical sample. In some embodiments, the method includes: contacting a sample including a matrix-interfering agent and an analyte with an α-cyclodextrin composition to produce a matrix-cyclodextrin complex, wherein the α-cyclodextrin composition comprises an α-cyclodextrin and/or an α-cyclodextrin co-polymer, separating the complex from the contacted sample to produce a matrix-reduced composition; and detecting the analyte in the matrix-reduced composition. Kits and compositions for use in the subject systems and methods are also provided.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, compositions that find use in analytical sample treatment are described first in greater detail. Next, systems and kits of interest for including the subject compositions are reviewed. Finally, methods of reducing matrix effects in an analytical sample are also described.

Compositions

Aspects of the present disclosure include a composition for analytical sample preparation. The composition can include an α-cyclodextrin and/or an α-cyclodextrin co-polymer. In some embodiments of the composition, the analytical sample preparation composition includes α-cyclodextrin. In some embodiments of the composition, the analytical sample preparation composition includes α-cyclodextrin co-polymer. In some embodiments of the composition, the analytical sample preparation composition includes a mixture of α-cyclodextrin and α-cyclodextrin co-polymer. As used herein, the terms "α-cyclodextrin", "α-dextrin", "alpha-cyclodextrin", "α-CD" and "alphadextrin" are used interchangeably and refer to a cyclic polysaccharide including six glucose subunits that are cyclically linked via α-1,4 intersubunit linkages. The term can be used in the context of a single monomeric compound, e.g., a compound that includes one α-cyclodextrin. The term can also be used in the context of a polymer, e.g., a co-polymer that includes α-cyclodextrin co-monomers. The term can be used to refer to monomeric α-cyclodextrin compounds or to α-cyclodextrin co-polymers. The glucose subunits of the α-cyclodextrin moieties can be naturally occurring sugars, in their reduced or oxidized forms. In some instances, the glucose subunits of the α-cyclodextrin are α-D-glucopyranoside units. The α-cyclodextrin moieties can be modified. A modified α-cyclodextrin is a moiety (e.g., a monomer or co-polymer) that includes at least one modified glucose subunit. Modifications of interest include, but are not limited to, modification at a 2-, 3- and/or 6-hydroxyl groups of a glucose unit (e.g., alkylation or acylation with any convenient linking moiety), substitution or transformation of a hydroxyl group (e.g., a 2-, 3- and/or 6-hydroxyl group) with an alternative functional group (e.g., an amine, a thiol, an aldehyde, a ketone, an azide, a carboxylic acid, an active ester, an isocyanate, an isothiocyanate, etc). α-Cyclodextrin moieties can include an optional linker for attachment to a co-polymer or other moiety of interest. The linkage can be covalent (e.g., via biohydrolyzable bonds, e.g., esters, amides, carbamates, and carbonates). α-Cyclodextrin moieties can further include one or more carbohydrate moieties, in some cases, simple carbohydrate moieties such as galactose, attached to the cyclic core, either directly (i.e., via a carbohydrate linkage) or through a linker group. The glucose subunits of the α-cyclodextrin can be the same or different. In some cases, one or more of the glucose subunits is modified to provide for covalent linking of the α-cyclodextrin to a moiety of interest.

The selectivity of the α-cyclodextrin compound and/or co-polymer can be derived from a particular cavity size which restricts formation of inclusion complexes (i.e., a host-guest complex) to only those guest components able to be incorporated within the cavity of the α-cyclodextrin. Cavity size is a major determinant as to which components of the sample can be complexed. α-Cyclodextrins have small cavities (e.g., having an internal diameter of about 4.7 to about 5.3 angstroms relative to β- or γ-cyclodextrins, which have internal diameters of 6.0 to 6.5 angstroms and 7.5 to 8.3 angstroms, respectively) that are not capable of accepting molecules or groups having a larger size. The spatial fit of the component which binds in the α-cyclodextrin cavity is important to achieving complex formation. As such, sample components that are too large to be included inside the α-cyclodextrin cavity remain unbound in solution.

Hydrophobic sample components of interest can be incorporated into the cavity of an α-cyclodextrin compound or co-polymer by displacing water. This binding event is favored by the repulsion of the molecule by water and effectively encapsulates the guest component of interest within the cyclodextrin, rendering the component water-soluble.

For example, in some cases, the sample includes a guest component of interest that is a lipid. Lipids have an extensive and complex role in biology and are found in the matrix of many types of samples. A lipid has a hydrophilic head group and a hydrophobic tail that includes a hydrocarbon chain. The hydrophobic tail of a lipid can have a linear extended structure that is cylindrical, i.e., a structure having a generally consistent diameter and a variable length determined by the length of the hydrocarbon chain. A lipid hydrocarbon chain can have any one of a variety of combination of lengths, substitution patterns, and degrees of unsaturation. Lipids have physical properties such as shape, rigidity and size. Membrane lipids can be classified according to their molecular shape: e.g., inverted cone, cylindrical and cone, which can determine membrane structure and biological function. Cylindrical shaped lipids are lipids whose hydrophilic head group and hydrophobic tail have similar diameters. Inverted cone shaped lipids are those in which the polar head group is greater in diameter than the lipid tail. Cone shaped lipids are those in which the polar head group is smaller in diameter than the lipid tail. In general terms, the hydrocarbon chains of lipids have an average diameter and shape that is capable of incorporation into the cavity of an α-cyclodextrin monomer/compound or co-polymer. In some cases, depending of the length of the hydrocarbon chain, the hydrocarbon chain can form a host-guest complex with multiple α-cyclodextrin moieties simultaneously (e.g., multiple monomers and/or multiple α-cyclodextrin groups of a co-polymer). Lipids of interest that can be capable of forming complexes with the subject α-cyclodextrin compositions include, but are not limited to sphingolipids, glycophospholipids, acylglycerides and cholesterols.

In general terms, the subject compositions include an α-cyclodextrin compound and an α-cyclodextrin co-polymer that can selectively bind a target component of a sample of interest to produce a complex. In some cases, the complex is a termolecular complex, or an even higher order complex, and can include both an α-cyclodextrin co-polymer and an α-cyclodextrin compound bound to the sample component of interest. As such, in some cases, the sample component can have an extended linear structure which is incorporated within, and projects through, the cavities of multiple α-cyclodextrin moieties. The subject α-cyclodextrin co-polymers provide for desirable spatial arrangements of α-cyclodextrin groups within a co-polymer that provide for selective complexation and capture of sample components of interest. Once the complex is formed it can then be separated from the sample using any convenient method.

In some cases, the target component is a target analyte and the formation of a complex using a subject composition provides for separation of the analyte from the contacted sample. Once the complex has been separated from the contacted sample, the target analyte can be subsequently detected and analyzed.

In certain cases, the target component is a sample component (e.g., a matrix interfering agent) whose presence interferes with the sensitive downstream detection and/or analysis of a target analyte, in such cases, the complex that is formed can be removed from the sample, and can provide for sensitive detection and analysis of a target analyte remaining in the sample.

α-Cyclodextrin compounds of interest that find use in the subject compositions include, but are not limited to, α-cyclodextrin, methyl-α-cyclodextrin, (2-hydroxypropyl)-α-cyclodextrin. In some embodiments, the α-cyclodextrin monomer has the following structure:

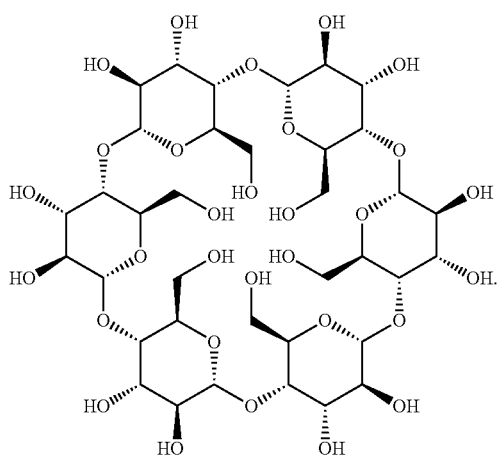 [SMILES: OC[C@H]1O[C@@H]2O[C@H]3[C@@H](O)[C@H](O)[C@@H](O[C@H]4[C@@H](O)[C@H](O)[C@@H](O[C@H]5[C@@H](O)[C@H](O)[C@@H](O[C@H]6[C@@H](O)[C@H](O)[C@@H](O[C@H]7[C@@H](O)[C@H](O)[C@@H](O[C@H]1[C@@H](O)[C@@H]2O)O[C@@H]7CO)O[C@@H]6CO)O[C@@H]5CO)O[C@@H]4CO)O[C@@H]3CO]

In some embodiments, the α-cyclodextrin composition includes at least 5% α-cyclodextrin relative to α-cyclodextrin co-polymer by molarity, such as, inter alia, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, and even 100% α-cyclodextrin relative to α-cyclodextrin co-polymer. In some embodiments, the α-cyclodextrin composition includes at least 50% α-cyclodextrin. In certain instances, the α-cyclodextrin composition includes α-cyclodextrin in the range of 5% to 100% by molarity relative to an optional α-cyclodextrin co-polymer, such as, inter alia, 10% to 100%, 20% to 100%, 30% to 100%, 40% to 100%, 50% to 100%, 60% to 100%, 70% to 100%, 80% to 100%, or 90% to 100%. In certain instances, the α-cyclodextrin composition includes at least 1% α-cyclodextrin co-polymer by molarity. In certain embodiments, the molar ratio of cyclodextrin to cyclodextrin co-polymer in the composition is in the range of 1:1 to 3:1, such as 1:1 to 1:2. In some embodiments, the α-cyclodextrin composition includes a molar ratio of α-cyclodextrin to cyclodextrin co-polymer of about 2:1. In some embodiments, the α-cyclodextrin composition includes no α-cyclodextrin co-polymer.

In some embodiments, the α-cyclodextrin composition includes at least 1% α-cyclodextrin by weight, such as, inter alia, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50% α-cyclodextrin by weight. In some embodiments, the α-cyclodextrin composition includes at least 5% α-cyclodextrin by weight.

The subject composition can further include a variety of additional agents (e.g., as described herein). In some embodiments, the composition includes a β-cyclodextrin or a γ-cyclodextrin. The subject cyclodextrin compositions can further include any convenient additional components, including but not limited to, solvents, buffers, salts, and the like. The subject compositions can be in a liquid or solid form.

α-Cyclodextrin Co-Polymer

As used herein, the term α-cyclodextrin co-polymer refers to a co-polymer having two or more distinct co-monomers, where at least one of the co-monomers is an α-cyclodextrin co-monomer, i.e., a co-monomer that includes an α-cyclodextrin compound, optionally modified, that is suitable for incorporation into the co-polymer. The α-cyclodextrin co-monomers present in the co-polymer define a series repeating α-cyclodextrin groups, which can be included as sidechain groups or can be included as an integral part of the polymeric backbone. The cyclodextrin co-polymer can include α-cyclodextrin co-monomers that are branched. A branched α-cyclodextrin co-monomer includes three or more linking moieties that provide for connection of the co-monomer to three other co-monomer subunits. In such cases, the co-polymer can be dendritic, i.e., have a dendrimer structure.

The cyclodextrin co-polymer can include α-cyclodextrin co-monomers that are functionalized. By functionalized is meant, the α-cyclodextrin co-monomer has been modified to include a group or moiety of interest that provides for a desirable physical or chemical property, such as a specific binding moiety, a water soluble group (WSG), or a detectable moiety (e.g., a fluorophore).

Any convenient polymer chemistries, linkages and co-monomers can be utilized in the preparation of the subject α-cyclodextrin co-polymer. The subject polymers can be prepared via polymerizations that can include radical, anionic, and cationic mechanisms, metal-catalyzed polymerizations such as olefin metathesis, other polymerization reactions known to those of skill in the art, as well as reactions of bifunctional molecules (analogous to the formation of nylon, e.g., reacting molecules each of which bears two or more different reactive moieties that react with each other, but, in some cases, are disfavored from reacting intramolecularly by steric, conformational, or other constraints, or reacting two or more different compounds, each compound bearing two or more reactive moieties that react only with reactive moieties of different compounds, i.e., intermolecularly). Polymer backbone linkages of interest that can be utilized in connecting the co-monomers of the co-polymer include, but are not limited to carbamate, vinyl, ether, acrylate, methacrylate, amide, aramid, ester, urethane, and carbonate. As such, in some cases, the α-cyclodextrin co-polymer can be referred to as a polycarbamate, a polyurethane, a polyacrylate, a polyamide, a polyester, or a polycarbonate, etc. In certain embodiments, the α-cyclodextrin co-polymer is a polyurethane polymer. In some cases, the α-cyclodextrin, co-polymer further includes a β-cyclodextrin or a γ-cyclodextrin co-monomer, where the β-cyclodextrin or a γ-cyclodextrin can be included as a sidechain group or integral to the polymeric backbone.

Any convenient co-monomers can be utilized in the co-polymer in addition to the α-cyclodextrin co-monomer. As used herein, the term "co-monomer precursor" refers to any straight chain or branched, symmetric or asymmetric compound which upon reaction with an α-cyclodextrin monomer precursor links two such moieties together. In certain embodiments, a co-monomer precursor is a compound containing at least two functional groups through which reaction and thus linkage of the α-cyclodextrin co-monomers can be achieved. Examples of functional groups, which can be the same or different, terminal or internal, of each co-monomer precursor include, but are not limited to, amino, acid, imidazole, hydroxyl, thio, acyl halide, —C═C—, or —CC— groups and derivatives thereof. In some embodiments, the two functional groups are the same and are located at termini of the co-monomer precursor. In certain embodiments, a co-monomer precursor contains one or more pendant groups with at least one functional group through which reaction and thus linkage of a moiety of interest can be achieved, or branched polymerization can be achieved. Examples of functional groups, which can be the same or different, terminal or internal, of each co-monomer precursor pendant group include, but are not limited, to amino, acid, imidazole, hydroxyl, thiol, acyl halide, ethylene, ethyne, isocyanate and isothiocyanate groups and derivatives thereof. In certain embodiments, the pendant group is a (un)substituted branched, cyclic or straight chain C1-C10 (in some cases C1-C6) alkyl, or arylalkyl optionally containing one or more heteroatoms, e.g., N, O, S, within the chain or ring.

Upon copolymerization of a co-monomer precursor with an α-cyclodextrin monomer precursor, two α-cyclodextrin monomers can be linked together by joining the primary hydroxyl side of one α-cyclodextrin monomer with the primary hydroxyl side of another α-cyclodextrin monomer, by joining the secondary hydroxyl side of one α-cyclodextrin monomer with the secondary hydroxyl side of another α-cyclodextrin monomer, or by joining the primary hydroxyl side of one α-cyclodextrin monomer with the secondary hydroxyl side of another α-cyclodextrin monomer. Accordingly, combinations of such linkages can exist in the final copolymer. Both the co-monomer precursor and the resulting co-monomer of the final copolymer can be neutral, cationic (e.g., by containing protonated groups such as, for example, quaternary ammonium groups), or anionic (e.g., by containing deprotonated groups, such as, for example, sulfate, phosphate, borinate or carboxylate).

The co-monomers of the co-polymer structure can be described according to the co-monomer precursors from which the co-polymer was prepared. Co-monomer precursors of interest include, but are not limited to (1) 1,4-diisocyanatobutane (DIB), (2) 1,12-diisocyanatododecane (DIDOD), (3) hexamethylene-diisocyanate (HMDI), (4) 1,8-diisocyanatooctane (DIOCT), (5) 4,4'-methylenebis(cyclohexyl-isocyanate) (MBCI), (6) 3,3'-dimethyl-4,4'-Biphenylene-diisocyanate (DMBP), (7) 4,4'-methylenebis(phenyl-isocyanate) (MBPI), (8) tolylene-2,4-diisocyanate (TDI) and (9) 1,4-Phenylene-diisocyanate (PDI) (see e.g., FIG. 1A). For example, a polyurethane co-polymer including a backbone of urethane linkages can be described as having co-monomers derived from an isocyanate or diisocyanate (e.g., via reaction with an alcohol). In some embodiments, the co-polymer includes a co-monomer derived from one of the diisocyanates 1-9 of FIG. 1A.

In some embodiments, the co-polymer includes a co-monomer derived from a diol or a triol, such as a α-cyclodextrin. In certain embodiments, the co-polymer is derived form an α-cyclodextrin co-monomer which can include 2-, 3- and 6-hydroxy groups.

The α-cyclodextrin co-polymer can be of any convenient size. In some cases, the co-polymer has an average MW of 10,000 kDa or more. In some cases, the co-polymer has an average MW of, inter alia, 10,000 kDa or less, such as 9000 kDa or less, 8000 kDa or less, 7000 kDa or less, 6000 kDa or less, 5000 kDa or less, 4000 kDa or less, 3000 kDa or less, 2000 kDa or less, 1000 kDa or less, 900 kDa or less, 800 kDa or less, 700 kDa or less, 600 kDa or less, 500 kDa or less, or even less.

The α-cyclodextrin co-polymers of the present disclosure can be linear, branched or grafted. As used herein, the term "linear α-cyclodextrin co-polymer" refers to a polymer including α-cyclodextrin molecules, or derivatives thereof which are inserted within a polymer chain. As used herein, the term "grafted α-cyclodextrin co-polymer" refers to a polymer comprising α-cyclodextrin molecules, or derivatives thereof which are pendant off of the polymer chain. The term "graft polymer" as used herein refers to a polymer molecule which has additional moieties attached as pendent groups along a polymer backbone. The term "graft polymerization" denotes a polymerization in which a side chain is grafted onto a polymer chain, which side chain consists of one or several other monomers. The properties of the graft copolymer obtained such as, for example, solubility, melting point, water absorption, wettability, mechanical properties, adsorption behavior, etc., deviate more or less sharply from those of the initial polymer as a function of the type and amount of the grafted monomers. As used herein, a branched α-cyclodextrin co-polymer refers to a polymer backbone with a plurality of branch points, wherein each branch point is a starting point of yet another strand of the polymer backbone, and each section of polymer backbone can have a plurality of α-cyclodextrin molecules, or derivatives thereof, inserted into or grafted onto the chain.

The co-polymer can have a variety of different structures, such as a random network structure, a linear structure, a dendritic structure, or a brush polymeric structure. In some cases, the co-polymer has a random network structure. The co-polymer can be composed of particles, such as nano- to micron-scale particles, i.e., particles that have an average diameter in the nanometer scale or in the micrometer scale. The term "particle" as used herein refers to a solid phase such as colloidal particles, microspheres, nanoparticles, or beads. Any convenient methods for generation of such particles can be used. In some cases, the co-polymer has a porous solid structure that can be shaped or molded into any convenient form. In certain instances, the co-polymer is a porous monolithic substrate, for example, a porous solid substrate that is configured as a monolithic chromatography column or as a monolithic filter column.

In some embodiments, the co-polymer is a thin film. The co-polymer can be a film that is configured on the surface of a solid support. The co-polymer can be conjugated to a solid support. Any convenient supports can be utilized in conjunction with the subject co-polymers. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support can be incorporated into a system that provides for separation of a component of interest from a sample assisted by any convenient methods, such as a manually-operated syringe, a centrifuge or an automated liquid handling system. In some cases, the support is a particle that finds use in an automated liquid handling system for the high throughput treatment of samples.

In some embodiments, the α-cyclodextrin co-polymer is described by Formula (I):

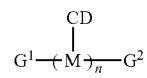  (I)

wherein:
M is a repeating monomeric unit of a polymer;
each CD is an optional α-cyclodextrin;
$G^1$ and $G^2$ are each independently a terminal capping group, a polymer segment, a linker or a linked specific binding member, and
n is an integer from 1 to 10,000.

In some embodiments of Formula (I), each M includes an α-cyclodextrin sidechain group. In some embodiments of Formula (I), the co-polymer includes 10 mol % or more of α-cyclodextrin sidechain groups relative to repeating monomeric units, such as 20 mol % or more, 30 mol % or more, 40 mol % or more, 50 mol % or more, 60 mol % or more, 70 mol % or more, 80 mol % or more, or 90 mol % or more of α-cyclodextrin sidechain groups. In some embodiments of Formula (I), n is an integer from 1 to 1,000, such as an integer from 100 to 1,000. In some embodiments of Formula (I), n is an integer from 10 to 100. In some embodiments of Formula (I), n is an integer from 1,000 to 10,000.

In some instances of Formula (I), $G^1$ and $G^2$ are each independently a terminal capping group. In some instances of Formula (I), $G^1$ and $G^2$ are each independently a terminal capping group, a linker or a linked specific binding member. In some instances of Formula (I), one of $G^1$ and $G^2$ is a linked specific binding member.

In certain instances of Formula (I), M is derived from one of the diisocyanates 1-9 (e.g., as described herein). In certain instances of Formula (I), M is derived from diisocyanate 1 (e.g., as described herein). In certain instances of Formula (I), M is derived from diisocyanate 2 (e.g., as described herein). In certain instances of Formula (I), M is derived from diisocyanate 3 (e.g., as described herein). In certain instances of Formula (I), M is derived from diisocyanate 4 (e.g., as described herein). In certain instances of Formula (I), M is derived from diisocyanate 5 (e.g., as described herein). In certain instances of Formula (I), M is derived from diisocyanate 6 (e.g., as described herein). In certain instances of Formula (I), M is derived from diisocyanate 7 (e.g., as described herein). In certain instances of Formula (I), M is derived from diisocyanate 8 (e.g., as described herein). In certain instances of Formula (I), M is derived from diisocyanate 9 (e.g., as described herein).

Any convenient end groups (e.g., $G^1$ and $G^2$) can be utilized at the terminals of the subject co-polymers. $G^1$ and $G^2$ groups of interest include, but are not limited to a terminal capping group, a polymer segment, a linker and a linked specific binding member. In some embodiments, a terminal capping groups is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In certain cases, the terminal capping group is derived from a monomer used in the method of polymerization, which is capable of undergoing further conjugation. In some instances, $G^1$ and/or $G^2$ is any convenient polymer segment.

In some embodiments, the α-cyclodextrin co-polymer is described by Formula (II):

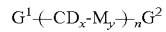  (II)

wherein:
CD is an α-cyclodextrin co-monomer,
M is a second co-monomer (e.g., a co-monomer that lacks an α-cyclodextrin);
x, and y, are each independently an integer from 1 to 1000;
$G^1$ and $G^2$ are each independently a terminal capping group, a polymer segment, a linker or a linked specific binding member, and
n is an integer from 1 to 10,000. In certain instances of Formula (II), the molar ratio of CD to M is in the range of 2:1 to 1:4, such as 1:1 to 1:3, such as 1:1 to 1:2. In certain instances of Formula (II), the molar ratio of CD to M is about 2:1. In certain instances of Formula (II), the molar ratio of CD to M is about 1:1. In certain instances of Formula (II), the molar ratio of CD to M is about 1:3.

In certain instances of Formula (II), the second co-monomer M is derived from one of the diisocyanates 1-9 (e.g., as described herein). In certain instances of Formula (II), the second co-monomer M is derived from diisocyanate 1 (e.g., as described herein). In certain instances of Formula (II), the second co-monomer M is derived from diisocyanate 2 (e.g., as described herein). In certain instances of Formula (II), the second co-monomer M is derived from diisocyanate 3 (e.g., as described herein). In certain instances of Formula (II), the second co-monomer M is derived from diisocyanate 4 (e.g., as described herein). In certain instances of Formula (II), the second co-monomer M is derived from diisocyanate 5 (e.g., as described herein). In certain instances of Formula (II), the second co-monomer M is derived from diisocyanate 6 (e.g., as described herein). In certain instances of Formula (II), the second co-monomer M is derived from diisocyanate 7 (e.g., as described herein). In certain instances of Formula (II), the second co-monomer M is derived from diisocyanate 8 (e.g., as described herein). In certain instances of Formula (II), the second co-monomer M is derived from diisocyanate 9 (e.g., as described herein).

In some instances of Formula (II), x and y are each independently an integer from 1 to 100, such as an integer from 1 to 10. In some instances of Formula (II), x and y are each 1. In some embodiments of Formula (II), n is an integer from 1 to 1,000, such as an integer from 100 to 1,000. In some embodiments of Formula (II), n is an integer from 10 to 100. In some embodiments of Formula (II), n is an integer from 1,000 to 10,000.

In some instances of Formula (II), $G^1$ and $G^2$ are each independently a terminal capping group. In some instances of Formula (II), $G^1$ and $G^2$ are each independently a terminal capping group, a linker or a linked specific binding member. In some instances of Formula (II), one of $G^1$ and $G^2$ is a linked specific binding member.

In some embodiments, the □-cyclodextrin co-polymer is described by Formula (III):

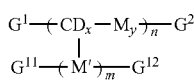
(III)

wherein:
CD is an α-cyclodextrin co-monomer;
M is a second co-monomer
M' is a repeating unit of a polymer;
each x is independently an integer from 1 to 1000;
each y is independently an integer from 1 to 1000;
n is an integer from 1 to 10,000;
$G^1$, $G^2$, $G^{11}$ and $G^{12}$ are each independently a terminal capping group, a polymer segment, a linker or a linked specific binding member; and
m is an integer from 1 to 10,000.

In certain instances of Formula (III), M is derived from one of the diisocyanates 1-9 (e.g., as described herein). In certain instances of Formula (II), M is derived from diisocyanate 1 (e.g., as described herein). In certain instances of Formula (III), M is derived from diisocyanate 2 (e.g., as described herein). In certain instances of Formula (III), M is derived from diisocyanate 3 (e.g., as described herein). In certain instances of Formula (III), M is derived from diisocyanate 4 (e.g., as described herein). In certain instances of Formula (III), M is derived from diisocyanate 5 (e.g., as described herein). In certain instances of Formula (III), M is derived from diisocyanate 6 (e.g., as described herein). In certain instances of Formula (III), M is derived from diisocyanate 7 (e.g., as described herein). In certain instances of Formula (III), M is derived from diisocyanate 8 (e.g., as described herein). In certain instances of Formula (III), M is derived from diisocyanate 9 (e.g., as described herein).

In some instances of Formula (III), x and y are each independently an integer from 1 to 100, such as an integer from 1 to 10. In some instances of Formula (III), x and y are each 1. In some embodiments of Formula (III), n is an integer from 1 to 1,000, such as an integer from 100 to 1,000. In some embodiments of Formula (III), n is an integer from 10 to 100. In some embodiments of Formula (III), n is an integer from 1,000 to 10,000. In some embodiments of Formula (III), m is an integer from 1 to 1,000, such as an integer from 100 to 1,000. In some embodiments of Formula (III), m is an integer from 10 to 100. In some embodiments of Formula (III), m is an integer from 1,000 to 10,000.

In some instances of Formula (III), $G^1$, $G^2$, $G^{11}$ and $G^{12}$ are each independently a terminal capping group. In some instances of Formula (III), $G^1$, $G^2$, $G^{11}$ and $G^{12}$ are each independently a terminal capping group, a linker or a linked specific binding member. In some instances of Formula (III), one of $G^1$ and $G^2$ is a linked specific binding member. In some instances of Formula (III), one of $G^{11}$ and $G^{12}$ is a linked specific binding member.

In some embodiments of Formulae (I)-(III), M is a rigid aryl-containing co-monomer. In certain instances, the rigid aryl-containing co-monomer is derived from a 4,4'-methylenebis(phenyl-isocyanate) co-monomer. In certain embodiments, the cyclodextrin co-polymer includes a molar ratio of α-cyclodextrin co-monomer to methylenebis(phenyl-isocyanate) co-monomer that ranges from 1:3 to 3:1. In certain embodiments, the cyclodextrin co-polymer includes a 1:1 molar ratio of α-cyclodextrin co-monomer to methylenebis(phenyl-isocyanate) co-monomer.

In some embodiments, the α-cyclodextrin co-polymer is described by Formula (IV):

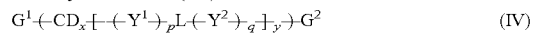
(IV)

wherein:
CD is a cyclodextrin co-monomer selected from an α-cyclodextrin, a β-cyclodextrin, a γ-cyclodextrin and mixtures thereof;
$[(Y^1)_p\text{-L-}(Y^2)_q]$ is a second co-monomer, wherein $Y^1$ and $Y^2$ are each independently selected from the group consisting of an aryl, a substituted aryl, a heteroaryl, a substituted heteroaryl, an alkyl, a substituted alkyl, a heterocycle, a substituted heterocycle, a cycloalkyl and a substituted cycloalkyl; p and q are each independently 0 or 1, wherein p+q≥1; and L is an optional linker:

$G^1$ and $G^2$ are each independently a terminal capping group, a polymer segment, a linker or a linked specific binding member; and x and y are molar ratios of the CD and the $[(Y^1)_p\text{-L-}(Y^2)_q]$ co-monomers in the co-polymer.

In some instances of Formula (IV), x is 10% or more, such as 20% or more, 30% or more, 40% or more, 50% or more, or even more. In some instances of Formula (IV), x is 50% or less, such as 40% or less, 30% or less, 20% or less, 10% or less, or even less.

In certain embodiments of Formula (IV), p and q are both 1, and the $[(Y^1)_p\text{-L-}(Y^2)_q]$ co-monomer is $Y^1\text{-L-}Y^2$. In certain embodiments of Formula (IV), the $[(Y^1)_p\text{-L-}(Y^2)_q]$ co-monomer is derived from a 4,4'-methylenebis(phenyl-isocyanate) (see e.g., diisocyanate 7 below). In certain instances of Formula (IV), $Y^1$ and $Y^2$ are each independently selected from alkyl, cyclohexane, phenyl, methyl-substituted phenyl. In certain instances of Formula (IV), L is absent, a covalent bond or an alkyl linker. In certain cases, L is —$(CH_2)_a$— where a is 1 to 6, such as a is 1.

In some embodiments of Formulae (IV), the $Y^1$ and $Y^2$ are each independently a substituted alkyl. In some embodiments of Formulae (IV), the $Y^1$ and $Y^2$ are each independently a substituted aryl. In some embodiments of Formulae (IV), the $Y^1$ and $Y^2$ are each independently a substituted cycloalkyl. In some embodiments of Formulae (IV), L is a covalent bond. In some embodiments of Formulae (IV), L is —$CH_2$—. In some embodiments of Formulae (IV), L is —$(CH_2)_2$—. In some embodiments of Formulae (IV), the $Y^1$ is a substituted aryl, p is 1, q is 0 and L is absent. In some embodiments of Formulae (IV), the $[(Y^1)_p\text{-L-}(Y^2)_q]$ co-monomer is derived from one of the diisocyanates 1-9 of FIG. 1A.

In some instances of Formula (IV), $G^1$ and $G^2$ are each independently a terminal capping group. In some instances of Formula (IV), $G^1$ and $G^2$ are each independently a terminal capping group, a linker or a linked specific binding member. In some instances of Formula (IV), one of $G^1$ and $G^2$ is a linked specific binding member.

In some embodiments, the α-cyclodextrin co-polymer is described by Formula (V):

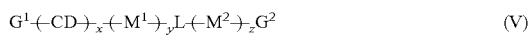

(V)

wherein:

CD is an α-cyclodextrin co-monomer, $M^1$ and $M^2$ are each independently selected from the group consisting of an aryl, a substituted aryl, a heteroaryl, a substituted heteroaryl, an alkyl, a substituted alkyl, a heterocycle, a substituted heterocycle, a cycloalkyl and a substituted cycloalkyl;

L is an optional linker linking $M^1$ and $M^2$;

$G^1$ and $G^2$ are each independently a terminal capping group, a polymer segment, a linker or a linked specific binding member; and x, y and z are the molar ratios of CD, $M^1$ and $M^2$ co-monomers in the co-polymer.

L can be included at any convenient level in the co-polymer of Formula (V).

In some instances of Formula (V), x is 10% or more, such as 20% or more, 30% or more, 40% or more, 50% or more, or even more. In some instances of Formula (V), x is 50% or less, such as 40% or less, 30% or less, 20% or less, 10% or less, or even less.

In some embodiments of Formulae (I)-(V), CD is derived from unmodified α-cyclodextrin.

In some instances of Formula (V), $G^1$ and $G^2$ are each independently a terminal capping group. In some instances of Formula (V), $G^1$ and $G^2$ are each independently a terminal capping group, a linker or a linked specific binding member. In some instances of Formula (V), one of $G^1$ and $G^2$ is a linked specific binding member.

Systems

Aspects of the present disclosure include systems for analytical sample treatment or preparation. The system can include a container having disposed therein an analytical sample preparation composition including an α-cyclodextrin (e.g., as described herein) and/or an α-cyclodextrin co-polymer (e.g., as described herein). In some embodiments of the system, the analytical sample preparation composition includes α-cyclodextrin. In some embodiments of the system, the analytical sample preparation composition includes α-cyclodextrin co-polymer. In some embodiments of the system, the analytical sample preparation composition includes a mixture of α-cyclodextrin and α-cyclodextrin co-polymer. Any of the subject compositions including an α-cyclodextrin co-polymer can be utilized in the systems of the present disclosure as an analytical sample treatment composition.

As used herein, the term "container" refers to a discrete container that can be isolated or can be one of an arrangement of containers (e.g., wells, vials, tubes, pipette tips, etc. in a multi-well tray). In certain embodiments, the system includes two or more containers, such as 6 or more, 12 or more, 24 or more, 48 or more, 96 or more or 384 or more discrete containers. Each container of the system can include the same or different analytical sample treatment composition. Depending on the number of containers in the subject system, the number of analytical sample treatment compositions can vary, as desired, such as two or more, three or more, or four or more and including five or more analytical sample treatment compositions. In some instances, the system includes a plurality of the containers, where at least one of the containers includes an analytical sample treatment composition. The plurality of the containers can be configured as a multiwell plate. In some instances, one or more of the plurality of containers can lack an analytical sample treatment composition, e.g., the container can be empty or include a control composition, and as such can find use as a negative control in any convenient application of interest.

As used herein the terms "multi-well tray" and "multi-well plate" are used interchangeably to refer to a two-dimensional array of containers, e.g., wells, vials, tubes, pipette tips, etc. that can be configured in any convenient format. Multi-well trays of interest include, but are not limited to, a construct including a configuration of wells, tubes and/or vials arranged in a series of rows and columns in a X-Y plane (e.g., 2×3, 2×6, 3×4, 8×12, 16×24), such as 12-well, 24-well, 96-well and 384-well plates or trays of containers.

Systems of interest can include one type of analytical sample treatment composition, where each container can include an aliquot of the composition. In some instances, the system includes a plurality of the containers, each container having disposed therein the analytical sample treatment composition. The containers can be of any convenient size, such as 1 L or less, 500 mL or less, 100 mL or less, 50 mL or less, 10 mL or less, 5 mL or less, 2.0 mL or less, 1.0 mL or less, 500 μL or less, 300 μL or less, 200 μL or less, 100 μL or less or even less. Each container can have disposed therein any convenient amount of an analytical sample treatment composition of interest. In some cases, the analytical sample treatment composition disposed in the container is a dry composition, e.g., a composition that includes no solvent. In preparing the system, a solution of the analytical sample treatment composition can be aliquoted into container(s) of interest before removal the solvent using any convenient means, e.g., by evaporation, lyophilization, etc. In some cases, the analytical sample treatment composition disposed in the container is a liquid.

In some cases, the container includes a filter (e.g., a porous membrane) through which components of a composition which is disposed therein can be passed, e.g., by application of positive or negative pressure, by centrifugation, by gravity filtration. In some cases, the container is a filter tube. Any convenient filters and membrane types can be incorporated into the subject containers. Filters of interest include, but are not limited to, size exclusion filters, lipid retaining filters, chromatography supports, affinity filters, affinity supports, and the like. In some cases, container includes a lipid retaining membrane. Any convenient materials can find use in the subject containers to provide for filtering of the components of a sample disposed therein, such as CPG, $C_8$, C18, carbon, affinity chromatography supports, and the like. Any filtering means can be utilized, such as filters from Millipore, Porex, Advantec, and the like, so long as the pore size utilized is appropriate for the application. Similarly, filters of polypropylene, PVDF, PTFE, nitrocellulose, regenerated cellulose, etc., can be utilized, as desired for particular applications.

In some cases, the filter provides for retention of the α-cyclodextrin co-polymer of the subject composition inside the container, while allowing passage of sample components of interest from through the sample. In certain cases, the subject composition can itself be disposed in, or a part of, the filter of the container to provide for removal of a sample component of interest. In some cases, the porous membrane includes the α-cyclodextrin co-polymer.

Kits

Also provided by the present disclosure are kits for practicing the subject methods, as described herein. The subject kits at least include an α-cyclodextrin composition which can include an α-cyclodextrin, an α-cyclodextrin co-polymer or a mixture of α-cyclodextrin and α-cyclodextrin co-polymer. In some embodiments of the kit, the kit includes two distinct α-cyclodextrin compositions, such as a first component including an α-cyclodextrin, and a second component including an α-cyclodextrin co-polymer. As discussed herein, the subject composition can be provided as a system disposed in a single container or disposed in an array of containers. Other optional components of the kit include, but are not limited to QuEChERS extraction salts, an analyte extraction solvent, a quantitation standard, a porous membrane filer and a precipitation solvent.

The various components of the kit can be present in separate containers or certain compatible components can be pre-combined into a single container, as desired. The subject kits can also include one or more other reagents for preparing or processing an analyte sample. The reagents can include one or more matrices, solvents, sample preparation reagents, buffers, desalting reagents, enzymatic agents, denaturing reagents, where calibration standards such as positive and negative controls can be provided as well. As such, the kits can include one or more containers such as vials or bottles, with each container containing a separate component for carrying out a sample processing or preparing step and/or for carrying out one or more steps of a sample preparation and analysis protocol. In addition, the kits can also include one or more control analyte mixtures, e.g., two or more control samples for use in testing the kit.

In addition to above-mentioned components, the subject kits can further include instructions for using the components of the kit to practice the subject methods, i.e., to prepare a sample and/or assess a sample. The instructions for practicing the subject methods are generally recorded on a suitable recording medium. For example, the instructions can be printed on a substrate, such as paper or plastic, etc. As such, the instructions can be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods

Aspects of the present disclosure include methods of extracting a component of interest from a sample. The method can include contacting a sample with an α-cyclodextrin composition (e.g., as described herein) to produce an α-cyclodextrin complex of a target component. The α-cyclodextrin complex is a complex of the α-cyclodextrin groups(s) of the co-polymer and the target component of the sample that can further include one or more bound α-cyclodextrin compounds (e.g., as described herein).

Any convenient methods of sample preparation, cleanup and analysis can be adapted to include the subject methods and compositions. Methods of interest include, but are not limited to, those methods for reducing matrix effects described in U.S. Pat. No. 7,999,084, the disclosure of which is herein incorporated by reference, QuEChERS protocols, and protein precipitation methods.

In certain cases, the target component is a component that is desirable to remove from the sample (e.g., a matrix interfering agent). Removal of the target component from the sample produces a contacted sample that can include a target analyte that is to be analyzed. As such, in some cases the method is a method of reducing matrix effects in an analytical sample. In some cases, the presence of the target component in the sample can have a deleterious effect on the analysis of the target analyte and removal of the target component provides for an improved analysis of the target analyte. The analytical sample (e.g., as described herein) can be one that includes a matrix-interfering agent and an analyte.

As used herein, the term "matrix interfering agent" refers to any substance present in an analytical sample that causes matrix effects, that is, interferes with quantitation of an analyte, or results in accumulation, contamination and/or degradation to the analytical system. Matrix interfering agents commonly suppress the ionization of a particular analyte present in the sample during electrospray ionization for mass spectrometric analysis. The relative abundance of the analyte can be underrepresented and/or underestimated or overrepresented relative to its true abundance in the sample due to matrix effects. Any convenient matrix-interfering agent that is present in the sample can be selected for removal via the subject methods. Matrix interfering agents of interest include, but are not limited to, lipids (such as cholesterol, triglycerides, phospholipids, lysophospholipids, lipoproteins), surfactants, excipients, polyethylene glycol (PEG), disintegrants and dosing agents. In some embodiments, the lipids are phospholipids. In certain instances, the surfactants are selected from anionic surfactants or nonionic surfactants. In some cases, the surfactants include a hydrocarbon chain which can be advantageously complexed using the α-cyclodextrin compositions described herein. The method can include contacting the analytical sample with an α-cyclodextrin composition (e.g., as described herein) to produce a contacted sample including a matrix-cyclodextrin complex. In some cases, the matrix-interfering agent is a lipid and the complex comprises a lipid-α-cyclodextrin complex.

Surfactants that can be removed using the presently described devices and methods include a wide variety of surfactants, including nonionic surfactants as well as ionic surfactants, including cationic surfactants, anionic surfactants or zwitterionic surfactants. Nonionic surfactants include, for example, polyoxyl stearates such as polyoxyl 40 stearate, polyoxyl 50 stearate, polyoxyl 100 stearate, polyoxyl 12 distearate, polyoxyl 32 distearate, and polyoxyl 150 distearate, and other Myrj™ series of surfactants, triblock co-polymers of ethylene oxide/propylene oxide/ethylene oxide, also known as poloxamers, having the general formula $HO(C_2H_4O)_a(—C_3H_6O)_b(C_2H_4O)_aH_4$, available under the tradenames Pluronic and Poloxamer, sugar ester surfactants, sorbitan fatty acid esters such as sorbitan monolaurate, sorbitan monopalmitate, sorbitan monostearate, sorbitan tristearate, and other Span™ series surfactants, glycerol fatty acid esters such as glycerol monostearate, polyoxyethylene derivatives such as polyoxyethylene ethers of high molecular weight aliphatic alcohols (e.g., Brij 30, 35, 58, 78 and 99) polyoxyethylene stearate (self emulsifying), polyoxyethylene 40 sorbitol lanolin derivative, polyoxyethylene 75 sorbitol lanolin derivative, polyoxyethylene 6 sorbitol beeswax derivative, polyoxyethylene 20 sorbitol beeswax derivative, polyoxyethylene 20 sorbitol lanolin derivative, polyoxyethylene 50 sorbitol lanolin derivative, polyoxyethylene 23 lauryl ether, polyoxyethylene 2 cetyl ether with butylated hydroxyanisole, polyoxyethylene 10 cetyl ether, polyoxyethylene 20 cetyl ether, polyoxyethylene 2 stearyl ether, polyoxyethylene 10 stearyl ether, polyoxyethylene 20 stearyl ether, polyoxyethylene 21 stearyl ether, polyoxyethylene 20 oleyl ether, polyoxyethylene 40 stearate, polyoxyethylene 50 stearate, polyoxyethylene 100 stearate, polyoxyethylene derivatives of fatty acid esters of sorbitan such as polyoxyethylene 4 sorbitan monostearate, polyoxyethylene 20 sorbitan tristearate, and other Tween™ series of surfactants, phospholipids and phospholipid fatty acid derivatives such as fatty amine oxides, fatty acid alkanolamides, propylene glycol monoesters and monoglycerides, such as hydrogenated palm oil monoglyceride, hydrogenated soybean oil monoglyceride, hydrogenated palm stearine monoglyceride, hydrogenated vegetable monoglyceride, hydrogenated cottonseed oil monoglyceride, refined palm oil monoglyceride, partially hydrogenated soybean oil monoglyceride, cotton seed oil monoglyceride sunflower oil monoglyceride, sunflower oil monoglyceride, canola oil monoglyceride, succinylated monoglycerides, acetylated monoglyceride, acetylated hydrogenated vegetable oil monoglyceride, acetylated hydrogenated coconut oil monoglyceride, acetylated hydrogenated soybean oil monoglyceride, glycerol monostearate, monoglycerides with hydrogenated soybean oil, monoglycerides with hydrogenated palm oil, succinylated monoglycerides and monoglycerides, monoglycerides and rapeseed oil, monoglycerides and cottonseed oils, monoglycerides with propylene glycol monoester sodium stearoyl lactylate silicon dioxide, diglycerides, triglycerides, polyoxyethylene steroidal esters, Triton-X series of surfactants produced from octylphenol polymerized with ethylene oxide, where the number "100" in the trade name is indirectly related to the number of ethylene oxide units in the structure, (e.g., Triton X-100™ has an average of N=9.5 ethylene oxide units per molecule, with an average molecular weight of 625) and having lower and higher mole adducts present in lesser amounts in commercial products, as well as compounds having a similar structure to Triton X-100™, including Igepal CA-630™ and Nonidet P-40M (NP-40™, N-lauroylsarcosine. Sigma Chemical Co., St. Louis, Mo.), and the like. Any hydrocarbon chains in the surfactant molecules can be saturated or unsaturated, hydrogenated or unhydrogenated. Sugar ester surfactants include sugar fatty acid monoesters, sugar fatty acid diesters, triesters, tetraesters, or mixtures thereof.

In some cases, the target component of the sample that is extracted using the subject compositions can be a target analyte that is to be analyzed. Complexation of the target analyte by the α-cyclodextrin composition allows for separation of the target analyte from the matrix of the sample (e.g., as described herein) and can provide for an improved analysis of the target analyte. In such cases, the target analyte can be subsequently dissociated from the complex, prior to detection.

Any convenient sample can be treated according to the subject methods. The term "sample" as used herein relates to a material or mixture of materials, in some cases, although not necessarily, in fluid, i.e., aqueous, form, containing one or more components of interest. Samples can be derived from a variety of sources such as from food stuffs, environmental materials, a biological sample or solid, such as tissue or fluid isolated from an individual. The term "biological sample" is used herein to refer to a whole organism, plant, fungi or a subset of animal tissues, cells or component parts which can in certain instances be found in blood, mucus, lymphatic fluid, synovial fluid, cerebrospinal fluid, saliva, amniotic fluid, amniotic cord blood, urine, vaginal fluid and semen. As such, a "biological sample" used herein can refer to a homogenate, lysate or extract prepared from a whole organism or a subset of its tissues, including but not limited to, for example, plasma, serum, spinal fluid, lymph fluid, the external sections of the skin, respiratory, intestinal, and genitourinary tracts, tears, saliva, milk, blood cells, tumors, organs. In embodiments of the invention, a "biological sample" will contain cells from the animal, plants, bacteria or fungi. A "biological sample" can also refer to a medium, such as a nutrient broth or gel in which an organism has been propagated, which contains cells as well as cellular components, such as proteins or nucleic acid molecules. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

In some cases, one or more preparatory steps are performed on the sample before the sample is treated according to the subject methods, such as any convenient combination of liquid phase extraction, solid phase extraction, filtration, centrifugation, dilution or concentration steps. In certain instances, the sample is a liquid extract of a sample of interest, such as a food sample, an environmental sample or a biological sample. In some cases, the sample is a QuEChERS extract.

In general terms, the QuEChERS extraction protocol can consist of three simple steps. A sample (ground solid or liquid) is added to a centrifuge tube. The extraction step (Step 1) involves the addition of acetonitrile and in some cases water to the sample that is spiked with QC and internal standards. Then, salts are added to induce partitioning of the acetonitrile and aqueous phases. The mixture is mixed/shaken. The clean-up step (Step 2) involves the transfer of the acetonitrile layer containing sample coextractives and analytes of interest to a tube containing the Dispersive Solid Phase Extraction (dSPE) materials. These materials remove unwanted coextractives and typically include C18, graphitized carbon black (GCB), zirconia, primary/secondary amine (PSA) or in the case of this invention, α-CD or copolymers. The resulting slurry is mixed and centrifuged. The final step (Step 3) is the LC chromatographic separation and quantitation of the sample components in the supernatant.

Additional sample clean up can be required for some applications such as GC. If so, the supernatant from the dSPE can be transferred to a tube containing additional inorganic salts. The slurry is mixed and centrifuged. The supernatant resulting from the second cleaning step is then separated and quantitated by the chromatographic method.

Protein precipitation consists of addition of acetonitrile and/or methanol to the sample to precipitate the unwanted proteins. The precipitate can be removed by filtration or centrifugation. Filtration is accomplished by passing through small porosity filters and in some cases, sorbent materials to remove unwanted coextractives.

Components in a sample that are of interest for downstream detection and/or analysis can be termed "analytes". In some embodiments, the sample is a complex sample containing at least about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $10_9$, $10^{10}$, $10^{11}$, $10^{12}$ or more species of analyte. The term "analyte" refers to a known or unknown component of a sample. In some cases, analytes are biopolymers, i.e., an oligomer or polymer such as an oligonucleotide, a peptide, a polypeptide, an antibody, or the like. In some cases, an analyte is a small (e.g., 1000 Da or less, such as 500 Da or less) organic compound, such as an environmental pollutant, e.g., a pesticide or a drug.

Once the α-cyclodextrin complex of the target component has been produced, the complex can be separated from the sample using any convenient methods, including but not limited to, precipitation, extraction, and affinity chromatography. In some cases, the α-cyclodextrin complex precipitates in the contacted sample upon formation and can be subsequently separated using any convenient method, e.g., via filtration or centrifugation. Any desirable solvents can be selected to be utilized in, or added to, the sample to provide for the precipitation of the α-cyclodextrin complex. Precipitation depends on a variety of factors, such as the solubilities of the α-cyclodextrin composition, the target components of the sample and the complex. In certain instances, the α-cyclodextrin complex is separated via liquid extraction. In some cases, the α-cyclodextrin complex is separated via solid phase extraction.

The contacting step can be performed by adding an amount of α-cyclodextrin composition effective to complex all of the target component (e.g., a target analyte or matrix interfering agents) in a sample. The α-cyclodextrin composition can be added to the sample as a solution in any convenient solvent. The α-cyclodextrin composition can be added to the sample as a solid composition. The contacting can be performed for any convenient period of time, e.g., from about 10 seconds to about 60 minutes, such as from about 10 seconds to about 10 minutes, e.g., for about 1 minute, about 2 minutes, about 5 minutes, or about 10 minutes.

Contacting the sample with the α-cyclodextrin composition can include mixing. Any convenient method can be employed to stir the sample with the α-cyclodextrin composition. Mixing can include, for example stirring with a magnetic stir bar or manually stirred using any convenient stirring apparatus. Alternatively, the sample can be stirred by vortexing the contacted sample, shaking the contacted sample such as with a mechanical shaker or shaking can be manually performed (i.e., by hand). In some instances, mixing the sample with the α-cyclodextrin composition includes sonicating the contacted sample.

The cyclodextrin complex that is produced can be separated from the contacted sample in a variety of ways. In some cases, the cyclodextrin complex is insoluble in the contacted sample solution and precipitates. The complex precipitate can then be separated, e.g., by filtration, centrifugation and the like. In certain cases, the matrix-cyclodextrin composition is soluble in the contacted sample, but can be separated via liquid phase extraction or solid phase extraction. As such, in some cases, the sample can be contacted with an extraction solvent to produce a sample extract, and the separating includes separating the complex from the sample extract via liquid phase extraction.

In some cases, the α-cyclodextrin composition includes an α-cyclodextrin co-polymer immobilized in a porous membrane. In such cases, the contacting can include eluting the sample through the porous membrane. The separating step can include filtering the sample through the porous membrane. The complex can separated from the contacted sample via immobilization on a chromatography column or porous membrane.

In certain cases, the sample is a biological sample and the contacting step can also lead to precipitation of non-complexing components. The sample can include protein components which do not complex the α-cyclodextrin composition. In some cases, the separating step further includes filtering precipitated proteins from the contacted sample. In some embodiments, a sample is subjected to a protein precipitation treatment followed by centrifugation, or does not contain sufficient protein to warrant removal prior to analysis, and subsequently is treated with the α-cyclodextrin composition with selectivity for matrix interfering agents. In some cases, the supernatant is transferred from the protein pellet using a pipette tip or a filter tube loaded with the α-cyclodextrin composition.

The methods can further include optionally washing the cyclodextrin complex (e.g., precipitate) with a wash solvent or mixture of solvents to remove unbound components. In some cases, the methods can further include eluting components from the cyclodextrin complex with eluting solvents to release the bound components from the complex.

In some instances, separation of the complex from the contacted sample produces a matrix-reduced composition that includes a reduced amount of matrix interfering components relative to the original analytical sample.

In some embodiments, the α-cyclodextrin composition binds at least 50% of the target matrix interfering agent(s) present in the analytical sample (such as, inter alia, at least 60%, at least 70%, at least 80/%, at least 90%, at least 95%, at least 98%, at least 99%, at least 99.5%, at least 99.9%). In some embodiments, the subject methods provide recovery of at least 80% of the analyte(s) in the contacted sample, such as, inter alia, at least 85%, at least 90%, at least 91%, at least 92%, at least 93%, at least 94%, at least 95%, at least 96%, at least 97%, at least 98%, at least 99%, at least 99.5%, at least 99.9%, relative to a control sample. In some embodiments of the subject methods, the α-cyclodextrin composition includes at least 5% α-cyclodextrin relative to α-cyclodextrin co-polymer by molarity (e.g., inter alia, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% α-cyclodextrin relative to α-cyclodextrin co-polymer) and provides for recovery of at least 80% of the analyte(s) in the contacted sample, such as, inter alia, at least 85%, at least 90%, at least 91%, at least 92%, at least 93%, at least 94%, at least 95%, at least 96%, at least 97%, at least 98%, at least 99%, at least 99.5%, at least 99.9%, relative to a control sample.

In some cases, the method produces a contacted sample that is substantially free from target matrix interfering agent(s). By substantially free from target matrix interfering agent(s) is meant a solution that includes 0.5% or less by weight of the ionic liquid, such as, inter alia, 0.1% or less by weight, 0.03% or less by weight, 0.01% or less by weight, 0.003% or less by weight, 0.001% or less by weight, 0.0003% or less by weight, or 0.0001% or less by weight.

Aspects of the methods include detecting a target analyte. In some cases, where the matrix interfering agents are separated from the contacted sample, the detecting includes detecting the analyte in the matrix-reduced composition that is produced. In such cases, the matrix-reduced composition has a reduced deleterious effect on the detecting the analyte. A deleterious effect refers to an undesirable reduction in the accuracy of detection, that can occur by the action of matrix interfering agents during sample preparation and/or sample analysis, e.g., by reducing the sensitivity of detector, or by undesirable removal of target analyte from the analytical sample during sample preparation. As used herein, a "reduced deleterious effect" refers to an improvement in the accuracy of analyte detection and/or quantitation, and can be determined via an improvement in one or more measures such as detection limit, signal to noise ratio, reproducibility, sensitivity, limits of quantitation, limits of detection, e.g., relative to a control sample. Any convenient methods of detecting the analyte can be used, in some cases, analyses include chromatographic, spectrophotometric, mass spectrometric, and the like, and combinations thereof. Methods of interest include, but are not limited to mass spectrometry, LC/MS-MS, and UV/vis spectroscopy.

The method can further include quantitating the amount of analyte in the sample. In some cases, the amount of analyte in the matrix-reduced composition and the amount of analyte in the sample are the same. By practicing the subject methods, the matrix interfering agent(s) can be separated from the sample without the simultaneous undesirable removal of target analyte. Separation of the matrix interfering agent(s) can provide a matrix-reduced composition that has reduced matrix effects during subsequent quantitation of the target analyte.

Mass Spectroscopic Analysis

Accordingly, the analytes and sample produced using the subject methods can be evaluated using mass spectrometry or liquid chromatography-mass spectrometry (LC-MS). The analytes can be directly analyzed. In some cases, the analyte is a protein and, the analyte can be digested into fragments prior to analysis. In some instance, the analyte is a small organic molecule, e.g., a pesticide. Accordingly, the subject analytes can be intact or fragmented (i.e., digested with an enzyme) prior to their analysis in a mass spectrometer. Prior to their analysis in a mass spectrometer, the analytical sample can also under liquid chromatography (LC). Any convenient LC methods and columns can be utilized in combination with the mass spectroscopic analysis described herein.

The samples can be analyzed using any mass spectrometer that has the capability of measuring analyte masses with high mass accuracy, precision, and resolution. Accordingly, the isolated analytes can be analyzed by any one of a number of mass spectrometry methods, including, but not limited to, electrospray mass spectrometry, matrix-assisted laser desorption ionization time-of-flight mass spectrometry (MALDI-TOF) and any tandem MS such as QTOF, TOF-TOF, etc.). Mass spectrometry methods are generally well known in the art. The basic processes associated with a mass spectrometry method are the generation of gas-phase ions derived from the sample, and the measurement of their mass.

In certain embodiments, the masses of ions produced by the analytes of interest in a sample can be calculated by methods known in the art, e.g., techniques such as selective ion monitoring (SIM) can be employed to monitor only those ions that correspond to the analytes of interest. The output from the mass spectrometry analysis can contain the masses, i.e., the molecular weights, of the isolated analytes or fragments thereof, and their relative or absolute abundances in the sample. The analyte masses obtained from mass spectrometry analysis can be compared to those expected for the analytes. By performing this comparison, any signals obtained that are not derived from the analytes of interest can be discarded, and only those signals corresponding to the pre-determined analytes can be retained. In certain embodiments, the masses of the analytes or fragments thereof are stored in a table of a database and the table usually contains at least two fields, one field containing molecular mass information, and the other field containing analyte identifiers, such as names or codes. As such, the subject methods can involve comparing data obtained from mass spectrometry to a database to identify data for an analyte of interest.

In general, methods of comparing data produced by mass spectrometry to databases of molecular mass information to facilitate data analysis is very well known in the art and, as such, need not be described here in any further detail. Accordingly, information, e.g., data, regarding the amount of analytes in a sample of interest (including information on their presence or absence) can be obtained using mass spectrometry.

For each analyte, information obtained using mass spectrometry can be qualitative (e.g., showing the presence or absence of an analyte, or whether the analyte is present at a greater or lower amount than a control analyte or other standard) or quantitative (e.g., providing a numeral or fraction that can be absolute or relative to a control analyte or other standard). Standards for assessing mass spectrometry data can be obtained from a control analyte that is present in a sample, such as an analyte of known concentration, or an analyte that has been added at a known amount to the sample, e.g., a spiked analyte. Accordingly, the data produced by the subject methods can be "normalized" to an internal control, e.g. an analyte of known concentration or the like. By comparing the results from assessing the presence of an analyte in two or more different samples using the methods set forth above, the relative levels of an analyte in two or more different samples can be obtained. In other embodiments, by assessing the presence of at least two different analytes in a single sample, the relative levels of the analytes in the sample can be obtained.

Utility

The subject compositions, systems, kits and methods can be employed in a variety of diagnostic, analytical and research applications. The subject compositions and methods find use in any applications where the complexation and separation of a target component of a sample is desirable, e.g., to provide a sample of interest that lacks the target component, or to provide an isolated target component of interest.

In some cases, the subject methods find use in the removal of undesirable components from analytical samples, including components that interfere with the detection and analysis of target analytes in the sample. For example, the subject compositions and methods find use in the cleanup of samples by removing matrix components such as lipids during, e.g., QuEChERS protocols of food and agricultural samples, following protein precipitation of biological samples, or extraction using dispersive solid phase extraction (dSPE).

EXAMPLES

Example 1: Preparation of α-Cyclodextrin Co-Polymer Compositions

The incorporation of cyclodextrins (CDs) into polymeric materials has been shown to preserve the CDs ability to form inclusion complexes with a wide variety of molecules. Cyclodextrin-based polymers can be prepared via a variety of methods. For example, the functionalization of cyclodextrins with acrylate groups via established "click" chemistry reactions can be used to synthesize from standard radical initiators polymers which incorporate CDs as pendant groups. The copolymerization of cyclodextrins with epichlorohydrin under highly basic conditions using 50% sodium hydroxide is another technique to form CD-based polymers. This technique can be used to synthesize high molecular weight polymers and has the advantage of utilizing unfunctionalized cyclodextrin as a starting material, but this method requires very high cross-linker/CD ratios (>30:1) in order to yield water-insoluble polymers. Additionally, the copolymerization of cyclodextrins with various dianhydride monomers can produce high molecular weight, water insoluble polymers using a relatively easy reaction. However, this method results in ring opening of the cyclic anhydride and the formation of undesired carboxylic acid functional groups. The high concentration of acid groups throughout the resulting polymer can adversely affect both the selectivity and solubility characteristics of the resulting polymers depending on the desired application.

A more useful strategy for the formation of cyclodextrin-based polymers utilizes the reaction of unfunctionalized cyclodextrins with a variety of diisocyanate monomers (FIG. 1). Isocyanate groups (R—N=C=O) are strong electrophiles which react under mild conditions with a variety of nucleophiles such as alcohols or amines. Specifically, the reaction between an isocyanate and a hydroxyl group (R—OH) yields a carbamate or urethane linkage (R—OC(O)N(H)—R' where R and R' can be alkyl or aryl groups). Reaction mixtures containing monomers incorporating two or more hydroxyls groups (polyols) and cross-linker molecules containing two or more isocyanate groups, can result in chain growth via urethane linkages, resulting in a class of polymers known as "polyurethanes". One method for the synthesis of polyurethanes makes use of the reaction of diisocyanates with polyols. Cyclodextrins can be considered a type of "cyclic polyol", and can react with diisocyanate monomers to form cyclodextrin-based polyurethane polymers.

The formation of cyclodextrin-based urethane polymers has several advantages for the synthesis of CD-based polymers. Since the technique makes use of the reaction between diisocyanate monomers and CD hydroxyl groups, the polymerization occurs in a single step or "one pot" synthesis, eliminating the need for additional steps involving CD functionalization. In addition, the reaction between isocyanates and cyclodextrins occurs under mild conditions requiring short reaction times. Reaction time is a key variable that can be manipulated in order to control the molecular weight of the final polymer. The polymerization of cyclodextrins with diisocyanates can be performed at elevated temperatures (60° C.), which increases the reaction kinetics and drives the polymerization to completion; increasing the molecular weight and yield of the resulting CD polyurethane polymer. Cyclodextrins and diisocyanate monomers can also be polymerized under ambient conditions for shortened durations to yield lower molecular weight or oligomeric CD-polyurethanes which display increased solubility in organic solvents. Two-component polyurethane systems can be cured at low temperatures and easily controlled. The properties of the resulting polyurethanes are largely determined by the isocyanate monomers used in the synthesis. Long, flexible isocyanates can be used to synthesize elastic polymers, while planar or rigid aromatic isocyanates yield tougher and more rigid polymers.

For applications of interest involving selective lipid removal following a QuEChERS extraction, protein precipitation, or functional filtration, the desired properties for synthesized cyclodextrin-based polymers include:

1. Incorporation of an α-cyclodextrin, which is selective for hydrophobic lipid molecules due to its small cavity size of 4.4 Å, to provide encapsulation for aliphatic compounds and other appropriately shaped guest molecules while leaving analytes in solution for further analysis;

2. Hydrophilicity, but with low solubility in water or water/acetonitrile mixtures, so as to efficiently extract and separate lipids from common solvents;

3. A high surface area and porosity to increase the absorption activity of the material;

4. A high CD content relative to crosslinker concentration to increase the selective activity for lipid absorption of the polymer while minimizing secondary interactions with analyte; and 5. High polymer purity so no residual chemicals from the polymerization process are introduced into analyte solution.

General Synthesis of Diisocyanate α-Cyclodextrin Co-Polymer

The methods of Bhaskar et al., "β-Cyclodextrin-polyurethane polymer as solid phase extraction material for the analysis of carcinogenic aromatic amines", Analytica Chimica Acta. 2004, 509, 39; and Wilson et al., "Surface area and pore structure properties of urethane-based copolymers containing β-cyclodextrin", Journal of Colloid and Interface Science, 2011, 357, 215 are adapted in the preparation of the subject α-cyclodextrin co-polymers.

The following is a general procedure that can be extended to any convenient diisocyanate monomers. 5.000 g of α-cyclodextrin (5.14 mmol) is placed in a flask along with a small stir bar. The flask is heated overnight to 140° C. under vacuum to dehydrate the cyclodextrin and glass flask. This step is necessary to remove encapsulated water within the cyclodextrin cavities (e.g., up to 6 water molecules per cavity) which can adversely react with isocyanate groups.

The α-CD is transferred to a nitrogen line and purged with a continuous stream of nitrogen gas. To the flask containing the dehydrated cyclodextrin is then added 50 ml of anhydrous dimethylformamide (DMF). The mixture is stirred vigorously under a nitrogen purge until the cyclodextrin fully dissolves. Once dissolved, n molar equivalents (e.g., where n=1, 2, 3 . . . ) of diisocyanate monomer is then added to the stirring solution under a continuous nitrogen purge. The reaction flask is then purged with nitrogen gas to remove any residual atmospheric contaminants. The flask is then sealed under a positive pressure of nitrogen and allowed to react at a designated temperature (25-60° C.) for a known amount of time (3-24 hours). Once complete, the DMF mixture is added drop-wise to 500 ml of vigorously stirring methanol or water in order to precipitate the resulting polymer. Addition of the DMF reaction solution to a non-solvent typically yields very fine, low-density, white powders suspended in the solvent. The polymer slurry is centrifuged at 5000 rpm for 10 min, followed by decantation of the liquid. The solid is washed six times with water/methanol/centrifuge cycles. As an additional purification step, the polymer is also extensively washed using methanol extraction in a Soxhlet apparatus for 1-2 days to remove low molecular weight and small molecule impurities. The final product is then dried under vacuum overnight at 40° C. to remove solvent contained in the final product. In some cases, yields for these polymers ranged from 60-70%. Additional diisocyanate monomers utilized with this procedure also included 1,12-diisocyanatododecane and 4,4'methylenebis (cyclohexyl isocyanate).

Figure 9:
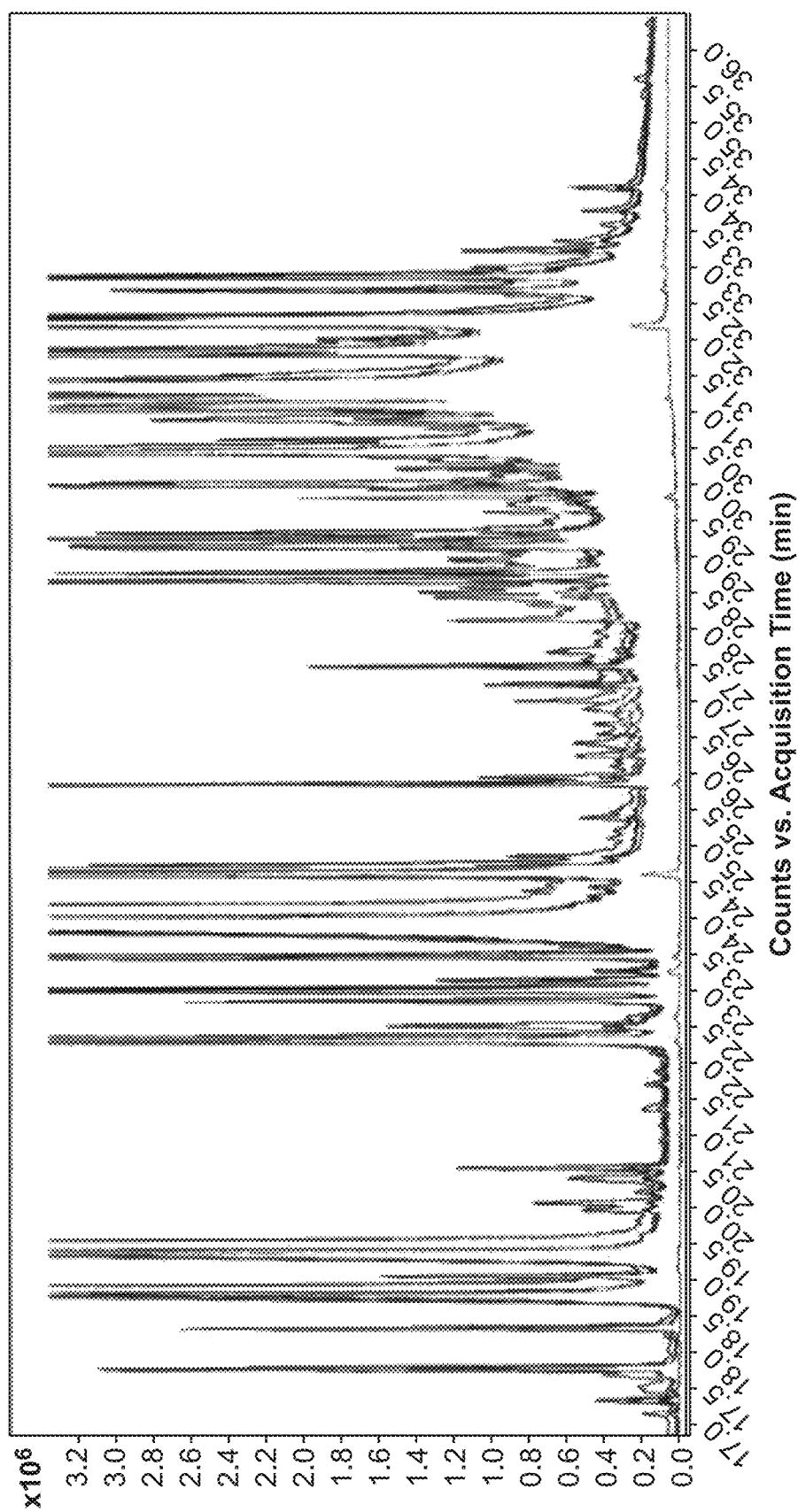
FIG. 9 shows overlaid GC-MS chromatograms (from top to bottom) for untreated avocado, after treatment with 1:1 HMDI-α-CD in 1:1 acetonitrile/H$_2$O, treatment with 2:1 HDMI-α-CD in 1:1 acetonitrile/H$_2$O, treatment with 2:1 HDMI-α-CD in 4:1 acetonitrile/H$_2$O, and treatment with α-CD in water.
Figure 10:
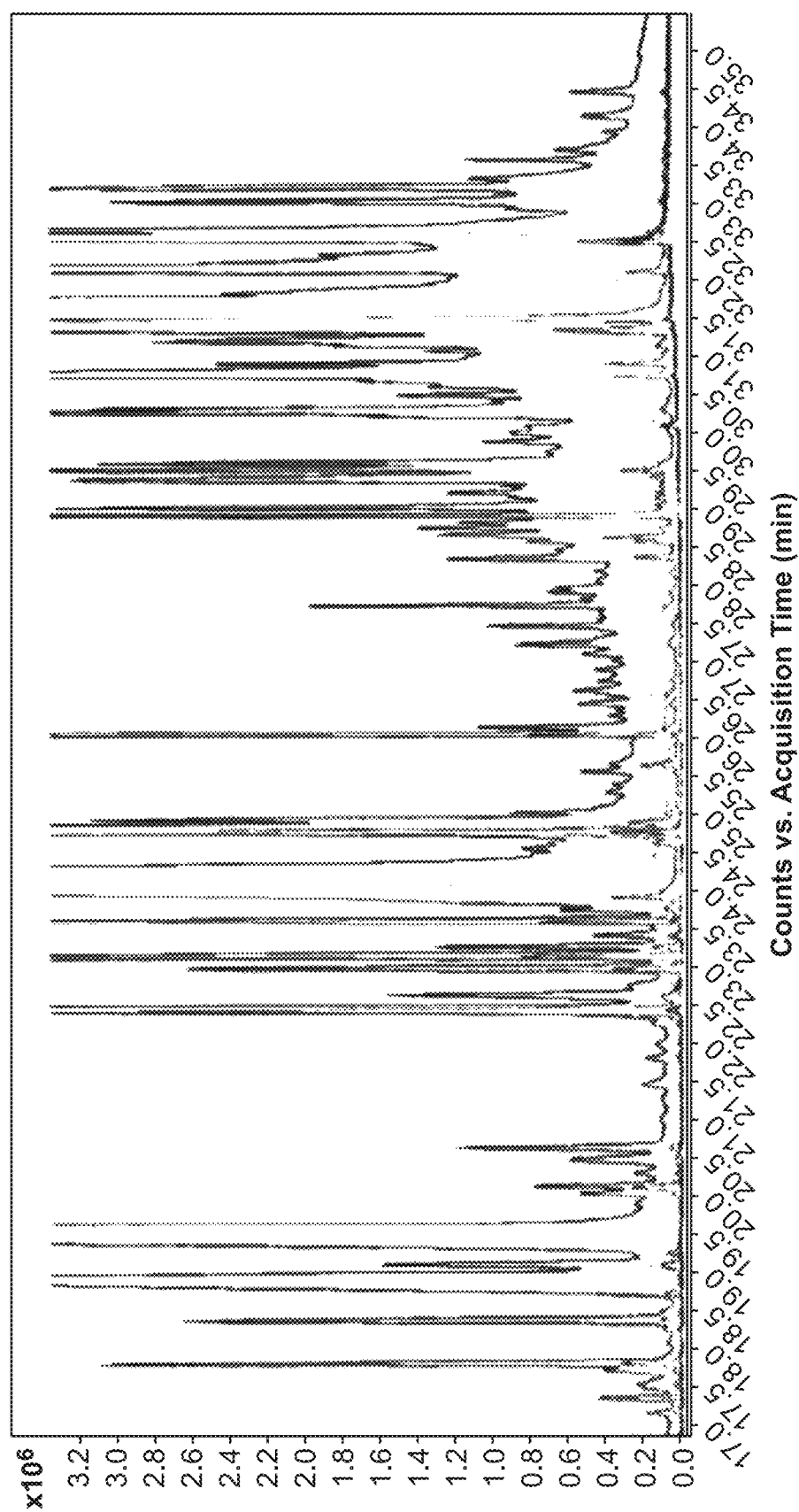
FIG. 10 shows GC-MS chromatogram overlays (from top to bottom) of untreated avocado, after treatment with 3:1 MBPI-α-CD, after treatment with 1:1 MBPI-α-CD, and after treatment with α-CD solution.

The performance of the α-cyclodextrin polyurethanes was optimized for lipid extraction by examining several important processing parameters. A low crosslinker density provided a higher concentration of cyclodextrin molecules available within the material and led to improved lipid removal (FIG. 10, as described herein). In addition, the structure of the diisocyanate monomer was also found to influence overall performance of the synthesized materials. Linear aliphatic diisocyanates such as hexamethylene diisocyanate (HMDI) or 1,12-diisocyanatododecane (DIDOD) consistently showed results as indicated in FIG. 9 compared to polymers incorporating the more rigid methylenebis(phenyl-isocyanate) (MBPI). A final parameter expected to play a role in the performance of α-cyclodextrin polyurethanes for lipid extraction is molecular weight of the material; a property controlled by reaction time, concentration, and temperature. Conditions used in the first generation of our synthesized polymers made use of elevated temperatures of 60° C. and long reaction times approaching 24 hrs. These conditions were originally chosen to drive the polymerization to completion and increase the yield of the polyurethane. However, high molecular weight polymers lead to the matrix removal results as shown in FIG. 10 and evidence suggested that lower molecular weight polymers would give increased matrix removal. To overcome this, a low molecular weight (1:1) MBPI-α-cyclodextrin polyurethane mixture was also prepared by reducing both reaction temperature and time during polymerization.

Synthesis of Low Molecular Weight (1:1) MBPI-α-Cyclodextrin Polymer

In a typical synthesis, 5.000 g of α-cyclodextrin (5.14 mmol) is placed in a flask along with a small stir bar. The flask is heated overnight to 140° C. under dynamic vacuum using a vacuum oven to fully dehydrate the cyclodextrin and glass flask. On the next day, the flask is transferred to a nitrogen line and purged with a continuous stream of inert gas. To the flask containing the dehydrated cyclodextrin is then added 50 ml of anhydrous dimethylformamide (DMF). The mixture is stirred vigorously under a nitrogen purge until the cyclodextrin fully dissolves. Once dissolved, 1.30 g (5.14 mmol) of methylenebis (phenyl-isocyanate) (MBPI) is added as one portion to the stirring solution under a continuous nitrogen purge. Following addition of the MBPI, the flask is fully purged with nitrogen to remove any residual atmospheric contaminants. The flask is then sealed under a positive pressure of nitrogen and allowed to react at 25° C. for 3 hrs. Once complete, the clear DMF solution is added dropwise to 500 ml of vigorously stirring methanol in order to precipitate the resulting polymer. The MBPI-α-cyclodextrin polymer precipitates as an extremely fine low density white powder suspended in the solvent. The polymer is collected by centrifugation and washed several times with water/methanol/centrifuge cycles. As an additional purification step, the polymer is also extensively washed using methanol extraction in a Soxhlet apparatus for 1-2 days to remove low molecular weight and small molecule impurities. The final product is then dried under dynamic vacuum overnight at 40° C. to remove absorbed solvent yielding the final product. Typical yields for this polymer range from 60-70%.

Figure 12B:
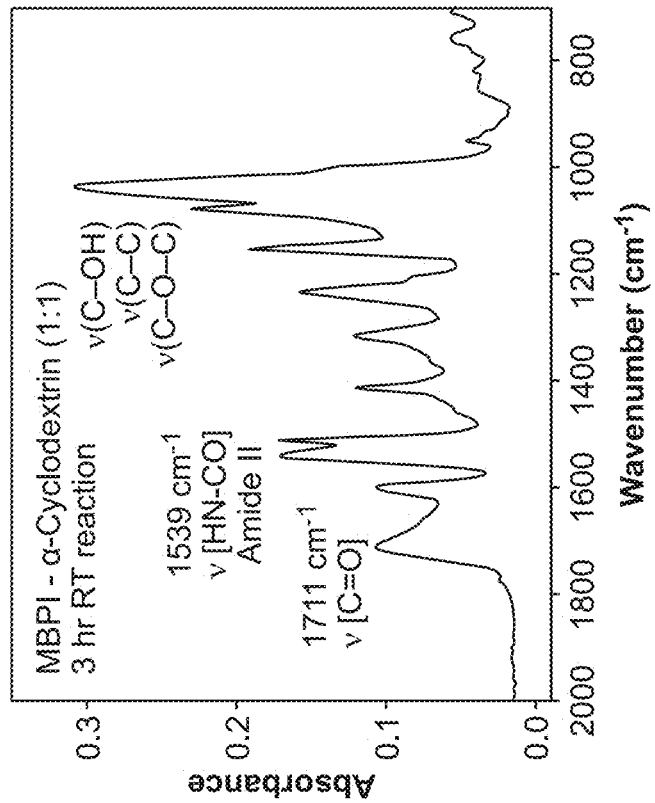
FIG. 12 shows the FT-IR spectra of a MBPI-α-cyclodextrin (1:1) polyurethane co-polymer: Panel a of FIG. 12 shows a complete IR spectrum and panel b shows IR spectrum from 2000-700 cm-1.
Figure 12A:
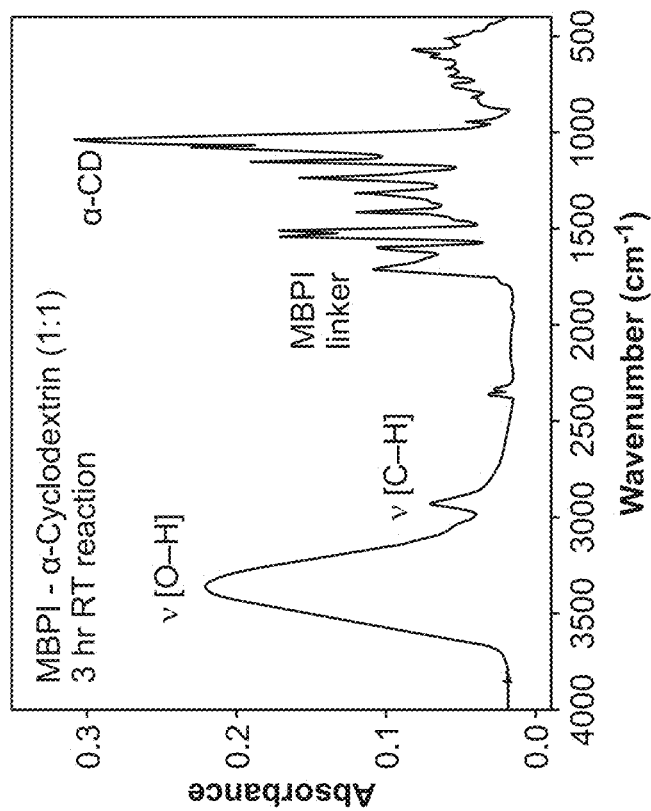

Synthesized samples of MBPI-α-cyclodextrin (1:1) polymer were examined using FT-IR spectroscopy. Example spectra are shown in FIG. 12 with the important identifying peaks labeled. All major vibrational modes have been assigned and are listed in Table 1. IR spectra of these polymers are dominated by 0-H, and C—O stretching modes and represented by absorbances at 3365 cm$^{-1}$ and 1037 cm$^{-1}$, respectively. These peaks arise solely from the cyclodextrin and are also found in IR spectra of native α-CD before polymerization. Confirmation of the formation of urethane linkages with the MBPI crosslinker is determined through the appearance of new vibrational modes at 1711 cm$^{-1}$, 1539 cm$^{-1}$, 1234 cm$^{-1}$ which represent the carbamate linkage between the MBPI and cyclodextrin molecules. These peaks correspond to urethane v [C=O], v [HN—CO], and [HN—CO] bending vibrations, respectively. Additional absorbances found in the IR spectra at 1600 cm$^{-1}$ and 1512 cm$^{-1}$ provide additional confirmation of the inclusion of MBPI monomers and correspond to predicted modes arising from para-substituted aromatic rings.

FIG. 12: FT-IR spectra of MBPI-α-cyclodextrin (1:1) polyurethane. Spectra acquired using KBr pellets under a nitrogen purge. (a) Complete IR spectrum. (b) IR spectrum of MBPI-α-CD polyurethane from 2000-700 cm$^{-1}$. Important identifying peaks for MBPI-α-cyclodextrin polyurethane are labeled.

TABLE 1

Experimentally obtained IR vibrational modes for MBPI-α-cyclodextrin polyurethane.

| Experimentally obtained frequency (cm$^{-1}$) | Assignment |
| --- | --- |
| 3365 | α-CD v[O—H] |
| 2929 | α-CD v [CH$_2$] |
| 1711 | Urethane v [C=O] |
| 1600 | MBPI [C=C]para |
| 1539 | Urethane v [HN—CO] |
| 1512 | MBPI [C=C]para |
| 1234 | Urethane [HN—CO] bending |
| 1037 | α-CD v[C—OH], v[C—O—C], v[C—C] |

Figure 13B:
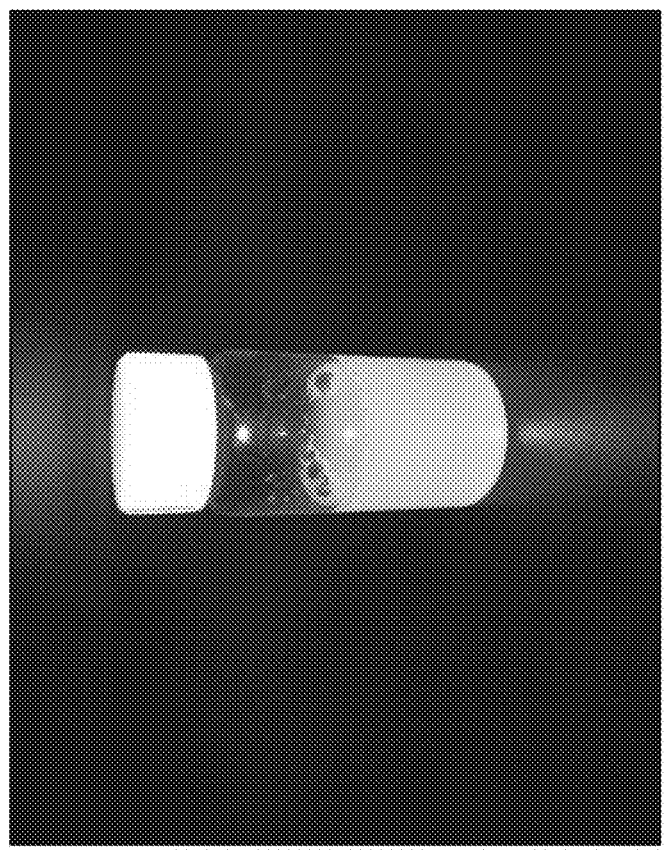
FIG. 13 shows a scanning electron micrograph illustrating the porous morphology of a sample of MBPI-α-cyclodextrin (1:1) polyurethane (see panel a). The polymer is composed of approximately 100 nm scale particles. Scale bar=1 micron; Photograph showing a stable colloidal suspension formed by MBPI-α-cyclodextrin (1:1) polyurethane in water (panel b). Although insoluble, the individual nanoscale particles shown in panel a disperse in water to form a stable translucent suspension.

The morphologies of synthesized MBPI-α-cyclodextrin polyurethane co-polymers were examined using scanning electron microscopy (SEM). Samples of MBPI-α-cyclodextrin polymer were deposited on SEM stubs using electrically-conductive adhesive and gold-coated to improve image quality. FIG. 13 shows a representative micrograph of one sample. Synthesis of this material consistently forms polyurethane particles approximately 100 nm in diameter with a high degree of free volume between the individual particles. In the bulk material, these nanoscale particles are fused together, but are readily dispersed in aqueous media to form stable colloidal suspensions where the particles separate and provide high surface area for interaction and extraction of lipids. Surface area measured for MBPI-α-cyclodextrin polyurethanes using nitrogen BJH absorption on a TriStar 3000 was found to be 40.5 $m^2/g$, suggesting the nanoscale particles are primarily non-porous in structure.

Figure 13A:
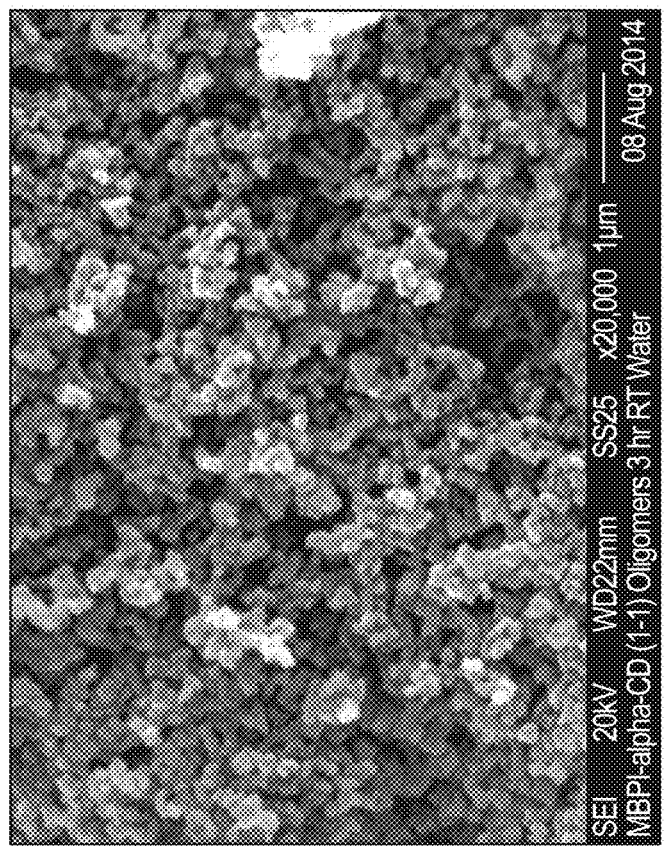

FIG. 13: (a) Scanning electron micrograph showing the porous morphology of a sample of MBPI-α-cyclodextrin (1:1) polyurethane. Polymer is composed of approximately 100 nm scale particles. Scale ba r=1 micron. (b) Photograph showing a stable colloidal suspension formed by MBPI α-cyclodextrin (1:1) polyurethane in water. Although insoluble, the individual nanoscale particles shown in FIG. 13(a) disperse in water to form a stable translucent suspension.

Figure 14:
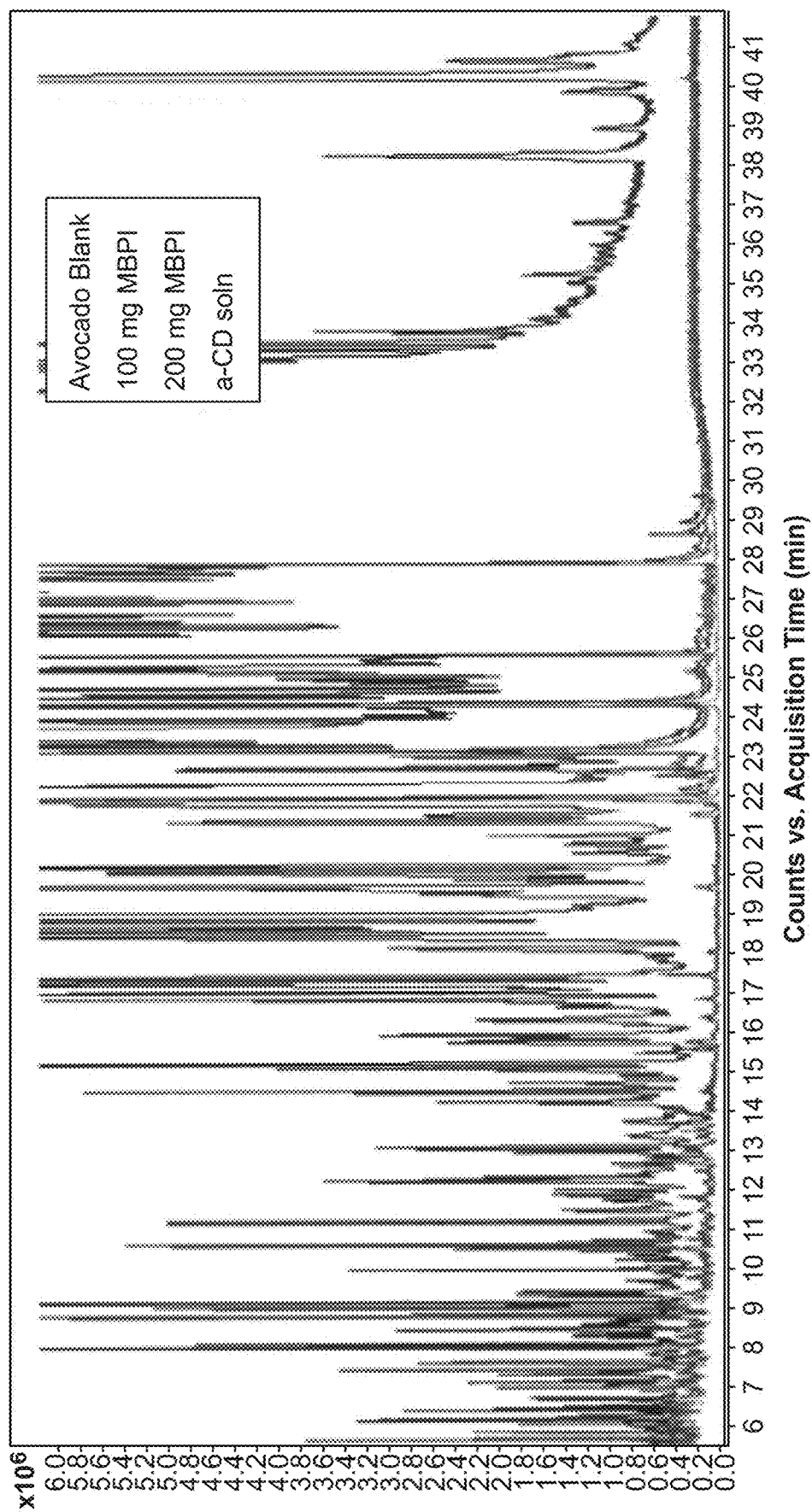
FIG. 14 shows CC-MS fullscan chromatograms (from top to bottom) of avocado before sample cleanup, after treatment with 100 mg 1:1 MBPI-α-CD from 3 h reaction after treatment with 200 mg 1:1 MBPI-α-CD and after treatment with α-CD solution 100 mg in 0.5 ml water.
Figure 15:
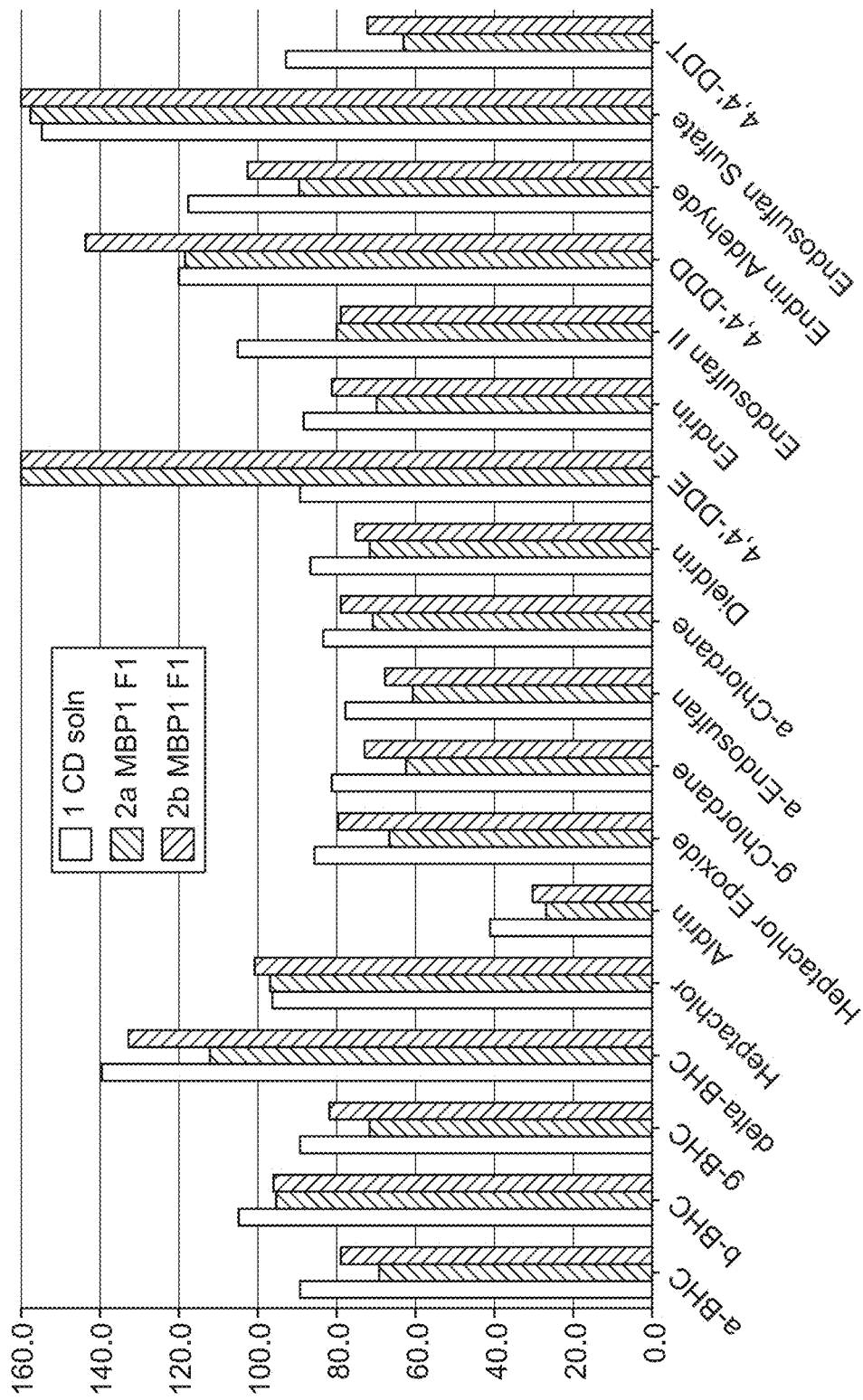
FIG. 15 illustrates the absolute recoveries of organochlorine pesticides in avocado after treatment with α-CD solution, 100 mg in 0.5 ml water (first bar), 100 mg 1:1 MBPI/α-CD (second bar), and 200 mg 1:1 MBPI/α-CD (third bar).
Figure 16:
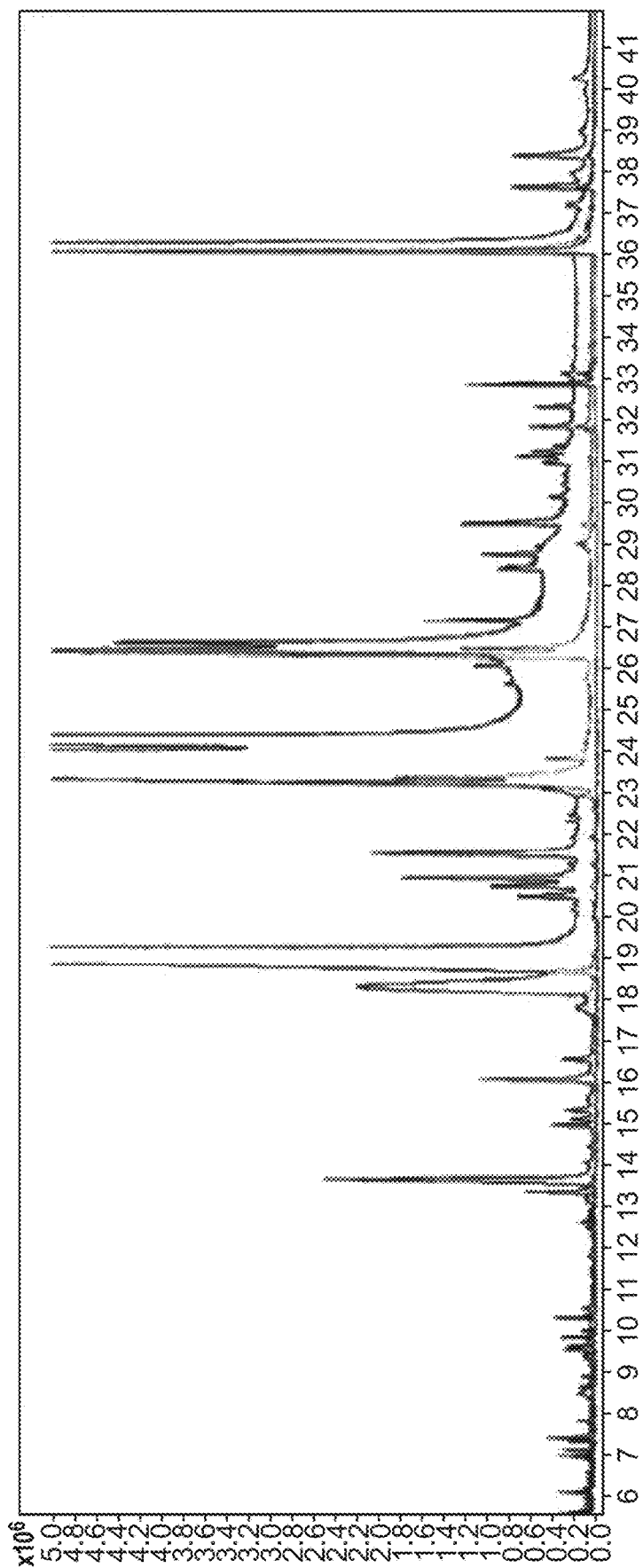
FIG. 16 shows overlaid GC-MS full-scan chromatograms (from top to bottom) of untreated beef liver treated with 100 mg 1:1 MBPI/α-CD and treated with α-CD solution 100 mg in 0.5 ml water.

As indicated in FIG. 14, the 1:1 MBPI-α-CD material generated from the 3 h reaction resulted in >95% removal of matrix background as indicated by GC-MS fullscan. This material gives comparable performance as the α-CD solution with the exception of impurities peaks at 22.0, 23.3, 24.4, 25.8, and 28.0 min. Some of these peaks arise from unremoved matrix and others from methylene-bis-phenylamine and ureas; left as byproducts from the synthesis. These processing impurities have since been removed via acid washes with methanol and water.

Analyte recovery was also accessed using the 1:1 MBPI-α-CD polyurethane from the 3 h reaction providing the results in Chart 2. Solvent calibration results indicate some minor analyte retention at 100 mg and 200 mg (5% to 20%) but display comparable recovery data to the α-CD solution. Some matrix enhancement is present for 4,4'-DDE and endosulfan; a result of the small amount of matrix in the final sample.

Example 2

The diisocyanates (DI) 1 to 9 (FIG. 1A) were combined with α-cyclodextrin (CD) according to the methods described herein and the conditions set forth in Tables 1 and 2 to produce a series of co-polymer compositions.
(1) 1,4-Diisocyanatobutane (DIB)
(2) 1,12-Diisocyanatododecane (DIDOD)
(3) Hexamethylene-diisocyanate (HMDI)
(4) 1,8-Diisocyanatooctane (DIOCT)
(5) 4,4'-Methylenebis(cyclohexyl-isocyanate) (MBCI)
(6) 3,3'-Dimethyl-4,4'-Biphenylene-diisocyanate (DMBP)
(7) 4,4'-Methylenebis(phenyl-isocyanate) (MBPI)
(8) Tolylene-2,4-diisocyanate (TDI)
(9) 1,4-Phenylene-diisocyanate (PDI)

TABLE 2

Synthetic conditions and polymer yields for aliphatic diisocyanate (DI) - α-cyclodextrin (CD) co-polymers 1-5.

| Co-Polymer Composition | DI | CD:DI molar ratio | Conc. (M) | Temp. (° C.) | Yield |
|---|---|---|---|---|---|
| 1a | 1 | 1:1 | 0.1 | 23 | 21% |
| 1b | 1 | 1:3 | 0.1 | 23 | 36% |
| 1c | 1 | 1:1 | 0.2 | 23 | 43% |
| 1d | 1 | 1:3 | 0.2 | 23 | 48% |
| 1e | 1 | 1:1 | 0.1 | 60 | 42% |
| 1f | 1 | 1:3 | 0.1 | 60 | 35% |
| 1g | 1 | 1:1 | 0.2 | 60 | 51% |
| 1h | 1 | 1:3 | 0.2 | 60 | 57% |
| 2a | 2 | 1:1 | 0.1 | 23 | 42% |
| 2b | 2 | 1:3 | 0.1 | 23 | 54% |
| 2c | 2 | 1:1 | 0.2 | 23 | 62% |
| 2d | 2 | 1:3 | 0.2 | 23 | 66% |
| 2e | 2 | 1:1 | 0.1 | 60 | 50% |
| 2f | 2 | 1:3 | 0.1 | 60 | 54% |
| 2g | 2 | 1:1 | 0.2 | 60 | 61% |
| 2h | 2 | 1:3 | 0.2 | 60 | 68% |
| 3a | 3 | 1:1 | 0.1 | 23 | 20% |
| 3b | 3 | 1:3 | 0.1 | 23 | 64% |
| 3c | 3 | 1:1 | 0.2 | 23 | 33% |
| 3d | 3 | 1:3 | 0.2 | 23 | 31% |
| 3e | 3 | 1:1 | 0.1 | 60 | 27% |
| 3f | 3 | 1:3 | 0.1 | 60 | 84% |
| 3g | 3 | 1:1 | 0.2 | 60 | 45% |
| 3h | 3 | 1:3 | 0.2 | 60 | 85% |
| 4a | 4 | 1:1 | 0.1 | 23 | 40% |
| 4b | 4 | 1:3 | 0.1 | 23 | 51% |
| 4c | 4 | 1:1 | 0.2 | 23 | 57% |
| 4d | 4 | 1:3 | 0.2 | 23 | 61% |
| 4e | 4 | 1:1 | 0.1 | 60 | 46% |
| 4f | 4 | 1:3 | 0.1 | 60 | 51% |
| 4g | 4 | 1:1 | 0.2 | 60 | 55% |
| 4h | 4 | 1:3 | 0.2 | 60 | 61% |
| 5a | 5 | 1:1 | 0.1 | 23 | 54% |
| 5b | 5 | 1:3 | 0.1 | 23 | 61% |
| 5c | 5 | 1:1 | 0.2 | 23 | 77% |
| 5d | 5 | 1:3 | 0.2 | 23 | 79% |
| 5e | 5 | 1:1 | 0.1 | 60 | 75% |
| 5f | 5 | 1:3 | 0.1 | 60 | 63% |
| 5g | 5 | 1:1 | 0.2 | 60 | 79% |
| 5h | 5 | 1:3 | 0.2 | 60 | 81% |

TABLE 3

Synthetic conditions and polymer yields for aromatic diisocyanate -α-cyclodextrin co-polymers 6-9.

| Polymer Composition | DI | CD:DI molar ratio | Conc. (M) | Temp. (° C.) | Yield |
|---|---|---|---|---|---|
| 6a | 6 | 1:1 | 0.1 | 23 | 44% |
| 6b | 6 | 1:3 | 0.1 | 23 | 52% |
| 6c | 6 | 1:1 | 0.2 | 23 | 61% |
| 6d | 6 | 1:3 | 0.2 | 23 | 63% |
| 6e | 6 | 1:1 | 0.1 | 60 | 60% |
| 6f | 6 | 1:3 | 0.1 | 60 | 55% |
| 6g | 6 | 1:1 | 0.2 | 60 | 72% |
| 6h | 6 | 1:3 | 0.2 | 60 | 74% |
| 7a | 7 | 1:1 | 0.1 | 23 | 53% |
| 7b | 7 | 1:3 | 0.1 | 23 | 62% |
| 7c | 7 | 1:1 | 0.2 | 23 | 76% |
| 7d | 7 | 1:3 | 0.2 | 23 | 77% |
| 7e | 7 | 1:1 | 0.1 | 60 | 72% |
| 7f | 7 | 1:3 | 0.1 | 60 | 63% |
| 7g | 7 | 1:1 | 0.2 | 60 | 81% |
| 7h | 7 | 1:3 | 0.2 | 60 | 83% |
| 8a | 8 | 1:1 | 0.1 | 23 | 30% |
| 8b | 8 | 1:3 | 0.1 | 23 | 62% |
| 8c | 8 | 1:1 | 0.2 | 23 | 35% |
| 8d | 8 | 1:3 | 0.2 | 23 | 39% |
| 8e | 8 | 1:1 | 0.1 | 60 | 28% |
| 8f | 8 | 1:3 | 0.1 | 60 | 84% |
| 8g | 8 | 1:1 | 0.2 | 60 | 48% |

TABLE 3-continued

Synthetic conditions and polymer yields for aromatic diisocyanate -α-cyclodextrin co-polymers 6-9.

| Polymer Composition | DI | CD:DI molar ratio | Conc. (M) | Temp. (° C.) | Yield |
|---|---|---|---|---|---|
| 8h | 8 | 1:3 | 0.2 | 60 | 86% |
| 9a | 9 | 1:1 | 0.1 | 23 | 63% |
| 9b | 9 | 1:3 | 0.1 | 23 | 74% |
| 9c | 9 | 1:1 | 0.2 | 23 | 87% |
| 9d | 9 | 1:3 | 0.2 | 23 | 88% |
| 9e | 9 | 1:1 | 0.1 | 60 | 84% |
| 9f | 9 | 1:3 | 0.1 | 60 | 75% |
| 9g | 9 | 1:1 | 0.2 | 60 | 86% |
| 9h | 9 | 1:3 | 0.2 | 60 | 88% |

Example 3: QuEChERS Extraction

The following general methods were adapted for use in the preparation of a QuEChERS sample for analysis using the subject compositions.
Salting Out Extraction—General Procedure
 1. Weigh sample
 2. Add water and QC spikes if needed and spike with internal standard
 3. Add acetonitrile
 4. Vortex or shake
 5. Add salt packet
 6. Shake 1 minute
 7. Centrifuge at 4000 rpm for 5 minutes
 8. Phase separation of acetonitrile and aqueous layer An appropriate amount of sample is weighed into a 50 ml centrifuge tube and spiked with standard as necessary. Water is added as required and acetonitrile is added as an extraction solvent. The tube is capped and shaken vigorously by hand and mechanical shaker. Next, QuEChERS extraction salts are added to the mixture followed by vigorous shaking and centrifugation. The resulting tube contains different layers with the acetonitrile extract on top.
Sample Cleanup For this method, the conventional dispersive solid phase extraction cleanup is modified to include the subject α-cyclodextrin composition. The extract is transferred to a clean centrifuge tube and the α-cyclodextrin solution is added by micropipette. This instantly forms a thick white precipitate consisting of insoluble α-cyclodextrins and matrix. Alternatively, a α-cyclodextrin and/or α-cyclodextrin co-polymer can be used as a solid powder with additional water. The tube is capped and vortexed to ensure homogeneity. The slurry is then centrifuged or filtered resulting in a clear solution free of lipids. The solution is then transferred to autosampler tubes for LC-MS analysis or evaporated and reconstituted for GC-MS analysis. Alternatively, the solution can be transferred to a tube containing salts (MgSO$_4$, NaCl) to partition the water and acetonitrile. The upper acetonitrile layer can be transferred to autosampler vials or diluted for analysis.
Dispersive Solid Phase Extraction (dSPE)—General Procedure
 1. Choose the dispersive cleanup kit and add acetonitrile extract
 2. Vortex for 1 minute
 3. Centrifuge at 4000 rpm for 5 minutes
 4. Take amount of supernatant and dry down, dilute, or partition with salts as needed
 5. Place in autosampler vials for GC or LC analysis Protein Precipitation and Functional Filtration—General Procedure
 1. Add crash solvent (acetonitrile) to a non-drip filter tube or centrifuge tube
 2. Add sample
 3. Mix with pipette 5 times to precipitate sample or vortex
 4. Apply vacuum, positive pressure to filter through 0.22 µm membrane or centrifugation.

The subject methods and compositions are also beneficial to protein precipitation or other extraction workflows that pass a crude extract through a membrane containing lipid removal media or mix with lipid removal media in a centrifuge tube. An extract or sample and a crash solvent can be added to a cylindrical cartridge or centrifuge tube. The extract can flow through or be suspended in the cartridge using a non-drip filter membrane. If suspended, the mixture can be aspirated for thorough mixing before being pulled through the multiple membranes or vortexed and then centrifuged in a tube. When the extract passes through the membrane by either gravity, centrifuge, negative or positive pressure, the depth filter removes particulates and proteins and the lipid retaining membrane removes lipids from the extract; allowing target analytes to pass through. In a centrifuge tube format, the supernatant can be transferred, diluted, or evaporated and reconstituted for analysis.
Extraction Procedure The following extraction protocol that can utilized in conjunction with the general methods described herein. This modified extraction protocol can also be implemented using the various α-CD and/or α-CD copolymer compositions. A sample is weighed into a 50 mL centrifuge tube and additional water is added as necessary. An organic solvent (acetonitrile or acetone) is then added followed by mixing and centrifugation. The supernatant is transferred to a second tube containing α-CD and/or α-CD copolymer. The slurry is mixed and centrifuged. The supernatant is decanted into a third tube containing salts followed by shaking and centrifugation. The final supernatant contains two layers. The upper organic layer is transferred, diluted with mobile, phase or evaporated and reconstituted for analysis.

An experiment was performed to visually compared QuEChERS extracts from orange when treated with various dSPE; A) α-CD:7a blend; B) PSA; C) C18/PSA/GCB; D) no cleanup. The final extract of A is near colorless, B is bright orange, C is colorless and D is bright orange.

A second experiment was performed to visually compared QuEChERS extracts from spinach when treated with various dSPE; A) α-CD:7a blend; B) PSA/GCB; C) C18/PSA/GCB; D) no cleanup. The final extract of A is yellow, B is colorless, C is yellow and D is bright green.

A third experiment was performed to visually compared QuEChERS extracts from red pepper when treated with various dSPE; A) α-CD:7a blend; B) PSA; C) C18/PSA/GCB; D) no cleanup. The final extract of A was yellow, B was red/orange, C was yellow and D was red/orange.

Example 4: α-CD Urethane Polymers for Selective Lipid Removal

First generations of α-cyclodextrin-polyurethane polymers were synthesized for testing with lipid sample extracts that incorporated hexamethylene diisocyanate (HMDI) or methylenebis (phenyl-isocyanate) (MBPI). These diisocyanate cross-linkers were chosen for their low cost and structural differences. HMDI incorporates a flexible aliphatic chain six methylene units long while MBPI is comprised of two aromatic rings linked by a single methylene group resulting in a more rigid structure.

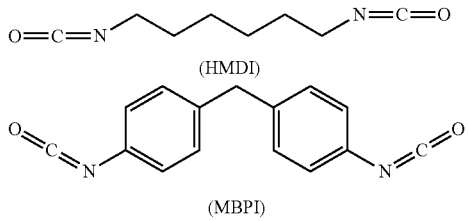

(HMDI)

(MBPI)

Initial polymerization reactions used to prepare the polymers made use of 3:1 and 4:1 crosslinker to CD ratios. These polymers however, were found to gel during the course of polymerization making isolation of purified materials difficult. These highly cross-linked polymers consist of random networks of interconnected cyclodextrin molecules which can retain trapped solvent molecules or unreacted byproducts introducing impurities into the final product. Imaging of these polymers by scanning electron microscopy (SEM) (FIG. 8) revealed a dense non-porous structure under high magnification.

Figure 8:
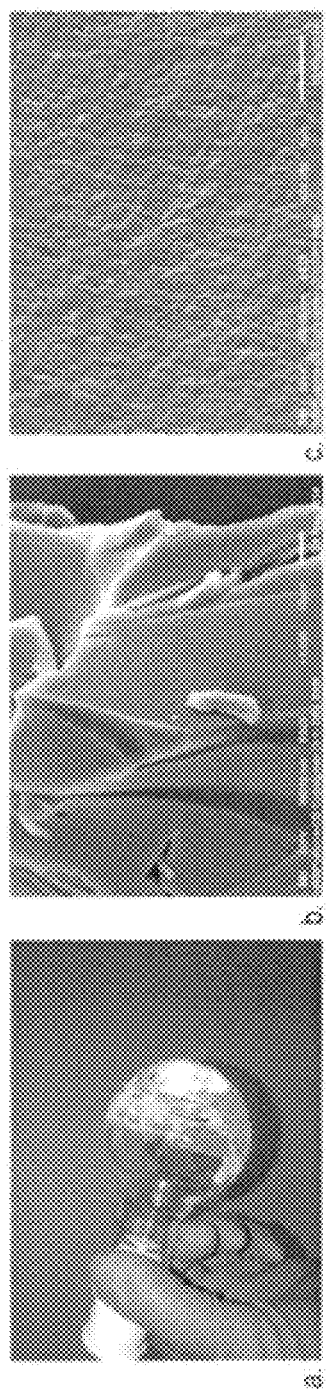
FIG. 8 shows an image showing the gelation of MBPI-α-cyclodextrin (3:1) polymer after synthesis at 50° C. in dimethylformamide (see panel a). Panels b and c of FIG. 8 show scanning electron micrograph images illustrating the solid and dense morphology of MBPI-α-cyclodextrin (3:1) polymer.

FIG. 8: Panel a of FIG. 8 is an image showing the gelation of MBPI-α-cyclodextrin (3:1) polymer after synthesis at 50° C. in dimethylformamide. In panels (b) and (c) are shown scanning electron micrographs showing the solid and dense morphology of MBPI-α-cyclodextrin (3:1) polymer.

Extraction and Cleanup of Avocado Sample

A screening experiment was performed to investigate a QuEChERS protocol for the extraction and cleanup of avocado and samples were analyzed by GC-MS for sample cleanliness and analyte recovery. Avocado (5 g) is weighed into a 50 ml centrifuge tube and spiked as necessary with QC standards and internal standards. Water (5 ml) is added to the sample and mixed followed by 10 ml of acetonitrile. The tube is placed on a vertical shaking system for 2 min. QuEChERS extraction salts (4 g MgSO4, 1 g NaCl) are added to the mixture and shaken for 2 min on the mechanical shaker. Other extraction salts can include mixtures of ammonium formate, ammonium acetate, sodium citrate, sodium citrate sesquihydrate sodium chloride, and/or magnesium sulfate. Next, the mixture is centrifuged at 5000 rpm for 5 min resulting in phase separation of the upper acetonitrile extract and the aqueous lower layer. The resulting clear, green extract is then added to 2 ml Eppendorf tubes containing the α-CD composition and additional water as needed. To each tube, 0.5 mL of water, then 0.5 ml of acetonitrile extract is added and mixed for 30 seconds to 60 seconds to conduct the dSPE. The samples are then centrifuged at 7000 rpm for 3 min and decanted into new Eppendorf tubes containing 200 mg of 4:1 MgSO4, NaCl (previously mentioned salts can also be used). The samples are mixed for an additional 10 seconds, centrifuged at 7000 rpm for 3 minutes, and the upper layer is transferred to autosampler vials for GC-MS analysis.

Results by GC-MS are shown in FIG. 9 indicate that the HDMI-α-CD polymers only show approximately 10% reduction in matrix background. However, as shown in FIG. 10 the MBPI-α-CD polymers show approximately 70% matrix removal for the 3:1 polymer and approximately 85% matrix removal with the 1:1 polymer.

FIG. 9 shows overlaid chromatograms by GC-MS fullscan for avocado untreated (black), treatment with 100 mg 1:1 HDMI-α-CD in 1:1 acetonitrile/H2O, treatment with 100 mg 2:1 HDMI-α-CD in 1:1 acetonitrile/H2O, treatment with 100 mg 2:1 HDMI-α-CD in 1:1 acetonitrile/H2O, and treatment with 100 mg α-CD in water (bottom). FIG. 10 shows GC-MS fullscan chromatogram overlays of untreated avocado (black), after treatment with 100 mg 3:1 MBPI-α-CD in 1:1 acetonitrile/H2O, after treatment with 100 mg 1:1 MBPI-α-CD in 1:1 acetonitrile/H2O, after treatment with 100 mg α-CD dissolved in 0.5 ml water (bottom).

Figure 11:
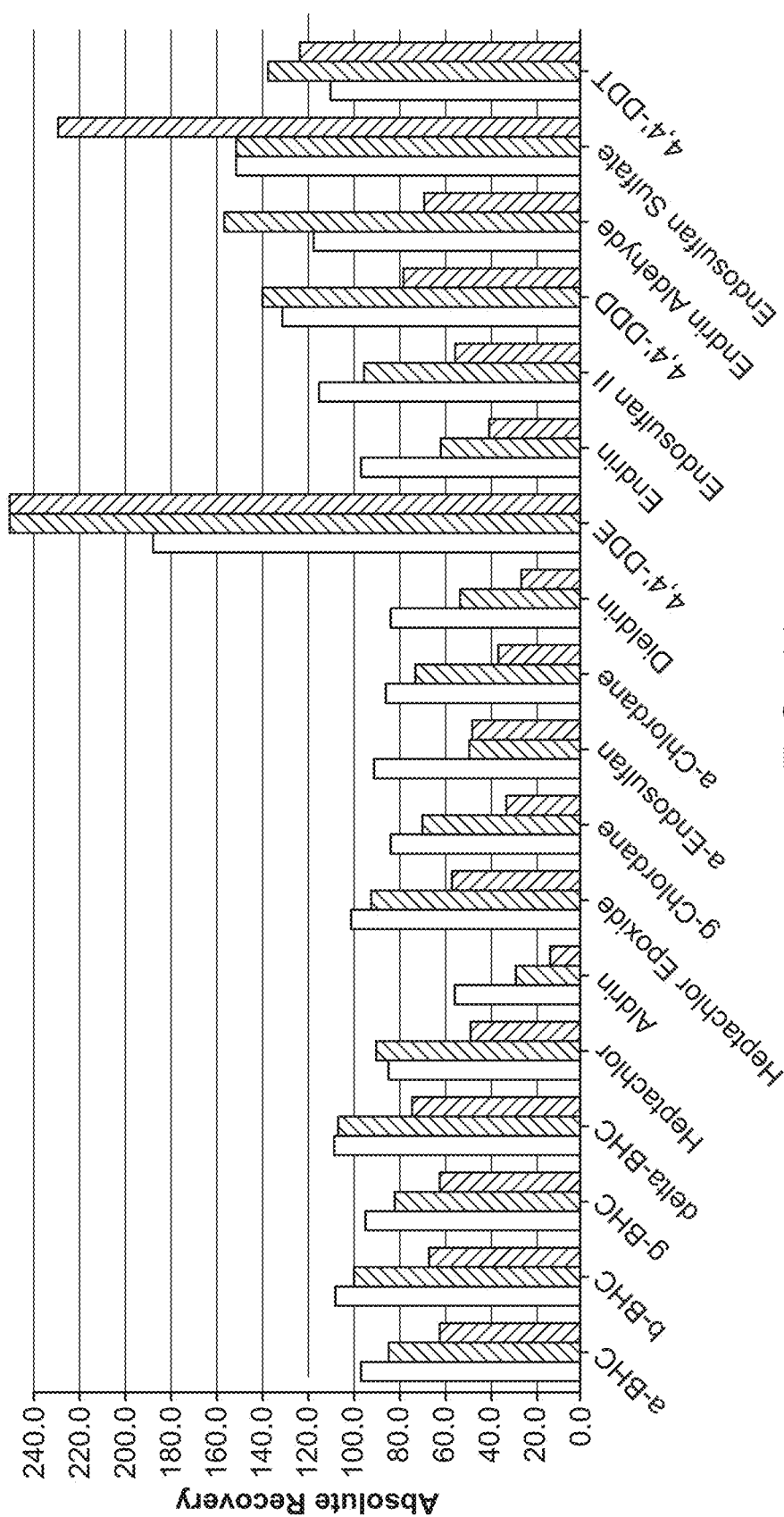
FIG. 11 illustrates the absolute recoveries of organochlorine pesticides (50 ppb) by GC-MS (selected ion monitoring) in avocado after treatment with α-CD solution in 0.5 ml water (first bar), 100 mg 1:1 MBPI-α-CD (second bar), and 200 mg 3:1 MBPI-α-CD (third bar).

To assess target analyte recovery, pesticides were spiked into avocado at 50 ng/ml (ppb) and submitted to the QuEChERS protocol described above. A five point solvent calibration curve (12.5, 25, 50, 100, and 200 ng/mL) was used to quantify results in FIG. 11. FIG. 11: Absolute recoveries of organochlorine pesticides (50 ppb) by GC-MS(SIM) (selected ion monitoring) in avocado after treatment with a-CD solution in 0.5 ml water (first bar), 100 mg 1:1 MBPI-α-CD (second bar), and 200 mg 3:1 MBPI-α-CD (third bar). Significant pigment removal is evident by the disappearance of green coloration in the final sample.

Example 5: Matrix Removal by α-CD, α-CD Solution, α-CD Copolymers, and α-CD: Copolymer Blends I. Materials and Methods
A. Abbreviations

| | |
|---|---|
| α-CD | α-Cyclodextrin |
| α-CD solution | α-Cyclodextrin solution in water |
| C18 | Octadecylsilane on silica |
| PSA | Primary secondary amine; 400 mg PSA, MgSO4 |
| GCB | Graphitized carbon black |
| C18/PSA | 400 mg C18, 400 mg PSA, 1200 mg MgSO4 |
| PSA/GCB | 150 mg PSA, 45 mg GCB, 855 mg MgSO4 |
| C18/PSA/GCB | 400 mg PSA, 400 mg C18, 45 mg GCB, 1200 mg MgSO4 |
| C18•Zirconia | Bonded C18 on zirconia particle, 500 mg |
| dSPE | Dispersive Solid Phase Extraction |
| Sorbents | Adsorbent materials used for dSPE |
| 2e | 1:1 DIDOD-α-CD copolymer |
| 3a | HMDI-α-CD copolymer |
| 5e | 1:1 MBCI-α-CD copolymer |
| 6a | 1:1 DMBP-α-CD copolymer |
| 7a | 1:1 MBPI-α-CD copolymer |
| 7b | 3:1 MBPI-α-CD copolymer |
| 8f | TDI-α-CD copolymer |
| 1:1, α-CD:7a blend | α-Cyclodextrin:MBPI-α-CD blend; 1:1 ratio |
| 2:1, α-CD:7a blend | α-Cyclodextrin:MBPI-α-CD blend; 2:1 ratio |
| QuEChERS | Quick Easy Cheap Effective Rugged Safe extraction protocol |

B. Instrumentation and Chemicals

Instruments: Agilent Technologies 6890 GC with 5875C MSD and FID; 7890 GC with 5977 MSD with ECD; 1290 LC with 6490 MS/MS (QQQ), and 1290 LC with 6150 MSD. MS grade solvents were used for eluents and sample preparation reagents. A reverse osmosis water purification system provided purified water for analysis and sample preparation. QuEChERS materials including salts, tubes, and dSPE sorbents were provided by Agilent Technologies. Agilent Captiva ND and NDL filter tubes were used for protein precipitation analyses. Protein precipitation was also performed in 2 mL centrifuge tubes and 96 well centrifugation plates.

C. General Method for Preparation of a α-CD Solution

Transfer 2.0 g of α-CD into a 20 mL amber glass vial and add 10 mL of purified water. Warm the vial to 50° C. and mix until α-CD completely dissolves. Cool to room temperature; the α-CD will remain in solution for several weeks. Dissolve with heat as needed when a precipitate occurs. Deliver the solution to extracts as specified in the following procedures or as needed.

D. Calculation of Matrix Removal

Figure 2:
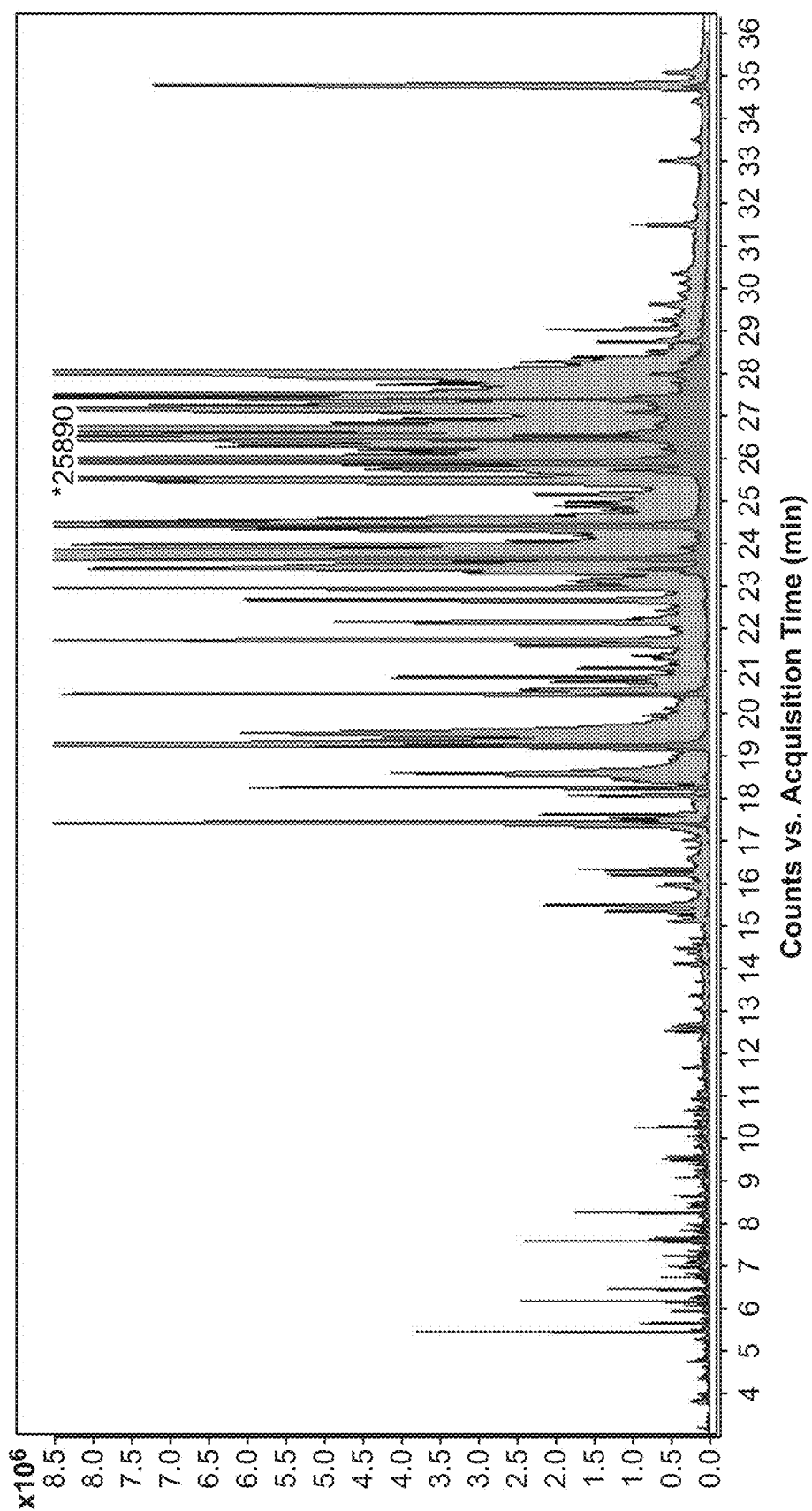
FIG. 2 shows a GC-MS fullscan chromatogram overlay (from top to bottom) of avocado before dSPE treatment and after treatment with a 2:1, α-CD:α-CD co-polymer (7a) blend with integrated chromatographic profiles for the matrix removal calculation.

FIG. 2: GC-MS fullscan chromatogram overlay of avocado before and after treatment with 2:1, α-CD:7a blend with integrated profiles for the matrix removal calculation.

$$\% \text{ Matrix Removal} = \frac{(\text{Extract Peak Area}) - (\text{Sample Peak Area})}{(\text{Extract Peak Area})} \times 100$$

Figure 3:
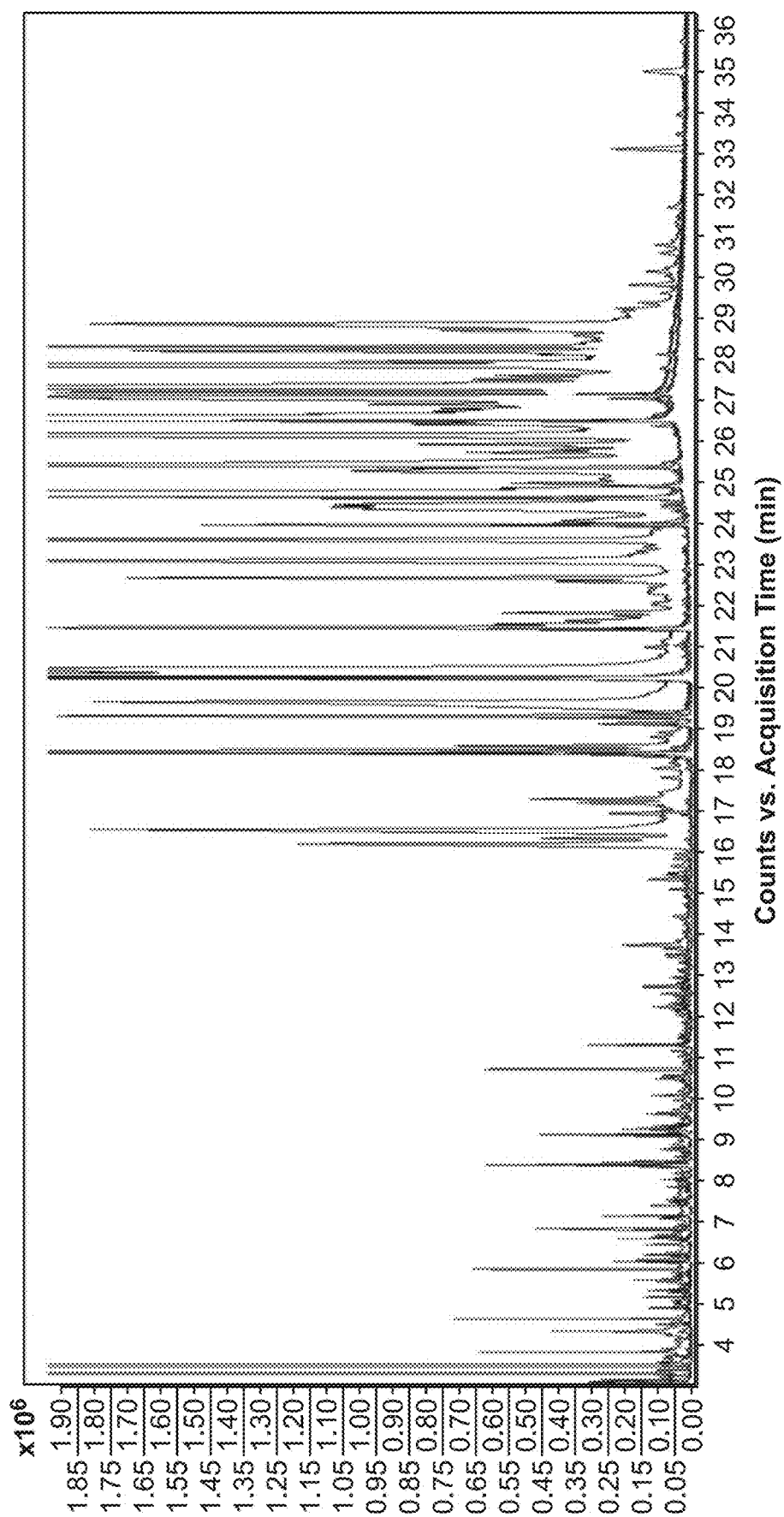
FIG. 3 shows a GC-MS fullscan chromatogram overlay (from top to bottom) of avocado extract before dSPE treatment, after treatment with α-CD co-polymer (7a) (83.8% matrix removal), with a 2:1, α-CD:α-CD co-polymer (7a) blend (88.5% matrix removal) and α-CD (90.7% matrix removal).
Figure 4:
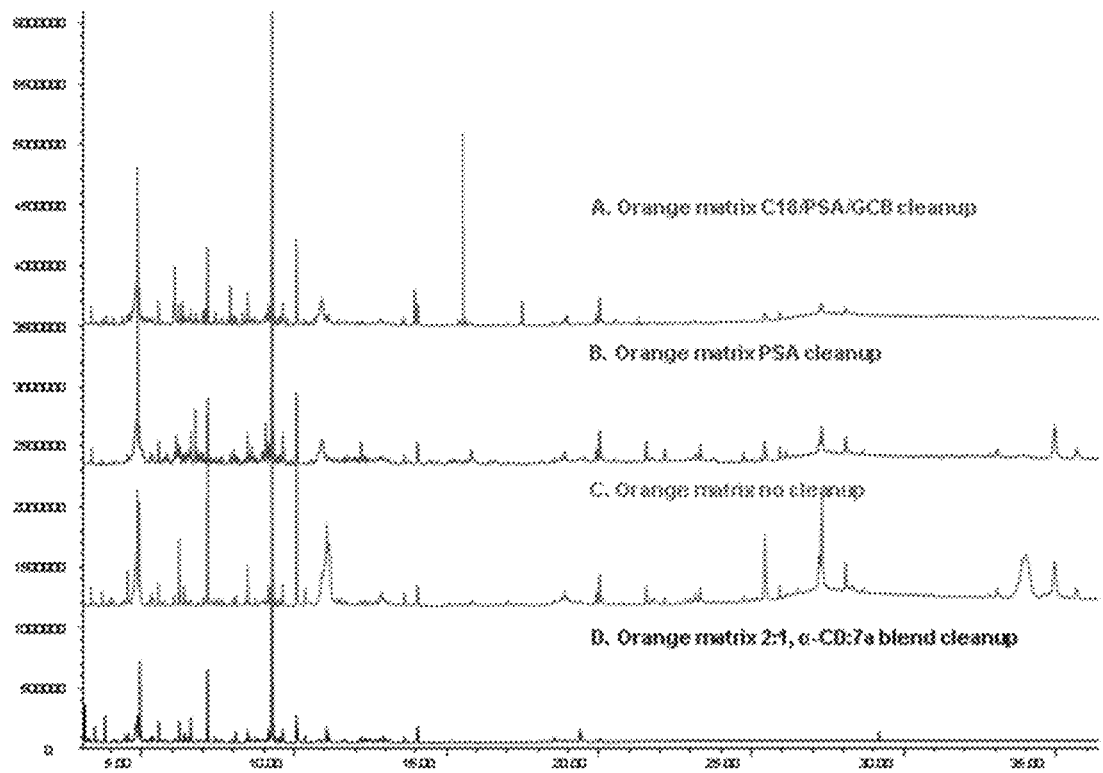
FIG. 4 shows a chromatogram overlay of orange extract with various cleanups by GC-MS.
Figure 5:
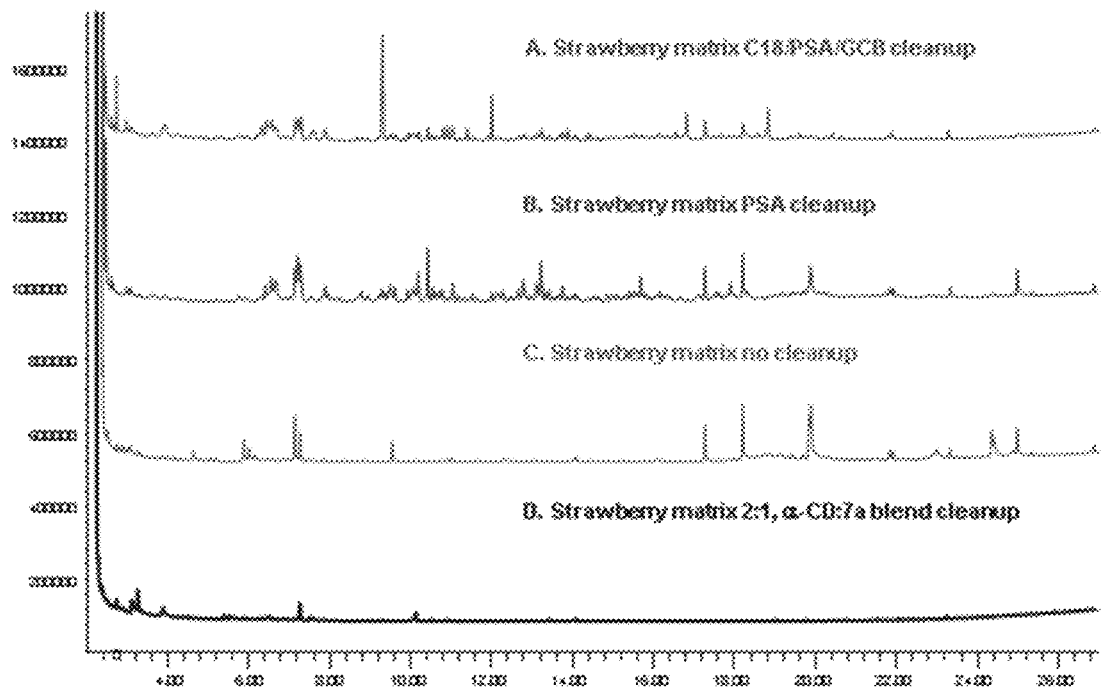
FIG. 5 shows a chromatogram overlay of strawberry extract with various cleanups by GC-FID.
Figure 6:
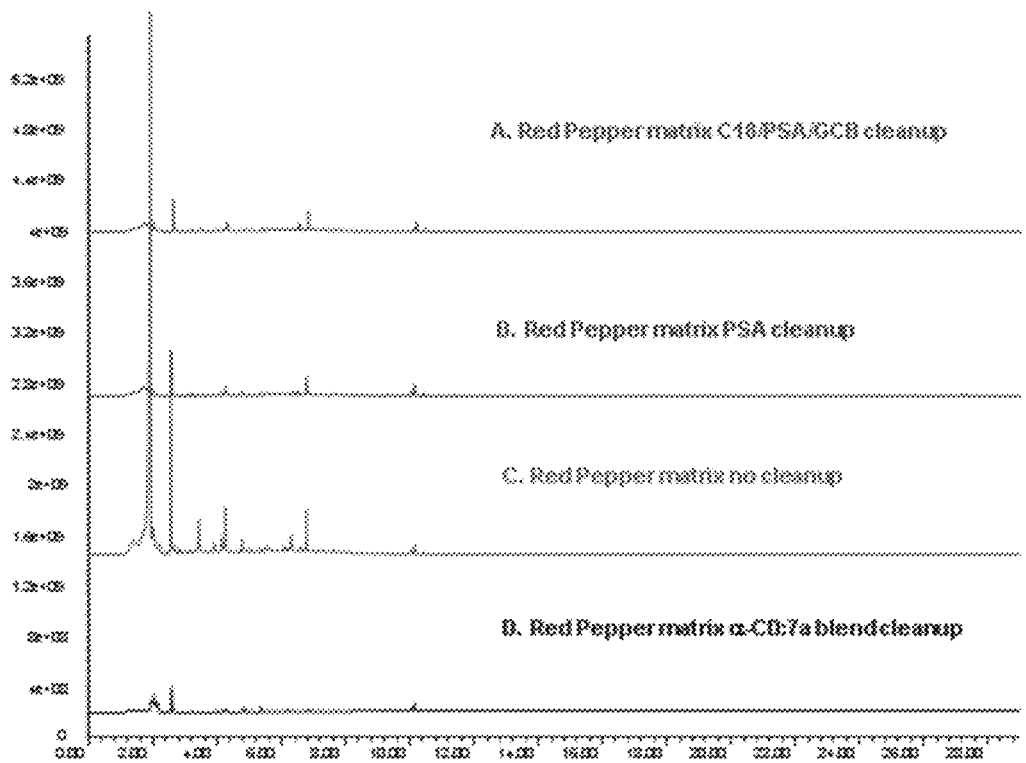
FIG. 6 shows a chromatogram overlay of red pepper extract with various cleanups by GC-ECD.

FIG. 3 shows a GC-MS fullscan chromatogram overlay (from top to bottom) of avocado extract before dSPE treatment, after treatment with α-CD co-polymer (7a) (83.8% matrix removal), 2:1, α-CD:α-CD co-polymer (7a) blend (88.5% matrix removal) and α-CD (90.7% matrix removal).

E. Calculation of Analyte Recoveries

Instrumental analysis methods were optimized for the various analyses using LC-MS/MS, GC-MS, and GC-MS/MS to achieve selectivity, sensitivity, and broad detection for applications including multi-class, multi-residue pesticide and veterinary drug analysis. Appropriate ions were selected for the various analytes as primary and secondary transitions for quantitation and confirmation, respectively. Chromatographic peaks corresponding to the analytes of interest were integrated to give peak areas and compared to solvent standard calibration curves and matrix matched calibration curves using Mass Hunter and Chem Station software to give calculated peak areas, final concentrations, and percent recoveries. Additionally, single point calibration was implemented to calculate percent recovery by using the sample and standard peak areas in the following formula.

$$\text{Recovery (\%)} = \frac{\text{Peak Area of Sample}}{\text{Peak Area of Standard}} \times 100$$

II. Evaluation of α-CD, α-CD Solution, α-CD Containing Polymers, and Blends for Cleanup of Sample Extracts Prior to Analysis.

A. Recovery and Matrix Removal Data for α-CD, α-CD Solution, α-CD Containing Polymers, and α-CD: α-CD Polymer Blends.

Extraction (QuEChERS)

A thoroughly homogenized avocado sample was weighed (15 g) into a 50 mL centrifuge tube and spiked with appropriate internal and QC standards at 100 ppb. An unspiked avocado sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD or α-CD containing polymers or blends.

Cleanup (dSPE)

The materials were weighed (100 mg) into a 2 mL centrifuge tube. Next, 0.5 mL of purified water was added to the solids (or 0.5 mL of α-CD solution only added) and then 0.5 mL of the acetonitrile avocado extract. Then, the mixture was vortexed for 1 min and then centrifuged at 13000 rpm for 3 min. The supernatant was then carefully decanted into a second 2 mL, centrifuge tube containing 200 mg sodium chloride:magnesium sulfate (1:4). The mixture was vortex for 5 s and centrifuged at 13000 rpm for 3 min. The resulting supernatant gave phase separation with the acetonitrile layer on top. The upper layer was transferred to an autosampler vial for GC-MS analysis for quantitation and matrix removal analysis.

TABLE 4

Analyte recoveries of pesticides in avocado, applying a cleanup dSPE step with the various α-CD and α-CD containing polymers.

| | Pesticide Recoveries in Avocado at 100 ppb by GC-MS (SIM) | | | | | | |
|---|---|---|---|---|---|---|---|
| | α-CD | α-CD solution | 8f | 6a | 2e | 7a | 5e |
| α-BHC | 100.6 | 95.6 | 94.6 | 102.0 | 102 | 87.5 | 84.5 |
| β-BHC | 107.7 | 94.3 | 83.8 | 111.0 | 111 | 88.8 | 110.7 |
| γ-BHC | 104.5 | 93.7 | 72.9 | 85.0 | 85 | 78.1 | 84.2 |
| δ-BHC | 112.3 | 97.2 | 92.1 | 110.4 | 110.4 | 84.9 | 101.8 |

TABLE 5

Matrix removal ranges from evaluation of avocado extracts treated with α-CD and α-CD containing polymers.

| | Matrix Removal (%) of Avocado Extracts by GC-MS Fullscan | | | | |
|---|---|---|---|---|---|
| | α-CD | α-CD solution | 5a | 1:1, α-CD:7a | 2:1, α-CD:7a |
| % Matrix Removal | 79-94.2 | 89.0-96.9 | 78.9-92.1 | 84.6-90.6 | 81.9-89.8 |
| | 3a | 2e | 8f | 5e | 6a |
| % Matrix Removal | 20.1-23.8 | 75.4-77.3 | 68.9-75.8 | 45.9-80.0 | 75.4-77.3 |

B. Cyclodextrin Blending Evaluation

Blending Procedure

The 7a copolymer was blended with α-CD by mixing the purified solids in a 1:1 and 1:2 ratio, respectively, by stirring, shaking, and tumbling for 2 min in an suitably sized container.

Extraction (QuEChERS)

A thoroughly homogenized avocado sample was weighed (15 g) into a 50 mL centrifuge tube and spiked with appropriate internal and QC standards at 100 ppb. An unspiked avocado sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD or α-CD containing polymers or blends.

Cleanup (dSPE)

The materials were weighed (100 mg) into a 2 mL centrifuge tube. Next, 0.5 mL of purified water was added to the solids (or 0.5 mL of α-CD solution only added) and then 0.5 mL of the acetonitrile avocado extract. Then, the mixture was vortexed for 1 min and then centrifuged at 13000 rpm for 3 min. The supernatant was then carefully decanted into a second 2 mL centrifuge tube containing 200 mg sodium chloride:magnesium sulfate (1:4). The mixture was vortex for 5 s and centrifuged at 13000 rpm for 3 min. The resulting supernatant gave phase separation with the acetonitrile layer on top. The upper layer was transferred to an autosampler vial for GC-MS analysis for quantitation.

TABLE 6

Analyte recoveries of pesticides in avocado, applying a cleanup dSPE step with the various α-CD and α-CD polymer blends.

| | Pesticide Recoveries at 100 ppb by GC-MS (SIM) | | | |
|---|---|---|---|---|
| | α-CD | MBPI-α-CD | 1:1, α-CD:7a blend | 2:1, α-CD:7a blend |
| α-BHC | 100.6 | 87.5 | 90.7 | 107.6 |
| β-BHC | 107.7 | 88.8 | 98.8 | 119.1 |
| γ-BHC | 104.5 | 78.1 | 88.8 | 110.7 |
| δ-BHC | 112.3 | 84.9 | 92.7 | 109.2 |
| Heptachlor | 70.2 | 52.5 | 72.5 | 71.1 |
| Aldrin | 67.3 | 10.7 | 25.9 | 61.3 |
| Heptachlor Epoxide | 93.5 | 83.2 | 93.0 | 98.3 |
| γ-Chlordane | 76.8 | 64.4 | 70.2 | 78.8 |
| α-Endosulfan | 81.2 | 24.4 | 53.1 | 69.4 |
| α-Chlordane | 75.8 | 63.0 | 71.7 | 78.7 |
| Dieldrin | 83.3 | 71.9 | 88.4 | 80.4 |
| 4,4'-DDE | 54.0 | 43.3 | 59.2 | 53.6 |
| Endosulfan II | 105.5 | 87.1 | 119.6 | 103.9 |
| 4,4'-DDD | 87.0 | 62.9 | 76.1 | 92.8 |
| Endrin Aldehyde | 127.8 | 92.5 | 102.9 | 124.6 |
| Endosulfan Sulfate | 132.5 | 82.3 | 107.3 | 111.8 |
| 4,4'-DDT | 69.5 | 36.4 | 51.3 | 63.2 |
| Methoxychlor | 126.2 | 75.2 | 111.2 | 115.2 |
| Average Recovery | 93.1 | 66.1 | 81.9 | 91.6 |

C. Effect of Cross-Linker Ratio on Analyte Recovery
Extraction (QuEChERS)

A thoroughly homogenized avocado sample was weighed (15 g) into a 50 mL centrifuge tube and spiked with appropriate internal and QC standards at 100 ppb. An unspiked avocado sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD or α-CD containing polymers or blends.
Cleanup (dSPE)

The materials were weighed (100 mg) into a 2 mL centrifuge tube. Next, 0.5 mL of purified water was added to the solids (or 0.5 mL of α-CD solution only added) and then 0.5 mL of the acetonitrile avocado extract. Then, the mixture was vortexed for 1 min and then centrifuged at 13000 rpm for 3 min. The supernatant was then carefully decanted into a second 2 mL centrifuge tube containing 200 mg sodium chloride:magnesium sulfate (1:4). The mixture was vortex for 5 s and centrifuged at 13000 rpm for 3 min. The resulting supernatant gave phase separation with the acetonitrile layer on top. The upper layer was transferred to an autosampler vial for GC-MS analysis for quantitation.

TABLE 7

Recoveries of pesticides after treatment with 7a and 7b.

| | Pesticide Recoveries at 100 ppb by GC-MS (SIM) | |
|---|---|---|
| | 7a | 7b |
| α-BHC | 85.7 | 62.8 |
| β-BHC | 99.6 | 67.8 |
| γ-BHC | 82.0 | 62.6 |
| δ-BHC | 102.1 | 75.5 |

D. Comparison of dSPE Cleanup Procedures
Preparation of Gravimetric Determination of Residuals Glass test tubes were pre-dried in a vacuum oven overnight and weighed for an initial weight the following day.
Extraction (QuEChERS)

A thoroughly homogenized avocado sample was weighed (15 g) into a 50 mL centrifuge tube. An unspiked avocado sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD or α-CD containing polymers or blends.
Cleanup (dSPE)

The various materials were weighed directly into a 15 mL centrifuge tube. Two materials, C18-Zirconia and C18/PSA were used without any additional water content, as per recommended instructions for application. Water (5 mL) was added to the α-CD and 7a (1 g material), while the solution was added directly to the tube without additional water (5 mL). To each material, 5 mL of avocado extract was added and then vortexed for 1 min followed by centrifugation at 5000 rpm for 5 min. The C18-Zirconia, C18/PSA, and the untreated extract were transferred to preweighed test tubes (2 mL acetonitrile). The α-CD and 7a were decanted into a second IS mL centrifuge tube containing 2 g sodium chloride:magnesium sulfate (1:4) followed by vortexing for 5 s then centrifugation at 5000 rpm for 5 min. The upper acetonitrile layer (2 mL) was transferred to preweighed test tubes for gravimetric analysis. All tubes were evaporated in a centrifugal evaporator, dried in a vacuum oven, and then re-weighed in triplicate for determination of matrix residues.

TABLE 8

Mass of residuals and percent matrix removal after treatment with α-CD, α-CD solution, 7a, and other common dSPE cleanup materials.

| Cleanup | Amount of co-extractives (mg, n = 3) | Amount of matrix being removed by further cleanup (mg, n = 3) | % of matrix co-extractives removed by further cleanup |
|---|---|---|---|
| No further cleanup | 14.7 | — | |
| C18/PSA | 9.5 | 5.2 | 35.4 |
| 7a | 5.1 | 9.6 | 65.3 |
| α-CD | 4.2 | 10.5 | 71.4 |

TABLE 8-continued

Mass of residuals and percent matrix removal after treatment with α-CD, α-CD solution, 7a, and other common dSPE cleanup materials.

| Cleanup | Amount of co-extractives (mg, n = 3) | Amount of matrix being removed by further cleanup (mg, n = 3) | % of matrix co-extractives removed by further cleanup |
|---|---|---|---|
| α-CD solution | 3.2 | 11.5 | 78.2 |
| C18•Zirconia | 7.0 | 7.7 | 52.4 |

Recovery of Analytes in Avocado by LC-MS/MS Extraction (QuEChERS)

A thoroughly homogenized avocado sample was weighed (15 g) into a 50 mL centrifuge tube and spiked with appropriate internal and QC standards at 50 ppb. An unspiked avocado sample was also carried through the extraction process, to be used later as a matrix blank for matrix matched calibration standards. Then 15 mL, acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD or α-CD containing polymers or blends.

Cleanup (dSPE)

The materials were weighed (200 mg) into a 5 mL centrifuge tube. Two materials, C18-Zirconia and C18/PSA were used without any additional water content, as per recommended instructions for application. Next, 1 mL of purified water was added to the solids (or 1 mL of α-CD solution only added) and then 1 mL of the acetonitrile avocado extract. Then, the mixture was vortexed for 1 min and then centrifuged at 5000 rpm for 5 min. The supernatant was then carefully decanted into a second 5 mL centrifuge tube containing 400 mg sodium chloride:magnesium sulfate (1:4). The mixture was vortex for 5 s and centrifuged at 5000 rpm for 5 min. The resulting supernatant gave phase separation with the acetonitrile layer on top. The acetonitrile layers were transferred to an autosampler vial and diluted with water (5× dilution) for LC-MS/MS analysis. Each recovery was calculated using 6 replicates.

TABLE 9

Pesticide recoveries in avocado by LC-MS/MS (QQQ) for α-CD, α-CD solution, 7a, α-CD:7a blends, and other conventional dSPE materials.

| | Pesticide Recoveries at 50 ppb by LC-MS/MS (n = 6) | | | | | |
|---|---|---|---|---|---|---|
| | C18•Zirconia | C18/PSA | α-CD | α-CD solution | 7a | 1:1, α-CD:7a blend | 2:1, α-CD:7a blend |
| Pymetrazine | 56 | 75 | 75 | 52 | 52 | 42 | 68 |
| Methamidophos | 69 | 86 | 80 | 65 | 75 | 73 | 71 |
| Acephate | 88 | 91 | 86 | 69 | 83 | 87 | 90 |
| Omethoate | 84 | 93 | 91 | 71 | 85 | 90 | 94 |
| Carbendazim | 85 | 94 | 95 | 77 | 80 | 114 | 92 |
| Thiabendazole | 61 | 90 | 95 | 72 | 65 | 85 | 93 |
| Imidacloprid | 113 | 92 | 107 | 94 | 87 | 103 | 95 |
| Dimethoate | 88 | 94 | 104 | 84 | 114 | 107 | 107 |
| Imazalil | 42 | 88 | 96 | 69 | 69 | 48 | 95 |
| Thiophanate methyl | 56 | 76 | 77 | 64 | 87 | 13 | 98 |
| Propoxur | 94 | 98 | 102 | 78 | 111 | 105 | 109 |
| Carbaryl | 89 | 94 | 106 | 79 | 88 | 100 | 105 |
| Cyprodinil | 58 | 85 | 83 | 64 | 60 | 80 | 80 |
| Penconazole | 61 | 88 | 96 | 73 | 71 | 84 | 90 |
| TPP | 71 | 78 | 94 | 79 | 85 | 113 | 103 |
| Dichlorvos | 82 | 97 | 99 | 106 | 103 | 87 | 89 |
| Trichlorfon | 88 | 140 | 97 | 109 | 73 | 111 | 115 |
| 2-Phenylphenol | 89 | 139 | 99 | 101 | 90 | 100 | 86 |
| Ethalfluralin | 72 | 86 | 81 | 89 | 81 | 87 | 77 |
| Sulfotep | 85 | 96 | 98 | 101 | 100 | 108 | 98 |
| Atrazin | 86 | 96 | 109 | 105 | 92 | 102 | 96 |
| Lindane | 75 | 83 | 83 | 86 | 63 | 78 | 76 |
| Chlorothalonil | 89 | 113 | 96 | 101 | 35 | 62 | 78 |
| Diazinon | 81 | 91 | 98 | 99 | 94 | 97 | 93 |
| Chlorpyriphos-Me | 75 | 86 | 88 | 91 | 69 | 84 | 81 |
| Dichlorfluanid | 83 | 93 | 102 | 101 | 88 | 98 | 100 |
| Aldrin | 41 | 47 | 37 | 47 | 25 | 39 | 26 |
| Tolylfluanid | 79 | 92 | 104 | 101 | 85 | 96 | 97 |
| Captan | 93 | 94 | 129 | 100 | 72 | 95 | 115 |
| Procymidone | 87 | 96 | 99 | 105 | 87 | 96 | 104 |
| Folpet | 84 | 111 | 106 | 104 | 58 | 87 | 97 |
| Bupirimate | 94 | 97 | 128 | 119 | 101 | 103 | 100 |
| Endrin | 59 | 69 | 67 | 72 | 37 | 54 | 52 |
| Endosulfan sulfate | 84 | 96 | 100 | 105 | 69 | 87 | 97 |
| DDT | 49 | 62 | 55 | 56 | 24 | 44 | 33 |
| Captafol | 106 | 0 | 91 | 108 | 66 | 93 | 108 |
| Iprodione | 93 | 112 | 111 | 122 | 84 | 99 | 111 |
| Phosmet | 86 | 102 | 105 | 139 | 76 | 107 | 116 |

TABLE 9-continued

Pesticide recoveries in avocado by LC-MS/MS (QQQ) for α-CD, α-CD solution, 7a, α-CD:7a blends, and other conventional dSPE materials.

Pesticide Recoveries at 50 ppb by LC-MS/MS (n = 6)

|  | C18•Zirconia | C18/PSA | α-CD | α-CD solution | 7a | 1:1, α-CD:7a blend | 2:1, α-CD:7a blend |
|---|---|---|---|---|---|---|---|
| Coumaphos | 87 | 111 | 101 | 133 | 60 | 97 | 107 |
| Permethrin | 65 | 72 | 62 | 82 | 46 | 62 | 55 |
| Pyraclostrobin | 78 | 110 | 103 | 96 | 57 | 93 | 115 |
| Deltamethrin | 69 | 90 | 102 | 94 | 48 | 75 | 72 |
| Parathion Ethyl D10 (ISTD) | 76 | 88 | 90 | 91 | 69 | 97 | 98 |
| Average | 78 | 90 | 94 | 90 | 74 | 86 | 90 |

TABLE 10

Breakdown of average recovery of pesticides by polarity using different cleanups

|  | Polar Analytes (Log P < 1) | Medium polar analytes (1 < Log P < 3.5) | Non-polar analytes (Log P > 3.5) |
|---|---|---|---|
| PSA/C18 | 96.1 | 97.6 | 82.8 |
| C18/Zirconia | 85.1 | 81.2 | 72.7 |
| a-CD Solid | 92.8 | 98.4 | 89.9 |
| a-CD soln | 78.0 | 96.0 | 90.0 |
| MBPI | 85.0 | 74.1 | 67.8 |
| 1:1 Blend | 89.7 | 85.3 | 83.2 |
| 2:1 Blend | 91.8 | 98.2 | 92.4 |

III. Batch Reproducibility and Applications with α-CD:7a Blends

A. Pesticides in Avocado

Extraction (QuEChERS)

A thoroughly homogenized avocado sample was weighed (15 g) into a 50 mL centrifuge tube and spiked with appropriate internal and QC standards at 50 ppb. An unspiked avocado sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g sodium chloride was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD or α-CD containing polymers or blends.

Cleanup (dSPE)

The 2:1, α-CD:7a blends were weighed (200 mg) into a 5 mL centrifuge tube. Next, 1 mL of purified water was added to the solids and then 1 mL of the acetonitrile avocado extract. Then, the mixture was vortexed for 1 min and then centrifuged at 5000 rpm for 5 min. The supernatant was transferred to an autosampler vial directly for GC-MS/MS analysis and diluted with water (5x dilution) for LC-MS/MS analysis. Each recovery was calculated using 6 replicates.

TABLE 11

Average recovery for pesticides in avocado by GC-MS/MS and LC-MS/MS for 2:1, α-CD:7a blends.

Pesticide Recoveries at 50 ppb by GC-MS/MS and LC-MS/MS (n = 6)

|  | Batch A | Batch B | Batch C | Batch D | Batch E | Inter-batch average | Inter-batch % RSD |
|---|---|---|---|---|---|---|---|
| Pymetrazine | 52 | 50 | 59 | 53 | 45 | 54 | 7.6 |
| Methamidophos | 67 | 65 | 83 | 75 | 71 | 72 | 10.9 |
| Acephate | 86 | 81 | 94 | 83 | 76 | 86 | 6.7 |
| Omethoate | 88 | 83 | 99 | 88 | 78 | 90 | 7.5 |
| Carbendazim | 88 | 87 | 96 | 93 | 81 | 91 | 4.6 |
| Thiabendazole | 87 | 87 | 88 | 86 | 75 | 87 | 0.8 |
| Imidacloprid | 111 | 94 | 101 | 95 | 84 | 100 | 7.6 |
| Dimethoate | 114 | 102 | 103 | 97 | 93 | 104 | 7.1 |
| Imazalil | 97 | 93 | 93 | 93 | 83 | 94 | 2.1 |
| Thiophanate methyl | 104 | 102 | 84 | 90 | 84 | 95 | 10.1 |
| Propoxur | 105 | 105 | 109 | 102 | 97 | 105 | 2.9 |
| Carbaryl | 103 | 104 | 109 | 104 | 89 | 105 | 2.5 |
| Cyprodinil | 84 | 78 | 80 | 77 | 65 | 80 | 3.9 |
| Penconazole | 99 | 92 | 95 | 90 | 75 | 94 | 4.0 |
| TPP | 118 | 99 | 97 | 89 | 102 | 101 | 12.2 |
| Dichlorvos | 93 | 101 | 91 | 91 | 93 | 94 | 4.7 |
| Trichlorfon | 92 | 105 | 106 | 113 | 86 | 104 | 8.2 |
| 2-Phenylphenol | 90 | 96 | 93 | 87 | 89 | 92 | 4.5 |
| Ethalfluralin | 72 | 82 | 77 | 74 | 74 | 76 | 5.5 |
| Sulfotep | 89 | 97 | 96 | 93 | 93 | 94 | 3.6 |

TABLE 11-continued

Average recovery for pesticides in avocado by GC-MS/MS and LC-MS/MS for 2:1, α-CD:7a blends.

Pesticide Recoveries at 50 ppb by GC-MS/MS and LC-MS/MS (n = 6)

|  | Batch A | Batch B | Batch C | Batch D | Batch E | Inter-batch average | Inter-batch % RSD |
|---|---|---|---|---|---|---|---|
| Atrazin | 94 | 105 | 93 | 92 | 89 | 96 | 6.4 |
| Lindane | 76 | 81 | 75 | 67 | 69 | 75 | 7.7 |
| Chlorothalonil | 70 | 78 | 64 | 63 | 71 | 69 | 10.2 |
| Diazinon | 86 | 95 | 90 | 85 | 86 | 89 | 5.2 |
| Chlorpyriphos-Me | 75 | 81 | 77 | 73 | 74 | 76 | 4.6 |
| Dichlorfluanid | 80 | 97 | 90 | 91 | 91 | 90 | 7.9 |
| Aldrin | 32 | 22 | 21 | 17 | 32 | 23 | 27.9 |
| Tolylfluanid | 83 | 95 | 85 | 88 | 86 | 88 | 6.1 |
| Captan | 113 | 94 | 96 | 95 | 88 | 99 | 9.1 |
| Procymidone | 94 | 100 | 97 | 86 | 87 | 94 | 6.5 |
| Folpet | 87 | 98 | 76 | 84 | 76 | 86 | 10.6 |
| Bupirimate | 87 | 105 | 94 | 94 | 89 | 95 | 7.7 |
| Endrin | 46 | 29 | 28 | 25 | 50 | 32 | 29.1 |
| Endosulfan sulfate | 79 | 93 | 82 | 80 | 83 | 83 | 7.9 |
| DDT | 40 | 44 | 38 | 33 | 37 | 39 | 12.4 |
| Captafol | 86 | 101 | 85 | 96 | 88 | 92 | 8.6 |
| Iprodione | 99 | 105 | 97 | 96 | 91 | 99 | 3.8 |
| Phosmet | 90 | 103 | 93 | 107 | 97 | 98 | 8.1 |
| Coumaphos | 105 | 100 | 81 | 95 | 89 | 96 | 11.1 |
| Permethrin | 62 | 63 | 57 | 53 | 57 | 58 | 8.1 |
| Pyraclostrobin | 82 | 113 | 84 | 108 | 89 | 96 | 16.7 |
| Deltamethrin | 81 | 82 | 64 | 67 | 69 | 73 | 12.8 |
| Recovery Average | 85 | 88 | 84 | 83 | 79 |  |  |

B. Veterinary Drugs in Beef Liver

Extraction (QuEChERS)

A thoroughly homogenized beef liver sample was weighed (2 g) into a 50 mL centrifuge tube and spiked with appropriate internal and QC standards at 50 ppb. An unspiked beef liver sample was also carried through the extraction process, to be used later as a matrix blank for matrix matched calibration standards. To the sample, 8 mL of 30 mM $KH_2PO_4$, pH 7.0 was added, followed by vortexing for 10 s. Then 10 mL acetonitrile containing 5% formic acid was added to the tube and mixed for 2 min using a mechanical shaking unit. A salt packet containing anhydrous 1 g sodium chloride, 1 g sodium citrate, 0.5 g disodium citrate sesquihydrate, and 4.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then treated with the appropriate α-CD blends.

Cleanup (dSPE)

The 2:1, α-CD:7a blends were weighed (200 mg) into a 5 mL centrifuge tube. Next, 1 mL of purified water was added to the solids and then 1 mL of the acetonitrile beef liver extract. Then, the mixture was vortexed for 1 min and then centrifuged at 5000 rpm for 5 min. The supernatant was then carefully decanted into a second 5 mL centrifuge tube containing 400 mg sodium chloride; magnesium sulfate (1:4). The mixture was vortex for 5 s and centrifuged at 5000 rpm for 5 min. The resulting supernatant gave phase separation with the acetonitrile layer on top. The acetonitrile layers were transferred to clean, 2 mL centrifuge tubes and diluted with water (400 μL extract, 600 μL water) and centrifuged at 13000 rpm for 2 min. The supernatant was transferred to sample vials for LC-MS/MS analysis. Each recovery was calculated using 6 replicates.

TABLE 12

Average recovery for veterinary drugs in beef liver by LC-MS/MS for 2:1, α-CD:7a blends. Calculated as average inner- and inter-batch recoveries and inner- and inter-batch % RSD.

Veterinary Drug Recoveries at 50 ppb by LC-MS/MS (n = 6)

|  | Batch A | Batch B | Batch C | Batch D | Batch E | Inter-Batch Average | Inter-batch % RSD |
|---|---|---|---|---|---|---|---|
| 2-Thiouracil | 77 | 81 | 75 | 78 | 74 | 78 | 3.8 |
| Amoxicillin | 75 | 70 | 71 | 67 | 63 | 72 | 3.7 |
| Metronidazole-OH | 89 | 85 | 83 | 83 | 77 | 86 | 3.7 |
| Levamisole | 102 | 98 | 92 | 89 | 90 | 97 | 5.0 |
| Lincomycin | 74 | 72 | 68 | 69 | 68 | 71 | 3.9 |
| Norfloxacin | 74 | 89 | 69 | 77 | 61 | 77 | 13.2 |

TABLE 12-continued

Average recovery for veterinary drugs in beef liver by LC-MS/MS for 2:1, α-CD:7a blends. Calculated as average inner- and inter-batch recoveries and inner- and inter-batch % RSD.

Veterinary Drug Recoveries at 50 ppb by LC-MS/MS (n = 6)

|  | Batch A | Batch B | Batch C | Batch D | Batch E | Inter-Batch Average | Inter-batch % RSD |
|---|---|---|---|---|---|---|---|
| Oxytetracycline | 28 | 23 | 26 | 27 | 23 | 26 | 10.0 |
| Ciprofloxacin | 78 | 70 | 76 | 77 | 66 | 75 | 5.3 |
| Ractopamine | 84 | 74 | 93 | 71 | 100 | 84 | 11.0 |
| Danofloxacin | 79 | 66 | 81 | 77 | 72 | 75 | 11.2 |
| Cefazolin | 104 | 100 | 92 | 93 | 81 | 99 | 5.9 |
| Sulfamethizole | 113 | 106 | 97 | 88 | 80 | 106 | 7.9 |
| Sulfamethoxypyridazine | 110 | 110 | 92 | 82 | 85 | 104 | 10.2 |
| Difloxacin | 107 | 111 | 92 | 90 | 81 | 103 | 9.7 |
| Morantel | 104 | 97 | 92 | 87 | 95 | 98 | 6.3 |
| Chlortetracycline | 53 | 55 | 56 | 54 | 43 | 55 | 3.3 |
| Doxycycline | 48 | 53 | 46 | 45 | 38 | 49 | 7.2 |
| Florfenicol | 122 | 125 | 96 | 94 | 93 | 114 | 13.9 |
| Chloramphenicol | 115 | 129 | 93 | 96 | 98 | 112 | 16.3 |
| Tylosin | 94 | 100 | 88 | 82 | 89 | 94 | 6.5 |
| Acepromazine | 104 | 118 | 86 | 76 | 82 | 103 | 15.8 |
| Prednisone | 108 | 93 | 92 | 88 | 87 | 98 | 9.0 |
| Clorsulon | 108 | 118 | 93 | 92 | 91 | 106 | 11.8 |
| Chlorpromazine | 99 | 108 | 82 | 70 | 82 | 97 | 13.7 |
| Fenbendazole | 96 | 102 | 84 | 81 | 83 | 94 | 9.7 |
| Nafcillin | 93 | 102 | 91 | 81 | 79 | 95 | 5.9 |
| Ketoprofen | 114 | 95 | 92 | 92 | 104 | 101 | 12.0 |
| Oxyphenbutazone | 123 | 122 | 111 | 101 | 115 | 119 | 5.8 |
| Melengestrol acetate | 94 | 90 | 85 | 83 | 82 | 90 | 4.9 |
| Niclosamide | 85 | 67 | 66 | 64 | 120 | 73 | 14.4 |
| Bithionol | 94 | 82 | 86 | 88 | 127 | 87 | 6.8 |
| Average | 92 | 91 | 82 | 79 | 82 |  |  |

C. dSPE Treatment of Pesticide Standards

Pesticide Standards were prepared at 50 ppb in acetonitrile. Each 2:1, α-CD:7a batch was weighed out (200 mg) into 5 mL centrifuge tubes in replicates of 6. To each tube was added 1 mL of purified water and 1 mL of the acetonitrile solution containing pesticide standards. The mixture was vortex for 1 min and then centrifuged at 5000 rpm for 5 min. The supernatant was decanted into a new 5 mL centrifuge tube containing 400 mg of sodium chloride and magnesium sulfate (1:4) and vortex for 10 s. Next, the tubes were centrifuged at 5000 rpm for 5 min. The upper acetonitrile layer was transferred to sample vials and diluted with water (200 μL sample, 800 μL water) for LC-MS/MS analysis.

TABLE 13

Recovery and reproducibility for pesticides in acetonitrile by LC-MS/MS for 2:1, α-CD:7a blends.

Pesticide Recoveries at 50 ppb by GC-MS/MS and LC-MS/MS (n = 6)

| | Batch F | % RSD | Batch G | % RSD | Batch H | % RSD |
|---|---|---|---|---|---|---|
| Methamidophos | 92 | 4.8 | 89 | 5.7 | 96 | 5.6 |
| Acephate | 84 | 6.6 | 84 | 7.3 | 89 | 4.4 |
| Omethoate | 89 | 5.2 | 92 | 6.0 | 94 | 5.0 |
| Carbendazim | 94 | 3.8 | 93 | 2.7 | 94 | 3.6 |
| Thiabendazole | 87 | 4.4 | 87 | 4.3 | 86 | 4.9 |
| Imidacloprid | 102 | 7.4 | 113 | 3.7 | 113 | 3.3 |
| Dimethoate | 94 | 6.2 | 94 | 5.1 | 95 | 2.5 |
| Imazalil | 91 | 6.2 | 86 | 5.2 | 89 | 1.8 |
| Thiophanate methyl | 87 | 4.6 | 96 | 6.5 | 85 | 4.3 |
| Propoxur | 88 | 7.8 | 92 | 4.7 | 96 | 5.4 |
| Carbaryl | 96 | 4.7 | 98 | 4.5 | 98 | 2.3 |
| Cyprodinil | 95 | 3.9 | 93 | 2.9 | 93 | 1.7 |
| Penconazole | 95 | 4.4 | 94 | 11.3 | 90 | 1.7 |
| TPP (ISTD) | 105 | 11.3 | 104 | 21.4 | 110 | 14.5 |
| Average | 92.8 | 5.8 | 93.9 | 6.5 | 94.9 | 4.4 |

D. Matrix Removal of Various Sample Types Using Multiple Detectors

Extraction (QuEChERS)

Samples were weighed into 50 mL centrifuge tubes (1 g to 15 g depending on sample) and brought up to 15 g total with purified water (e.g. 1 g sample and 14 g water). Next, 15 mL of acetonitrile was added followed by mechanical shaking for 2 min. Salt packets were added containing 1.5 g sodium acetate and 6 g magnesium sulfate. The tubes were quickly shaken to avoid clumping and placed on a mechanical shaker for 2 min. The mixture was then centrifuged at 5000 rpm for 3 min. The upper acetonitrile layer was transferred for the dSPE cleanup steps.

Cleanup (dSPE)

The materials were weighed (200 mg) into a 5 mL centrifuge tube. Two materials, C18-Zirconia and C18/PSA were used without any additional water content, as per recommended instructions for application. Next, 1 mL of purified water was added to the and then 1 mL of the acetonitrile avocado extract. Then, the mixture was vortexed for 1 min and then centrifuged at 5000 rpm for 5 min. The supernatant was then carefully decanted into a second 5 mL centrifuge tube containing 400 mg sodium chloride:magnesium sulfate (1:4). The mixture was vortex for 5 s and centrifuged at 5000 rpm for 5 min. The resulting supernatant gave phase separation with the acetonitrile layer on top. The acetonitrile layers were transferred to sample tubes for GC analysis or placed in a clear vial for visual comparison.

TABLE 14

Matrix removal values calculated from various matrices, using different sorbents, on different GC detectors. Negative values indicate contaminants added from cleanup materials.

| Sample Type | PSA C18/PSA* PSA/GCB** | C18/PSA/GCB C18•Zirconia*** | 2:1, α-CD:7a blend |
|---|---|---|---|
| GC-MS Detection | | | |
| Avocado | 20* | 51*** | 96 |
| Onion | −3 | 22 | 41 |
| Strawberry | 5 | 21 | 10 |
| Plum | −6 | 17 | 12 |
| Red Pepper | −1 | 39 | 61 |
| Spinach | 49** | 51 | 61 |
| Orange | 27 | 34 | 52 |
| Black Pepper | −2** | 4 | 22 |
| Beef Liver | N/A | N/A | 98 |
| Olive Oil | N/A | N/A | 73 |
| Avocado Oil | N/A | N/A | 82 |
| Canola Oil | N/A | N/A | 75 |
| Paprika | N/A | N/A | 95 |
| Cumin | N/A | N/A | 72 |
| Hops | N/A | N/A | 57 |
| Tumeric | N/A | N/A | 47 |
| Wet Cat Food | N/A | N/A | 91 |
| Apple | N/A | N/A | 66 |
| GC/ECD Detection | | | |
| Avocado | 35* | 14*** | 80 |
| Onion | 22 | 31 | 36 |
| Strawberry | 52 | 57 | 73 |
| Plum | 65 | 76 | 82 |
| Red Pepper | 55 | 57 | 66 |
| Spinach | 55** | 41 | 29 |
| Orange | 70 | 72 | 75 |
| Black Pepper | 37** | 46 | 24 |
| GC/FID Detection | | | |
| Avocado | −33* | 8*** | 80 |
| Onion | −393 | −394 | 49 |
| Strawberry | −1520 | −1 | 41 |
| Plum | −1592 | −6 | 20 |
| Red Pepper | −7 | 14 | 76 |
| Spinach | 20** | 17 | 53 |
| Orange | −121 | −42 | 25 |
| Black Pepper | −9** | 1 | 29 |

IV. Treatment of Plasma with Protein Precipitation and Functional Filtration

Procedure for In-Tube Protein Precipitation with α-CD

Figure 7:
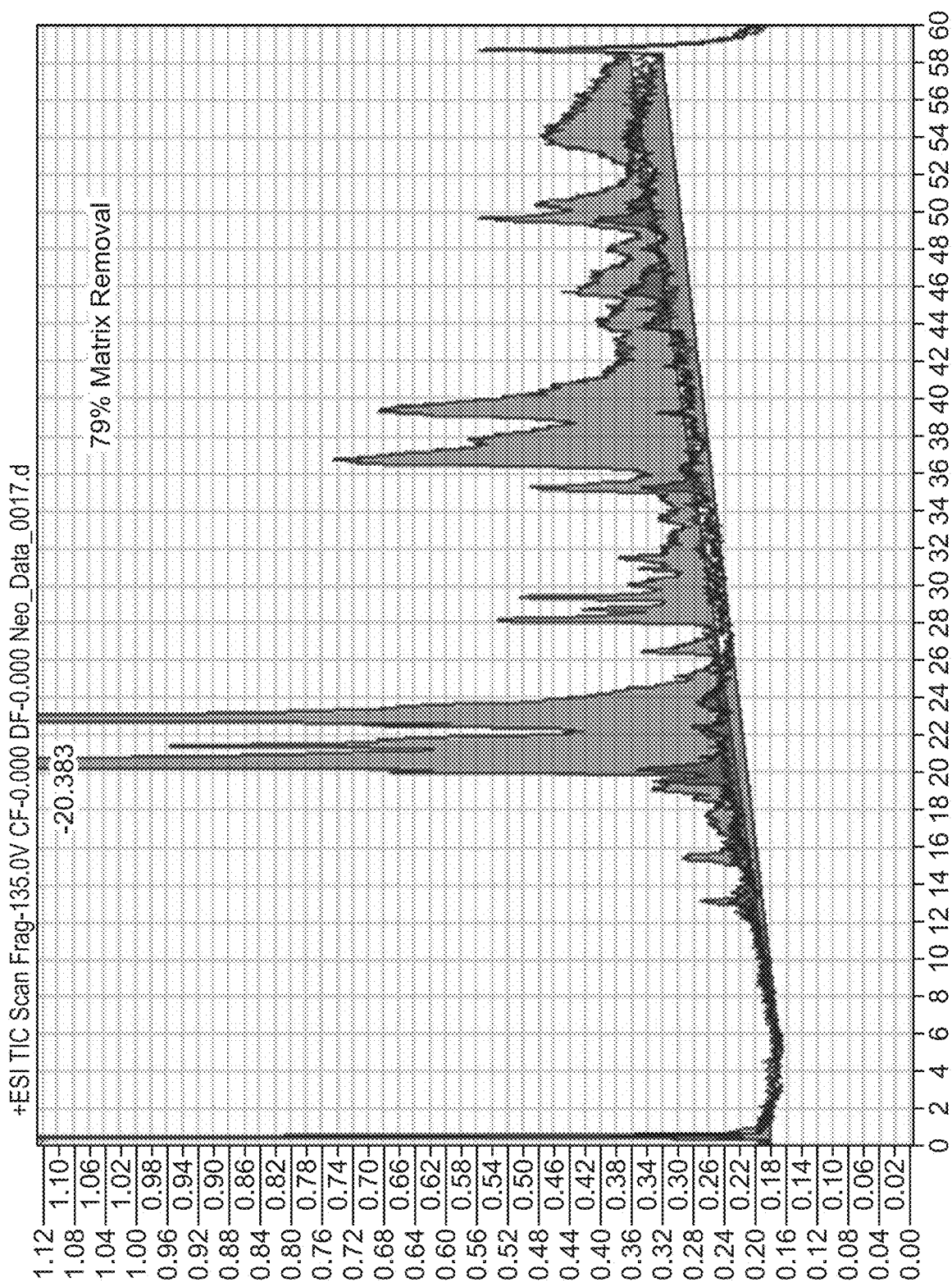
FIG. 7 shows an LC-MS fullscan chromatogram overlay (from top to bottom) of rat plasma without dSPE cleanup and after treatment with a 2:1, α-CD:α-CD co-polymer (7a) blend. Matrix removal as calculated by total peak area was 79%.

To a 2 mL centrifuge tube, 200 mg of 2:1 α-CD:7a blend was added followed by 100 μL of water. A plasma sample (100 μL) was added to the tube. Next, 600 μL of acetonitrile was added to induce protein precipitation. The sample was vortexed for 30 s and centrifuge at 14000 rpm for 3 min. Vacuum was pulled (~15 in Hg) in order to activate filtration through the non-drip membrane. The supernatant was added to a sample vial for LC-MS fullscan analysis. FIG. 7: Matrix removal in rat plasma by LC-MS fullscan. Matrix removal as calculated by total peak area was 79%.

Procedure for In-Cartridge Protein Precipitation with α-CD

A plasma sample was spiked with 50 ng/mL vitamin D metabolite standards and 100 ng/mL deuterated internal standards. Acetonitrile was added to a non-drip filter tube and/or 96-well plate (1 mL, Agilent Captiva ND, NDL) at 3:1 (600 μL), 4:1 (800 μL), or 6:1 (1200 μL). At the 3:1 ratio, total water content is 40%; at a 4:1 ratio, total water content is 33% and at a 6:1 ratio, total water content is 25%. Then 200 μL of plasma was added to induce protein precipitation. 200 μL of a 200 mg/mL solution of α-CD in water was added to α-CD treated samples. The mixture was homogenized by aspirating with a pipette for 5 cycles. Vacuum was pulled (~15 in Hg) in order to activate filtration through the non-drip membrane. The eluent was collected in a glass test tube and evaporated to dryness, then reconstituted in 200 μL of 3:1, methanol:water.

Procedure for Centrifuge Tube Protein Precipitation with α-CD (PPT)

A plasma sample was spiked with 50 ng/mL vitamin D metabolite standards and 100 ng/mL deuterated internal standards. To a 2 mL centrifuge tube and/or 96-well centrifuge plate, 200 pt of plasma was added. 200 μL of a 200 mg/mL solution of ca-CD in water was added to α-CD treated samples; or 200 μL water was added for tubes already containing 40 mg of solid α-CD and/or co-polymer. Acetonitrile was added at 3:1 (600 μL), 4:1 (800 μL), or 6:1 (1200 μL) ratios with respect to plasma volume to initiate protein precipitation. At the 3:1 ratio, total water content is 40%; at a 4:1 ratio, total water content is 33% and at a 6:1 ratio, total water content is 25%. The centrifuge tube was capped, vortexed for 10 s, then centrifuged at 13,000 rpm for 3 min. The supernatant was transferred to a glass test tube and evaporated to dryness, then reconstituted in 200 μL of 3:1, methanol:water.

TABLE 15

Recovery of vitamin D metabolite labelled standards from plasma using various cleanups and solvent:water ratios.

| | | Vitamin D Recoveries at 50 ppb by LC-MS/MS (n = 3) | | | |
|---|---|---|---|---|---|
| ACN to plasma | Method | Absolute Recovery 25-OH-D3 | Absolute Recovery 25-OH-D3-d3 | Absolute Recovery 25-OH-D2 | Absolute Recovery 25-OH-D2-d3 |
| 3 to 1 | Captiva ND | 58 | 58 | 50 | 50 |
| 3 to 1 | Captiva ND + α-CD | 77 | 69 | 69 | 70 |
| 3 to 1 | PPT | 66 | 67 | 58 | 58 |
| 3 to 1 | PPT + α-CD | 78 | 70 | 69 | 70 |
| 4 to 1 | Captiva ND | 62 | 48 | 50 | 49 |
| 4 to 1 | Captiva ND + α-CD | 76 | 66 | 61 | 57 |
| 4 to 1 | Captiva NDL | 30 | 27 | 19 | 19 |
| 4 to 1 | Captiva NDL + α-CD | 4 | 4 | 0 | 1 |
| 4 to 1 | PPT | 58 | 50 | 40 | 42 |
| 4 to 1 | PPT + α-CD | 84 | 73 | 69 | 66 |
| 6 to 1 | Captiva ND | 53 | 44 | 48 | 47 |
| 6 to 1 | Captiva ND + α-CD | 42 | 48 | 41 | 38 |
| 6 to 1 | Captiva NDL | 45 | 39 | 33 | 30 |
| 6 to 1 | Captiva NDL + α-CD | 32 | 29 | 26 | 23 |
| 6 to 1 | PPT | 52 | 49 | 42 | 40 |
| 6 to 1 | PPT + α-CD | 86 | 76 | 68 | 66 |

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

Embodiments

Embodiments of the present disclosure include a system for analytical sample treatment. In some embodiments, the system comprises a container having disposed therein an analytical sample treatment composition comprising: α-cyclodextrin; and/or an α-cyclodextrin co-polymer. In certain embodiments, the composition includes 5% to 100% by molarity of the α-cyclodextrin relative to the α-cyclodextrin co-polymer. In certain embodiments of the composition, the α-cyclodextrin co-polymer is optional. In some embodiments, the system comprises a plurality of the containers, each container having disposed therein the analytical sample treatment composition. In some embodiments of the system, the plurality of the containers is configured as a multiwell plate. In some embodiments of the system, the container is a filter tube comprising a porous membrane. In some embodiments of the system, the porous membrane is a lipid retaining membrane. In some embodiments of the system, the porous membrane comprises the α-cyclodextrin co-polymer.

Also provided is a method of reducing matrix effects in an analytical sample. In some embodiments, the method comprises: contacting a sample comprising a matrix-interfering agent and an analyte with a cyclodextrin composition to produce a matrix-cyclodextrin complex, wherein the cyclodextrin composition comprises an α-cyclodextrin and an α-cyclodextrin co-polymer; separating the complex from the contacted sample to produce a matrix-reduced composition; and detecting the analyte in the matrix-reduced composition. In some embodiments of the method, the matrix-reduced composition has a reduced deleterious effect on sensitivity of the detecting the analyte. In some embodiments of the method, the detecting is performed using mass spectrometry. In some embodiments of the method, the detecting is performed using UV/vis spectroscopy. In some embodiments of the method, the amount of analyte in the matrix-reduced composition and the amount of analyte in the sample are the same.

In some embodiments, the method further comprises quantitating the amount of analyte in the sample. In some embodiments, the matrix-reduced composition has reduced matrix effects on the quantitating the amount of analyte. In some embodiments of the method, the sample is a QuEChERS extract. In some embodiments of the method, the matrix-interfering agent is an aliphatic lipid and the complex comprises a lipid-α-cyclodextrin complex. In some embodiments of the method, the complex is insoluble in the contacted sample. In some embodiments of the method, the separating comprises centrifugation of the complex from the contacted sample. In some embodiments of the method, the separating comprises filtering the complex from the contacted sample. In some embodiments of the method, the separating comprises centrifugation to separate the complex from the contacted sample. In some embodiments of the method, the sample is a biological sample. In some embodiments of the method, the cyclodextrin composition comprises an α-cyclodextrin co-polymer immobilized in a porous membrane. In some embodiments of the method, the separating step comprises filtering the sample through the porous membrane. In some embodiments of the method, the separating step further comprises filtering precipitated proteins from the contacted sample.

In some embodiments, the method further comprises contacting the sample with an extraction solvent to produce a sample extract, and wherein the separating comprises separating the complex from the sample extract. In some instances, the separating comprises separating the sample matrix and the complex from the sample extract.

Embodiments of the present disclosure include a kit, comprising a cyclodextrin composition comprising α-cyclodextrin, an α-cyclodextrin co-polymer or a mixture thereof; and one or more components selected from QuEChERS extraction salts, an analyte extraction solvent, a quantitation standard, a porous membrane and a precipitation solvent.

Embodiments of the present disclosure include a composition for analytical sample treatment. In some embodiments, the composition comprises: an α-cyclodextrin; and an α-cyclodextrin co-polymer. In some embodiments of the composition, the α-cyclodextrin co-polymer further comprises β-cyclodextrin or γ-cyclodextrin co-monomers. In some embodiments of the composition, the α-cyclodextrin co-polymer comprises an α-cyclodextrin co-monomer and polymer backbone linkages selected from the group consisting of carbamate, vinyl, ether, acrylate, methacrylate, amide, aramid, ester, urethane, and carbonate. In some embodiments of the composition, the cyclodextrin co-polymer has a random network structure. In some embodiments of the composition, the cyclodextrin co-polymer has a linear, dendritic, or brush polymeric structure. In some embodiments of the composition, the cyclodextrin co-polymer comprises α-cyclodextrin co-monomers that are branched or functionalized co-monomers. In some embodiments of the composition, the cyclodextrin co-polymer comprises nano- to micron-scale particles. In some embodiments of the composition, the cyclodextrin co-polymer comprises a porous monolithic substrate. In some embodiments of the composition, the cyclodextrin co-polymer comprises a film, wherein the film is configured on the surface of a solid support. In some embodiments of the composition, the α-cyclodextrin co-polymer is a polyurethane polymer. In some embodiments of the composition, the α-cyclodextrin co-polymer has an average MW of 1000 kDa or less.

In some embodiments of the composition, the α-cyclodextrin co-polymer is described by Formula (I):

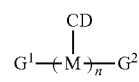

(I)

wherein:

M is a repeating monomeric unit of a polymer;
each CD is an optional α-cyclodextrin;
$G^1$ and $G^2$ are each independently a terminal capping group, a polymer segment, a linker or a linked specific binding member, and
n is an integer from 1 to 10,000.

In some embodiments of the composition, the α-cyclodextrin co-polymer is described by Formula (II):

(II)

wherein:
CD is an α-cyclodextrin co-monomer,
M is a second co-monomer,
$G^1$ and $G^2$ are each independently a terminal capping group, a polymer segment, a linker or a linked specific binding member;
x, and y, are independently an integer from 1 to 1000; and
n is independently an integer from 1 to 1000.

In some embodiments of the composition, the molar ratio of x to y is in the range of 1:1 to 1:3. In some embodiments of the composition, the α-cyclodextrin co-polymer is described by Formula (III):

(III)

wherein:
CD is an α-cyclodextrin co-monomer,
M is a co-monomer;
M' is a repeating unit of a polymer;
each x is independently an integer from 1 to 1000;
each y is independently an integer from 1 to 1000;
n is an integer from 1 to 10,000;
$G^1$, $G^2$, $G^{11}$ and $G^{12}$ are each independently a terminal capping group, a polymer segment, a linker or a linked specific binding member, and
m is an integer from 1 to 10,000.

In some embodiments of the composition, M is a rigid aryl-containing co-monomer. In some embodiments of the composition, the rigid aryl-containing co-monomer is derived from a 4,4'-methylenebis(phenyl-isocyanate) co-monomer. In some embodiments of the composition, the cyclodextrin co-polymer comprises a 1:1 ratio of α-cyclodextrin co-monomer to methylenebis(phenyl-isocyanate) co-monomer.

In some embodiments of the composition, the α-cyclodextrin co-polymer is described by Formula (V):

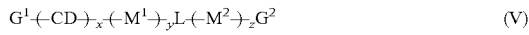
(V)

wherein:
CD is an α-cyclodextrin co-monomer;
M and M' are each independently selected from the group consisting of an aryl, a substituted aryl, a heteroaryl, a substituted heteroaryl, an alkyl, a substituted alkyl, a heterocycle, a substituted heterocycle, a cycloalkyl and a substituted cycloalkyl;
L is an optional linker linking M and M';
$G^1$ and $G^2$ are each independently a terminal capping group, a polymer segment, a linker or a linked specific binding member; and
x, y and z are the molar ratios of CD, M and M' co-monomers in the co-polymer.

In some embodiments of the composition, the α-cyclodextrin co-polymer is described by Formula (IV):

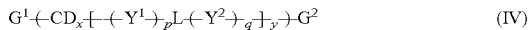
(IV)

wherein:
CD is a cyclodextrin co-monomer selected from α-cyclodextrin, β-cyclodextrin, γ-cyclodextrin and mixtures thereof;
$[(Y^1)_p\text{-}L\text{-}(Y^2)_q]$ is a second co-monomer, wherein $Y^1$ and $Y^2$ are each independently selected from the group consisting of an aryl, a substituted aryl, a heteroaryl, a substituted heteroaryl, an alkyl, a substituted alkyl, a heterocycle, a substituted heterocycle, a cycloalkyl and a substituted cycloalkyl; p and q are each independently 0 or 1, wherein p+q≥1; and L is an optional linker;
$G^1$ and $G^2$ are each independently a terminal capping group, a polymer segment, a linker or a linked specific binding member; and
x and y are molar ratios of the CD and the $[(Y^1)_p\text{-}L\text{-}(Y^2)_q]$ co-monomers in the co-polymer.

In some embodiments of the composition, the $[(Y^1)_p\text{-}L\text{-}(Y^2)_q]$ co-monomer is derived from a 4,4'-methylenebis(phenyl-isocyanate). In some embodiments of the composition, $Y^1$ and $Y^2$ are each independently selected from an alkyl, cyclohexane, phenyl and methyl-substituted phenyl. In some embodiments of the composition, L is absent, a covalent bond or an alkyl. In some embodiments of the composition, the co-polymer comprises a co-monomer derived from one of the following diisocyanates 1-9:

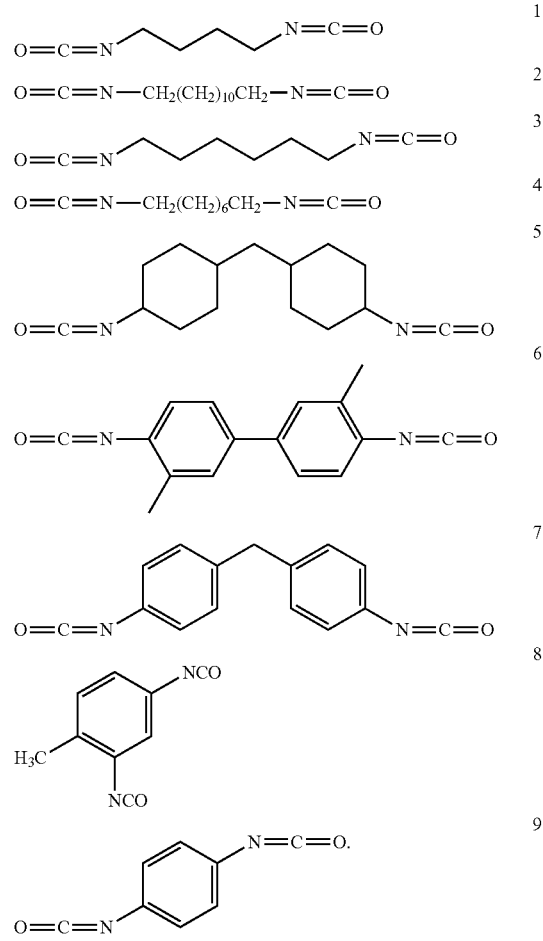

In some embodiments of the composition, the ratio of cyclodextrin to cyclodextrin co-polymer in the composition is in the range of 1:1 to 3:1.

What is claimed is:

1. A system for analytical sample treatment, comprising a container having disposed therein an analytical sample treatment composition comprising:
   a monomeric α-cyclodextrin compound; and
   an α-cyclodextrin co-polymer,
   wherein the composition comprises at least 5% monomeric α-cyclodextrin compound relative to the α-cyclodextrin co-polymer by molarity.

2. The system of claim 1, wherein the container is a filter tube comprising a porous membrane.

3. The system of claim 2, wherein the porous membrane comprises the α-cyclodextrin co-polymer.

4. The system of claim 1, wherein the composition comprises at least 50% monomeric α-cyclodextrin compound relative to the α-cyclodextrin co-polymer by molarity.

5. A composition for analytical sample treatment, comprising:
   a monomeric α-cyclodextrin compound; and
   an α-cyclodextrin co-polymer described by Formula (IV):

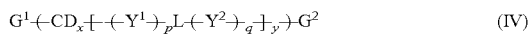

wherein:
   CD is α-cyclodextrin;
   $[(Y^1)_p\text{-L-}(Y^2)_q]$ is a second co-monomer, wherein $Y^1$ and $Y^2$ are each independently selected from the group consisting of an aryl, a substituted aryl, a heteroaryl, a substituted heteroaryl, an alkyl, a substituted alkyl, a heterocycle, a substituted heterocycle, a cycloalkyl and a substituted cycloalkyl; p and q are each independently 0 or 1, wherein $p+q \geq 1$; and L is an optional linker;
   $G^1$ and $G^2$ are each independently a terminal capping group, a polymer segment, a linker or a linked specific binding member; and
   x and y are molar ratios of the CD and the $[(Y^1)_p\text{-L-}(Y^2)_q]$ co-monomers in the co-polymer,
   wherein the composition comprises at least 5% monomeric α-cyclodextrin compound relative to the α-cyclodextrin co-polymer by molarity.

6. The composition of claim 5, wherein the α-cyclodextrin co-polymer comprises polymer backbone linkages selected from the group consisting of carbamate, vinyl, ether, acrylate, methacrylate, amide, aramid, ester, urethane, and carbonate.

7. The composition of claim 5, wherein $Y^1$ and $Y^2$ are each independently selected from an alkyl, cyclohexane, phenyl and methyl-substituted phenyl.

8. The composition of claim 5, wherein L is absent, a covalent bond or an alkyl.

9. The composition of claim 5, wherein the α-cyclodextrin co-polymer comprises a co-monomer derived from one of the following diisocyanates 1-9:

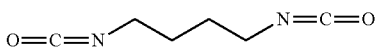

1

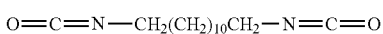

2

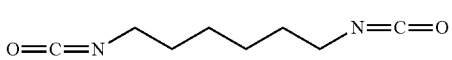

3

4

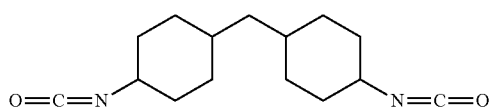

5

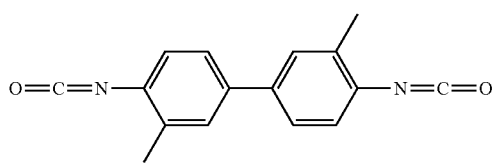

6

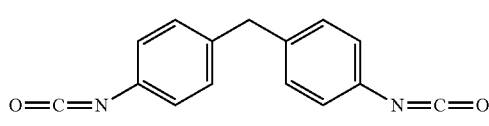

7

8

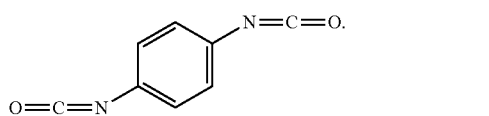

9

10. The composition of claim 5, wherein the $[(Y^1)_p\text{-L-}(Y^2)_q]$ co-monomer is derived from a 4,4'-methylenebis(phenyl-isocyanate).

11. A kit comprising:
   a composition of claim 5; and
   one or more components selected from QuEChERS extraction salts, an analyte extraction solvent, a quantitation standard, a porous membrane and a precipitation solvent.

12. A method of reducing matrix effects in an analytical sample, the method comprising:
   contacting a sample comprising a matrix-interfering agent and an analyte with a composition of claim 5 to produce a matrix-cyclodextrin complex;
   separating the complex from the contacted sample to produce a matrix-reduced composition; and
   detecting the analyte in the matrix-reduced composition.

13. The method of claim 12, wherein the matrix-reduced composition has a reduced deleterious effect on sensitivity of the detecting the analyte.

14. The method of claim 12, wherein the detecting is performed using mass spectrometry.

15. The method of claim 12, wherein the amount of analyte in the matrix-reduced composition and the amount of analyte in the sample are the same.

16. The method of claim 12, further comprising quantitating the amount of analyte in the sample, and wherein the matrix-reduced composition has reduced matrix effects on the quantitating the amount of analyte.

17. The method of claim 12, wherein the matrix interfering agent is an aliphatic lipid and the complex comprises a lipid-α-cyclodextrin complex.

18. The method of claim 12, wherein the complex is insoluble in the contacted sample.

19. The method of claim 12, wherein the separating step further comprises filtering precipitated proteins from the contacted sample.

20. The method of claim 12, further comprising contacting the sample with an extraction solvent to produce a sample extract, and wherein the separating comprises separating the complex from the sample extract.

* * * * *

UNITED STATES PATENT AND TRADEMARK OFFICE
CERTIFICATE OF CORRECTION

PATENT NO. : 10,564,076 B2
APPLICATION NO. : 14/740829
DATED : February 18, 2020
INVENTOR(S) : Derick Lucas et al.

It is certified that error appears in the above-identified patent and that said Letters Patent is hereby corrected as shown below:

In the Specification

In Column 19, Line 17, should read:
selected from alkyl, cyclohexyl, phenyl, and methyl-substituted In Column 56, Line 24, should read:
alkyl, cyclohexyl, phenyl, and methyl-substituted phenyl.

In the Claims

In Column 57, Line 52, Claim 7 should read:
7. The composition of claim 5, wherein Y1 and Y2 are each independently selected from an alkyl, cyclohexyl, phenyl, and methyl-substituted phenyl.

Signed and Sealed this
Sixth Day of July, 2021

Drew Hirshfeld
*Performing the Functions and Duties of the
Under Secretary of Commerce for Intellectual Property and
Director of the United States Patent and Trademark Office*